United States Patent
Kawamura et al.

(10) Patent No.: US 10,211,404 B2
(45) Date of Patent: *Feb. 19, 2019

(54) COMPOUND, MATERIAL FOR ORGANIC ELECTROLUMINESCENT ELEMENTS, ORGANIC ELECTROLUMINESCENT ELEMENT AND ELECTRONIC DEVICE

(71) Applicant: IDEMITSU KOSAN CO., LTD., Tokyo (JP)

(72) Inventors: Masahiro Kawamura, Chiba (JP); Yumiko Mizuki, Basel (CH); Hirokatsu Ito, Ichihara (JP); Tomoharu Hayama, Utsunomiya (JP); Tasuku Haketa, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/114,254

(22) PCT Filed: Jan. 29, 2015

(86) PCT No.: PCT/JP2015/052483
§ 371 (c)(1),
(2) Date: Jul. 26, 2016

(87) PCT Pub. No.: WO2015/115532
PCT Pub. Date: Aug. 6, 2015

(65) Prior Publication Data
US 2017/0012209 A1  Jan. 12, 2017

(30) Foreign Application Priority Data

Jan. 31, 2014 (JP) ................ 2014-017384

(51) Int. Cl.
*H01L 51/00* (2006.01)
*C07F 9/53* (2006.01)
(Continued)

(52) U.S. Cl.
CPC ........ *H01L 51/0054* (2013.01); *C07F 9/5325* (2013.01); *C07F 9/5329* (2013.01);
(Continued)

(58) Field of Classification Search
CPC ........ H01L 51/5016; H01L 51/5012–51/5044; H01L 51/0032–51/0095; C07F 9/5325;
(Continued)

(56) References Cited

U.S. PATENT DOCUMENTS 9,040,512 B2 * 5/2015 Anemian ............ C07F 15/0033
514/183
2007/0228356 A1 * 10/2007 Makiura ............ H01L 51/5092
257/13
(Continued)

FOREIGN PATENT DOCUMENTS

CN  103187531 A  7/2013
JP  2002-063989 A  2/2002
(Continued)

OTHER PUBLICATIONS

International Search Report issued in International Patent Application No. PCT/JP2015/052483 dated Apr. 21, 2015.
(Continued)

*Primary Examiner* — Kevin M Picardat
(74) *Attorney, Agent, or Firm* — Foley & Lardner LLP

(57) ABSTRACT

A high-performance organic electroluminescence device and an electronic equipment provided with the organic electroluminescence device are provided. Also, a compound for achieving the organic electroluminescence device and the electronic equipment is provided. Specifically, a com-
(Continued)

pound having a specific structure having a triphenylene skeleton, an organic electroluminescence device using the compound and an electronic equipment provided with the organic electroluminescence device are provided.

27 Claims, 1 Drawing Sheet

(51) Int. Cl.
- C07F 9/572 (2006.01)
- C07F 9/64 (2006.01)
- C07F 9/655 (2006.01)
- C07F 9/6553 (2006.01)
- C09K 11/06 (2006.01)
- C07F 9/58 (2006.01)
- H01L 51/50 (2006.01)

(52) U.S. Cl.
CPC .............. *C07F 9/5728* (2013.01); *C07F 9/58* (2013.01); *C07F 9/64* (2013.01); *C07F 9/65517* (2013.01); *C07F 9/655354* (2013.01); *C09K 11/06* (2013.01); *H01L 51/0055* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/5072* (2013.01); *H01L 51/5076* (2013.01)

(58) Field of Classification Search
CPC ...... C07F 9/5329; C07F 9/5728; C07F 9/587; C07F 9/64; C07F 9/65517; C07F 9/655354; C09K 11/06
See application file for complete search history.

(56) References Cited

U.S. PATENT DOCUMENTS

| | | | | |
|---|---|---|---|---|
| 2007/0290605 | A1* | 12/2007 | Goto | C07F 9/5329 313/504 |
| 2009/0072727 | A1* | 3/2009 | Takeda | C09K 11/06 313/504 |
| 2012/0146014 | A1* | 6/2012 | Kato | C07D 209/86 257/40 |
| 2012/0261651 | A1* | 10/2012 | Noto | C09K 11/06 257/40 |
| 2015/0034927 | A1* | 2/2015 | Nakano | C07F 9/65517 257/40 |
| 2016/0343950 | A1* | 11/2016 | Kawamura | H01L 51/0054 |

FOREIGN PATENT DOCUMENTS

| | | |
|---|---|---|
| JP | 2004-204140 A | 7/2004 |
| JP | 2006-073581 A | 3/2006 |
| JP | 2010-278376 | 12/2010 |
| WO | WO-2011/021385 A1 | 2/2011 |
| WO | WO-2012/173370 A2 | 12/2012 |
| WO | WO-2015/002295 A1 | 1/2015 |
| WO | WO-2015/115530 | 3/2017 |
| WO | WO-2013/118507 A1 | 8/2017 |

OTHER PUBLICATIONS

Japanese Office Action dated Apr. 3, 2018 in corresponding application No. 2015-560006.

Japanese Office Action dated Sep. 25, 2018 in corresponding application No. 2015-560006.

* cited by examiner

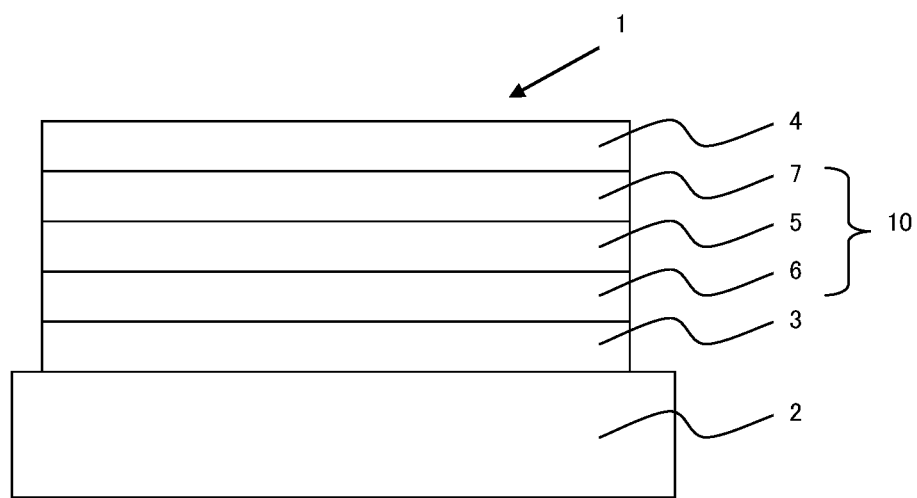

COMPOUND, MATERIAL FOR ORGANIC ELECTROLUMINESCENT ELEMENTS, ORGANIC ELECTROLUMINESCENT ELEMENT AND ELECTRONIC DEVICE

CROSS-REFERENCE TO RELATED APPLICATIONS

The present application is a U.S. national stage application of International Patent Application No. PCT/JP2015/052483, filed Jan. 29, 2015, which claims the benefit of priority to Japanese Patent Application No. 2014-017384, filed Jan. 31, 2014, the entireties of which are hereby incorporated by reference.

TECHNICAL FIELD

The present invention relates to a compound, a material for an organic electroluminescence device containing the compound, an organic electroluminescence device using the compound and an electronic equipment provided with the organic electroluminescence device.

BACKGROUND ART

In general, an organic electroluminescence (EL) device is composed of an anode, a cathode and one or more organic thin film layers placed between the anode and the cathode. When voltage is applied across the electrodes, electrons and holes are injected into the light emitting region from the cathode side and from the anode side, respectively. The injected electrons and holes recombine in the light emitting region and are promoted to an excited state, and light is emitted when the excited state returns to the ground state.

Because a wide variety of colors can be obtained when various luminescent materials are used for the light emitting layer, intensive studies on the practical use of an organic EL device, for example use in a display, are conducted. In particular, the studies on luminescent materials for the three primary colors, red, green and blue, are most extensively conducted, and the materials are studied intensively for the improvement of the properties.

As materials for such an organic EL device, phosphine oxide compounds are disclosed in PTLs 1 to 3. However, in the field of organic EL devices, development of new materials is required to further improve the performance of the devices.

CITATION LIST

Patent Literature

PTL 1: JP 2002-63989 A
PTL 2: JP 2006-73581 A
PTL 3: JP 2004-204140 A

SUMMARY OF INVENTION

Technical Problem

Thus, an object of the present invention is to provide a higher-performance organic electroluminescence device, specifically an organic electroluminescence device having an excellent driving voltage, an excellent external quantum efficiency and an extended lifetime, and an electronic equipment provided with the organic electroluminescence device, and to provided a compound for achieving the organic electroluminescence device and the electronic equipment.

Solution to Problem

As a result of intensive studies, the present inventors have found that the objects can be achieved by a compound having a specific structure having a triphenylene skeleton. The present invention has been made based on the findings.

According to aspects of the present invention, the following [1] to [4] are provided.

[1] A compound represented by the following general formula (1):

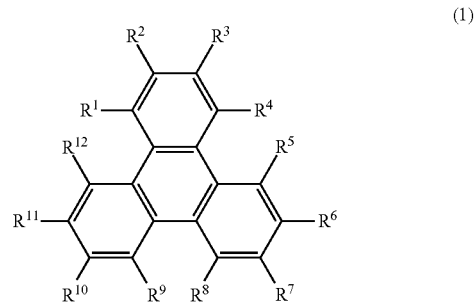

wherein in the general formula (1), $R^1$ to $R^{12}$ are each independently a hydrogen atom or a substituent, and the substituents of at least a pair selected from $R^1$ and $R^2$, $R^2$ and $R^3$, $R^3$ and $R^4$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ may combine to form a ring, provided that at least one of $R^1$ to $R^{12}$ (including a group bonded to the ring when the substituents of the pair combine to form a ring) is a group represented by the following general formula (2);

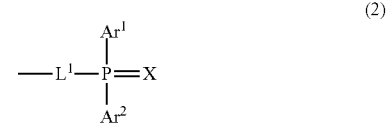

wherein in the general formula (2), X represents an oxygen atom, a sulfur atom or a selenium atom, $L^1$ is a direct bond, a substituted or unsubstituted arylene group having 6 to 60 ring carbon atoms or a substituted or unsubstituted heteroarylene group having 5 to 60 ring atoms, $Ar^1$ and $Ar^2$ are each independently a substituted or unsubstituted aryl group having 6 to 60 ring carbon atoms or a heteroaryl group having 5 to 60 ring atoms, and $Ar^1$ and $Ar^2$ may combine to form a ring.

[2] A material for an organic electroluminescence device including the compound according to the above [1].

[3] An organic electroluminescence device including one or more organic thin film layers including at least a light emitting layer between an anode and a cathode which face each other, wherein at least one of the organic thin film layers contains the compound according to the above [1].

[4] An electronic equipment provided with the organic electroluminescence device according to the above [3].

Advantageous Effects of Invention

According to the present invention, a higher-performance organic electroluminescence device, specifically an organic electroluminescence device having an excellent driving voltage, an excellent external quantum efficiency and an extended lifetime, and an electronic equipment provided with the organic electroluminescence device can be provided, and a compound capable of achieving the organic electroluminescence device and the electronic equipment can be provided.

BRIEF DESCRIPTION OF DRAWINGS

FIG. 1 shows an example of a schematic configuration of an organic electroluminescence device (hereinunder sometimes abbreviated to "an organic EL device" below) according to an embodiment of the present invention.

DESCRIPTION OF EMBODIMENTS

In the present specification, the "XX to YY carbon atoms" in an expression "a substituted or unsubstituted ZZ group having XX to YY carbon atoms" refer to the carbon atoms of the unsubstituted ZZ group, and when the ZZ group has a substituent, the carbon atoms of the substituent are not included. Here, "YY" is larger than "XX", and "XX" and "YY" each mean an integer of one or larger.

The term "hydrogen atom" includes isotopes with a different number of neutrons, namely protium, deuterium and tritium.

The term "unsubstituted" in the term "substituted or unsubstituted" means that the group does not have the substituents and that a hydrogen atom is bonded.

In the present specification, the number of the ring carbon atoms refers to the number of the carbon atoms of the atoms constituting the ring itself of a compound having a structure in which the atoms combine and form a ring (for example, a monocyclic compound, a condensed ring compound, a cross-linked compound, a carbocyclic compound or a heterocyclic compound). When the ring has a substituent, the carbon atoms contained in the substituent are not counted as the ring carbon atoms. The term "ring carbon atoms" used below is the same unless otherwise noted. For example, a benzene ring has six ring carbon atoms, and a naphthalene ring has 10 ring carbon atoms. A pyridinyl group has five ring carbon atoms, and a furanyl group has four ring carbon atoms. When a benzene ring or a naphthalene ring has an alkyl group as a substituent for example, the carbon atoms of the alkyl group are not counted as the ring carbon atoms. Also, when a fluorene ring is bonded to another fluorene ring as a substituent for example (including a spirofluorene ring), the carbon atoms of the fluorene ring as the substituent are not counted as the ring carbon atoms.

The number of the ring atoms refers to the number of the atoms constituting the ring itself of a compound having a structure in which the atoms combine and form a ring (for example a monocycle, a condensed ring or a ring assembly) (for example, the compound is a monocyclic compound, a condensed ring compound, a cross-linked compound, a carbocyclic compound or a heterocyclic compound). The atoms which do not constitute the ring (for example, a hydrogen atom which terminates a binding site of an atom constituting the ring) and the atoms contained in a substituent which the ring has, if any, are not counted as the ring atoms. The term "ring atoms" used below is the same unless otherwise noted. For example, a pyridine ring has six ring atoms, and a quinazoline ring has 10 ring atoms. A furan ring has five ring atoms. The hydrogen atoms bonded to the carbon atoms of a pyridine ring or a quinazoline ring and the atoms constituting a substituent are not counted as the ring atoms. When a fluorene ring is bonded to another fluorene ring as a substituent for example (including a spirofluorene ring), the atoms of the fluorene ring as the substituent are not counted as the ring atoms.

The "heteroaryl group" in the present specification is a group containing at least one hetero atom as a ring atom, and the hetero atom is preferably one or more selected from a nitrogen atom, an oxygen atom, a sulfur atom and a selenium atom. Similarly the "hetero aromatic ring" is a ring containing at least one hetero atom as a ring atom, and the hetero atom is preferably one or more selected from a nitrogen atom, an oxygen atom, a sulfur atom and a selenium atom.

In the present specification, the "substituted or unsubstituted carbazolyl group" includes the following carbazolyl groups:

[Chem. 3]

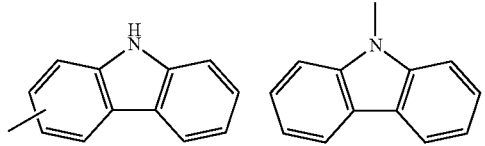

and a substituted carbazolyl group having any of the optional substituents above as well as the following substituted carbazolyl groups for example.

[Chem. 4]

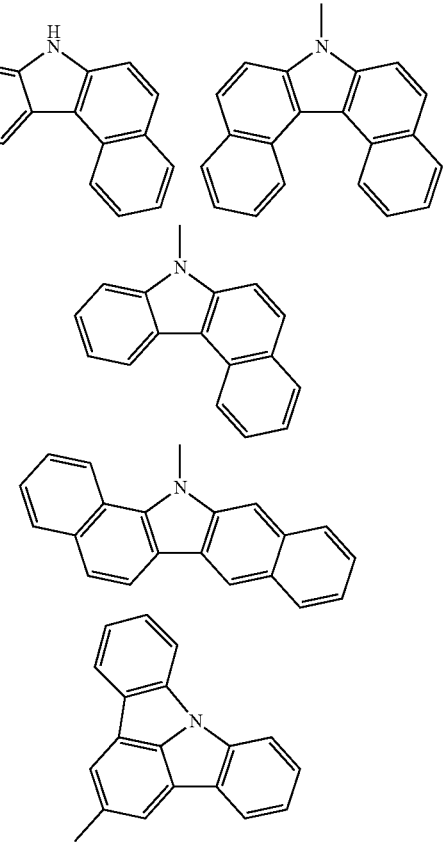

In the present specification, the substituted or unsubstituted dibenzofuranyl group and the substituted or unsubstituted dibenzothiophenyl group include the following dibenzofuranyl group and dibenzothiophenyl group:

[Chem. 5]

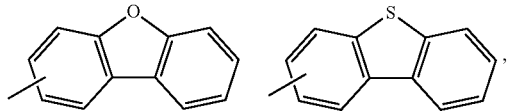

a substituted dibenzofuranyl group having any of the optional substituents above and a substituted dibenzothiophenyl group having any of the optional substituents above as well as for example the following substituted dibenzofuranyl groups and substituted dibenzothiophenyl groups, wherein X represents an oxygen atom or a sulfur atom, and Y represents an oxygen atom, a sulfur atom, NH, NR$^a$ (R$^a$ is an alkyl group or an aryl group), CH$_2$ or CR$^b_2$ (R$^b$ is an alkyl group or an aryl group).

[Chem. 6]

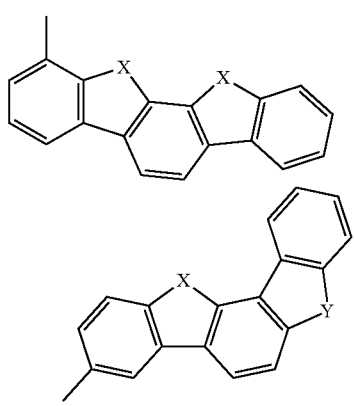

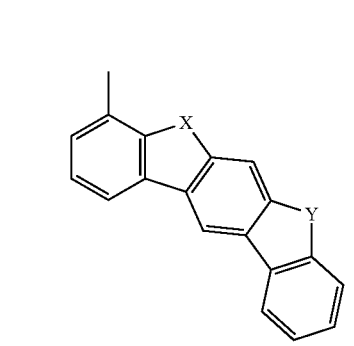

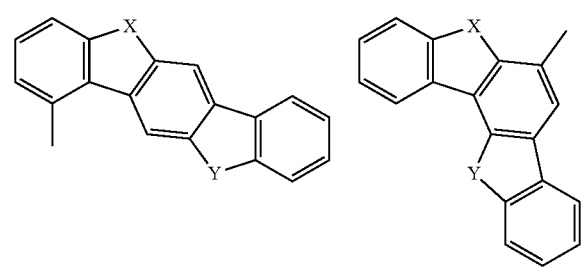

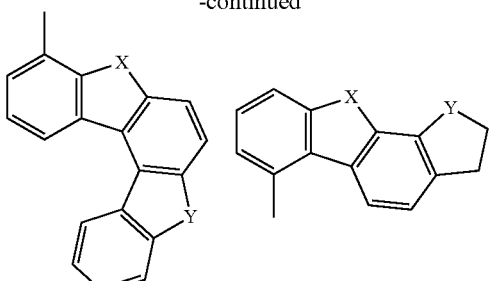

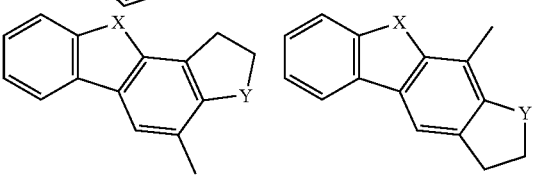

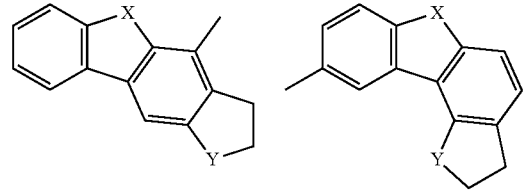

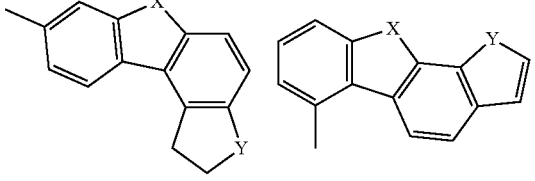

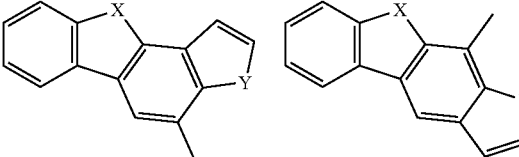

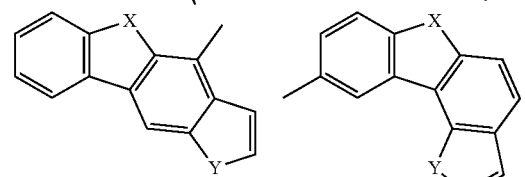

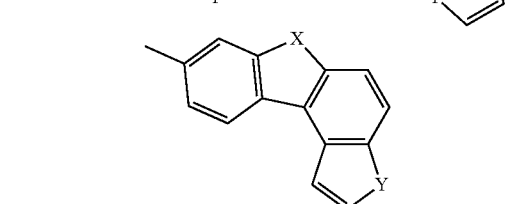

The optional substituent referred to by the term "substituted or unsubstituted" and the substituent referred to by the simple term "substituent" are preferably at least one selected from the group consisting of: an alkyl group having 1 to 50 (preferably 1 to 18, and more preferably 1 to 8) carbon atoms; a cycloalkyl group having 3 to 50 (preferably 3 to 10, more preferably 3 to 8, and still more preferably 5 or 6) ring carbon atoms; an aryl group having 6 to 50 (preferably 6 to 25, and more preferably 6 to 18) ring carbon atoms; an aralkyl group having 7 to 51 (preferably 7 to 30, and more preferably 7 to 20) carbon atoms which has an aryl group having 6 to 50 (preferably 6 to 25, and more preferably 6 to 18) ring carbon atoms; an amino group; a mono-substituted or di-substituted amino group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; an alkoxy group which has an alkyl group having 1 to 50 (preferably 1 to 18, and more preferably 1 to 8) carbon atoms; an aryloxy group which has an aryl group having 6 to 50 (preferably 6 to 25, and more preferably 6 to 18) ring carbon atoms; a mono-substituted, di-substituted or tri-substituted silyl group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; a heteroaryl group having 5 to 50 (preferably 5 to 24, and more preferably 5 to 13) ring atoms; a haloalkyl group having 1 to 50 (preferably 1 to 18, and more preferably 1 to 8) carbon atoms; a halogen atom (a fluorine atom, a chlorine atom, a bromine atom or an iodine atom); a cyano group; a nitro group; a sulfonyl group having a substituent selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; a di-substituted phosphoryl group having substituents selected from an alkyl group having 1 to 50 (preferably 1 to 18, and more preferably 1 to 8) carbon atoms and an aryl group having 6 to 50 (preferably 6 to 25, and more preferably 6 to 18) ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxy group; an alkyl-substituted or aryl-substituted carbonyl group; a carboxyl group; a vinyl group; a (meth)acryloyl group; an epoxy group; and an oxetanyl group.

These substituents may further have any of the optional substituents above. Also, the substituents may combine to form a ring.

Of the substituents, more preferable substituents are a substituted or unsubstituted alkyl group having 1 to 50 (preferably 1 to 18, and more preferably 1 to 8) carbon atoms, a substituted or unsubstituted cycloalkyl group having 3 to 50 (preferably 3 to 10, more preferably 3 to 8, and still more preferably 5 or 6) ring carbon atoms, a substituted or unsubstituted aryl group having 6 to 50 (preferably 6 to 25, and more preferably 6 to 18) ring carbon atoms, a mono-substituted or di-substituted amino group having a substituent selected from a substituted or unsubstituted alkyl group having 1 to 50 (preferably 1 to 18, and more preferably 1 to 8) carbon atoms and a substituted or unsubstituted aryl group having 6 to 50 (preferably 6 to 25, and more preferably 6 to 18) ring carbon atoms, a substituted or unsubstituted heteroaryl group having 5 to 50 (preferably 5 to 24, and more preferably 5 to 13) ring atoms, a halogen atom and a cyano group.

In the present specification, the preferable options can be selected optionally, and a combination of preferable options is considered to be more preferable.

[Compound]

The compound which is an aspect of the present invention and which is useful as a material for an organic electroluminescence device is represented by the following general formula (1).

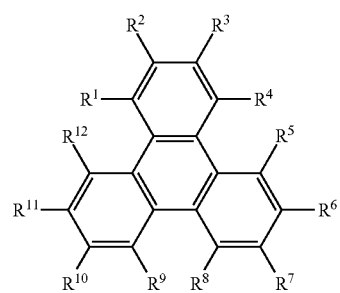

In the general formula (1), $R^1$ to $R^{12}$ are each independently a hydrogen atom or a substituent, and the substituents of at least a pair selected from $R^1$ and $R^2$, $R^2$ and $R^3$, $R^3$ and $R^4$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ may combine to form a ring, provided that at least one of $R^1$ to $R^{12}$ (including a group bonded to the ring when the substituents of the pair combine to form a ring) is a group represented by the following general formula (2):

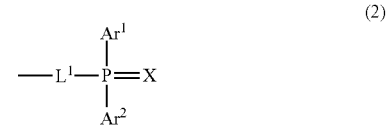

wherein in the general formula (2), X represents an oxygen atom, a sulfur atom or a selenium atom, $L^1$ is a direct bond, a substituted or unsubstituted arylene group having 6 to 60 ring carbon atoms or a substituted or unsubstituted heteroarylene group having 5 to 60 ring atoms, $Ar^1$ and $Ar^2$ are each independently a substituted or unsubstituted aryl group having 6 to 60 ring carbon atoms or a heteroaryl group having 5 to 60 ring atoms, and $Ar^1$ and $Ar^2$ may combine to form a ring.

As described above, in the general formula (1), $R^1$ to $R^{12}$, except for the group(s) represented by the general formula (2), are a hydrogen atom or a substituent but are preferably a hydrogen atom.

The ring structure which at least a pair selected from $R^1$ and $R^2$, $R^2$ and $R^3$, $R^3$ and $R^4$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ can form may be a ring in which a conjugated system is disconnected. However, from the viewpoint of allowing the organic EL device to exhibit a good driving voltage and a good external quantum efficiency and extend the lifetime, the ring is preferably a substituted or unsubstituted aromatic ring or a substituted or unsubstituted heteroaromatic ring, more preferably a substituted or unsubstituted aromatic ring, and still more preferably an unsubstituted aromatic ring. The aromatic ring is a benzene ring, a naphthalene ring, an anthracene ring, a phenanthrene ring or the like and is preferably a benzene ring.

When the aromatic ring is a benzene ring, the ring is considered to be a ring formed by the following partial structure:

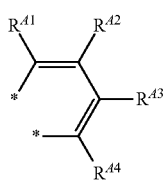

wherein $R^{41}$ to $R^{44}$ are each independently a hydrogen atom or a substituent, and * represents a binding site to a carbon atom.

As described above, any one of $R^1$ to $R^{12}$ (including a group bonded to the ring when the substituents of the pair combine to form a ring) is a group represented by the general formula (2). Here, the substituents of at least a pair selected from $R^1$ and $R^2$, $R^2$ and $R^3$, $R^3$ and $R^4$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ in $R^1$ to $R^{12}$ sometimes combine to form a ring as described above, and it is explained in the brackets that, in such a case, a group bonded to the formed ring may be a group represented by the general formula (2). That is, when the ring is not formed, any one of $R^1$ to $R^{12}$ is a group represented by the general formula (2): while when the ring is formed, for example when $R^1$ and $R^2$ combine to form the ring, a group represented by the general formula (2) is bonded to a carbon atom constituting the ring formed by combined $R^1$ and $R^2$ or any one of $R^3$ to $R^{12}$ is a group represented by the general formula (2).

X in the general formula (2) represents an oxygen atom, a sulfur atom or a selenium atom but is preferably an oxygen atom or a sulfur atom, and more preferably an oxygen atom.

$L^1$ is a direct bond, a substituted or unsubstituted arylene group having 6 to 60 ring carbon atoms or a substituted or unsubstituted heteroarylene group having 5 to 60 ring atoms.

From the viewpoint of allowing the organic EL device to exhibit a good driving voltage and a good external quantum efficiency and extend the lifetime, the number of the ring carbon atoms of the arylene group is preferably 6 to 40, more preferably 6 to 20, still more preferably 6 to 14, and particularly preferably 6 to 12. Examples of the arylene group include a phenylene group, a naphthylene group (1,4-naphthylene group, 1,5-naphthylene group or the like), an anthrylene group (9,10-anthrylene group or the like), a biphenylylene group, a terphenylylene group, a benzanthrylene group, a phenanthrylene group, a benzophenanthrylene group, a fluorenylene group (2,7-fluorenylene group or the like), a 9,9-di-substituted fluorenylene group (9,9-dimethyl-2,7-fluorenylene group, 9,9-diphenyl-2,7-fluorenylene group or the like), a benzofluorenylene group, a dibenzofluorenylene group, a picenylene group, a tetracenylene group, a pentacenylene group, a pyrenylene group, a chrysenylene group, a benzochrysenylene group, an s-indacenylene group, an as-indacenylene group, a fluoranthenylene group, a benzofluoranthenylene group, a perylenylene group, a coronenylene group, a dibenzanthracenylene group and the like. Of these examples, from the viewpoint of allowing the organic EL device to exhibit a good driving voltage and a good external quantum efficiency and extend the lifetime, a phenylene group, a biphenylylene group, a fluorenylene group, a 9,9-di-substituted fluorenylene group, a dibenzofuranylene group and a dibenzothiophenylene group are preferable. A phenylene group is more preferable, and 1,4-phenylene group is still more preferable.

From the viewpoint of allowing the organic EL device to exhibit a good driving voltage and a good external quantum efficiency and extend the lifetime, the number of the ring atoms of the heteroarylene group is preferably 5 to 40, more preferably 5 to 20, still more preferably 5 to 14, and particularly preferably 5 to 12. Examples of the heteroarylene group include divalent nitrogen-containing heterocyclic groups such as a pyrrolylene group, a pyridylene group (2,5-pyridylene group or the like), an imidazopyridylene group, a pyrazolylene group, a triazolylene group, a tetrazolylene group, an indolylene group, an isoindolylene group and a carbazolylene group [a 9-substituted-3,6-carbazolylene group or the like, wherein the substituent at 9-position is an alkyl group having 1 to 10 (preferably 1 to 6) carbon atoms, an aryl group having 6 to 30 (preferably 6 to 14) ring carbon atoms or a heteroaryl group having 5 to 30 (preferably 5 to 14) ring atoms]; divalent oxygen-containing heterocyclic groups such as a furanylene group, a benzofuranylene group, an isobenzofuranylene group, a dibenzofuranylene group (2,8-dibenzofuranylene group or the like), an oxazolylene group, an oxadiazolylene group, a benzoxazolylene group, a benzonaphthofuranylene group and a dinaphthofuranylene group; and divalent sulfur-containing heterocyclic groups such as a thiophenylene group, a benzothiophenylene group, a dibenzothiophenylene group (2,8-dibenzothiophenylene group or the like), a thiazolylene group, a thiadiazolylene group, a benzothiazolylene group, a benzonaphthothiophenylene group and a dinaphthothiophenylene group.

The "direct bond" is sometimes generally referred to as a "single bond" as another term.

Of these, from the viewpoint of allowing the organic EL device to exhibit a good driving voltage and a good external quantum efficiency and extend the lifetime, $L^1$ is preferably a direct bond or a substituted or unsubstituted arylene group having 6 to 60 ring carbon atoms, and more preferably a substituted or unsubstituted arylene group having 6 to 60 ring carbon atoms.

$Ar^1$ and $Ar^2$ in the general formula (2) are each independently a substituted or unsubstituted aryl group having 6 to 60 ring carbon atoms or a heteroaryl group having 5 to 60 ring atoms, and $Ar^1$ and $Ar^2$ may combine to form a ring.

From the viewpoint of allowing the organic EL device to exhibit a good driving voltage and a good external quantum efficiency and extend the lifetime, the number of the ring carbon atoms of the aryl group is preferably 6 to 40, more preferably 6 to 20, still more preferably 6 to 14, and particularly preferably 6 to 12. Examples of the aryl group include a phenyl group, a naphthyl group (1-naphthyl group or 2-naphthyl group), an anthryl group (1-anthryl group, 2-anthryl group or the like), a benzanthryl group, a phenanthryl group (1-phenanthryl group, 2-phenanthryl group, 3-phenanthryl group, 9-phenanthryl group or the like), a benzophenanthryl group, a fluorenyl group, a 9,9-di-substituted fluorenyl group (9,9-dimethyl-2-fluorenyl group, 9,9-diphenyl-2-fluorenyl group or the like), a benzofluorenyl group, a dibenzofluorenyl group, a picenyl group, a tetracenyl group, a pentacenyl group, a pyrenyl group, a chrysenyl group, a benzochrysenyl group, an s-indacenyl group, an as-indacenyl group, a fluoranthenyl group, a benzofluoranthenyl group, a triphenylenyl group, a benzotriphenylenyl group, a perylenyl group, a coronenyl group, a dibenzanthryl group and the like. Of these examples, from the viewpoint of allowing the organic EL device to exhibit a good driving voltage and a good external quantum efficiency and extend the lifetime, a phenyl group and a naphthyl group are preferable, and a phenyl group is more preferable.

From the viewpoint of allowing the organic EL device to exhibit a good driving voltage and a good external quantum efficiency and extend the lifetime, the number of the ring atoms of the heteroaryl group is preferably 5 to 40, more preferably 5 to 20, still more preferably 5 to 14, and particularly preferably 5 to 12. Examples of the heteroaryl group include monovalent nitrogen-containing heterocyclic groups such as a pyrrolyl group, a pyridyl group (2-pyridyl group or the like), an imidazopyridyl group, a bipyridyl group, a pyrazolyl group, a triazolyl group, a tetrazolyl group, an indolyl group, an isoindolyl group, a phenanthrolyl group and a carbazolyl group [a 9-substituted-3-carbazolyl group or the like, wherein the substituent at 9-position is an alkyl group having 1 to 10 (preferably 1 to 6) carbon atoms, an aryl group having 6 to 30 (preferably 6 to 14) ring carbon atoms or a heteroaryl group having 5 to 30 (preferably 5 to 14) ring atoms]; monovalent oxygen-containing heterocyclic groups such as a furanyl group, a benzofuranyl group, an isobenzofuranyl group, a dibenzofuranyl group (2-dibenzofuranyl group or the like), an oxazolyl group, an oxadiazolyl group, a benzoxazolyl group, a benzonaphthofuranyl group and a dinaphthofuranyl group; and monovalent sulfur-containing heterocyclic groups such as a benzothiophenyl group, a dibenzothiophenyl group (2-dibenzothiophenyl group or the like), a thiophenyl group, a thiazolyl group, a thiadiazolyl group, a benzothiazolyl group, a benzonaphthothiophenyl group and a dinaphthothiophenyl group.

When $Ar^1$ and $Ar^2$ combine to form a ring, the general formula (2) is for example the following structure or the like.

[Chem. 10]

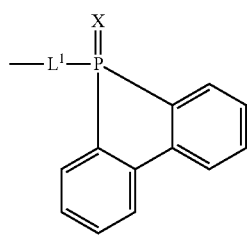

In the compound which is an aspect of the present invention, from the viewpoint of allowing the organic EL device to exhibit a good driving voltage and a good external quantum efficiency and extend the lifetime, it is preferable that at least one of $Ar^1$ and $Ar^2$ is a substituted or unsubstituted aryl group having 6 to 60 ring carbon atoms, and it is more preferable that $Ar^1$ and $Ar^2$ are both a substituted or unsubstituted aryl group having 6 to 60 ring carbon atoms. It is still more preferable that $Ar^1$ and $Ar^2$ are both a substituted or unsubstituted aryl group having 6 to 13 ring carbon atoms, and it is particularly preferable that $Ar^1$ and $Ar^2$ are each independently a substituted or unsubstituted phenyl group, a substituted or unsubstituted naphthyl group, a substituted or unsubstituted biphenylyl group or a substituted or unsubstituted fluorenyl group.

As the compound which is an aspect of the present invention, from the viewpoint of allowing the organic EL device to exhibit a good driving voltage and a good external quantum efficiency and extend the lifetime, a compound in which "one" of $R^1$ to $R^{12}$ (including a group bonded to the ring when the substituents of the pair combine to form a ring) is a group represented by the general formula (2) is preferable. Among these, from the viewpoint of allowing the organic EL device to exhibit a good driving voltage and a good external quantum efficiency and extend the lifetime, a compound represented by the following general formula (1-i) or the following general formula (1-ii) is preferable.

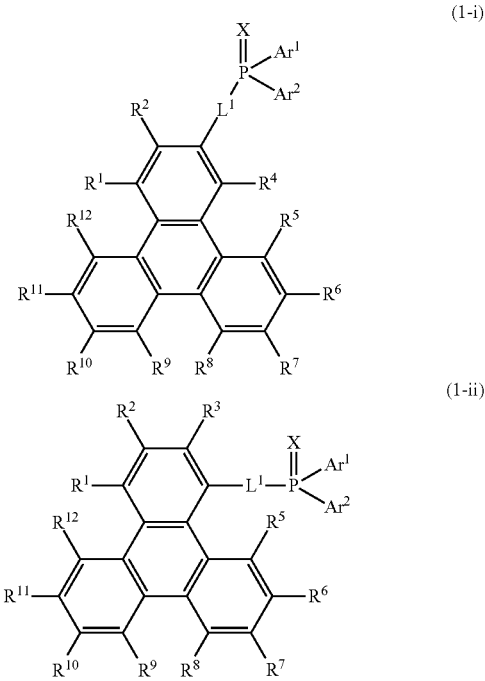

In the general formulae (1-i) and (1-ii), $R^1$ to $R^{12}$ are a hydrogen atom or a substituent. The substituents of at least a pair selected from $R^1$ and $R^2$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ in the general formula (1-i) may combine to form a ring, and the substituents of at least a pair selected from $R^1$ and $R^2$, $R^2$ and $R^3$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ in the general formula (1-ii) may combine to form a ring.

X, $L^1$, $Ar^1$ and $Ar^2$ are as defined above, and the preferable options are also the same.

As the compound which is an aspect of the present invention, from the viewpoint of allowing the organic EL device to exhibit a good driving voltage and a good external quantum efficiency and extend the lifetime, a compound represented by the following general formula (1-1) or the general formula (1-2) is also preferable, and a compound represented by the following general formula (1-1) is more preferable.

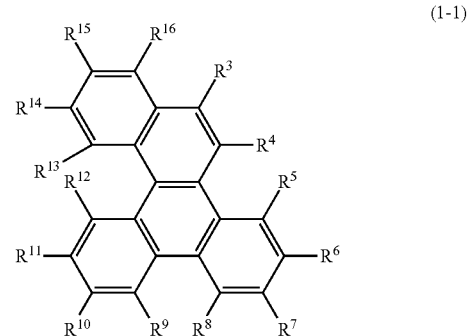

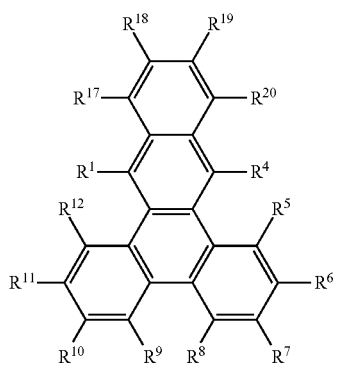

(1-2)

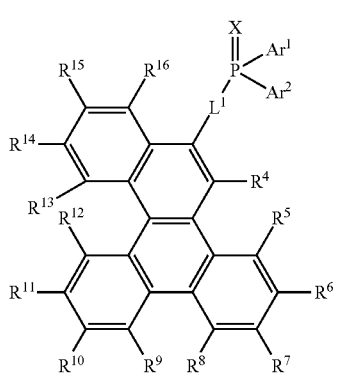

(1-1')

In the general formula (1-1), at least one of $R^3$ to $R^{16}$ is a group represented by the general formula (2), and the others are each independently a hydrogen atom or a substituent.

In the general formula (1-2), at least one of $R^1$ and $R^4$ to $R^{20}$ is a group represented by the general formula (2), and the others are each independently a hydrogen atom or a substituent.

In the general formula (1-1), from the viewpoint of allowing the organic EL device to exhibit a good driving voltage and a good external quantum efficiency and extend the lifetime, it is preferable that "one" of $R^3$ to $R^{16}$ is a group represented by the general formula (2). In the general formula (1-2), from the viewpoint of allowing the organic EL device to exhibit a good driving voltage and a good external quantum efficiency and extend the lifetime, it is preferable that "one" of $R^1$ and $R^4$ to $R^{20}$ is a group represented by the general formula (2). Of these compounds, from the viewpoint of allowing the organic EL device to exhibit a good driving voltage and a good external quantum efficiency and extend the lifetime, a compound represented by the following general formula (1-1') or the general formula (1-2') is more preferable.

(1-2')

In the general formulae (1-1') and (1-2'), $R^1$ and $R^4$ to $R^{20}$ are each independently a hydrogen atom or a substituent. X, $L^1$, $Ar^1$ and $Ar^2$ are as defined above, and the preferable options are also the same.

The substituents of at least a pair selected from $R^5$ and $R^6$, $R^6$ and $R^7$, $R^7$ and $R^8$, $R^9$ and $R^{10}$, $R^{10}$ and $R^{11}$, $R^{11}$ and $R^{12}$, $R^{13}$ and $R^{14}$, $R^{14}$ and $R^{15}$ and $R^{15}$ and $R^{16}$ in the general formula (1-1') may combine to form a ring, and the substituents of at least a pair selected from $R^1$ and $R^{17}$, $R^{17}$ and $R^{18}$, $R^{18}$ and $R^{91}$, $R^{19}$ and $R^{20}$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ in the general formula (1-2') may combine to form a ring.

A compound in which $R^1$ and $R^4$ to $R^{20}$ in the general formulae (1-1') and (1-2') are all independent from each other and do not combine to form a ring is preferable.

As the compound represented by the general formula (1-1'), a compound represented by the following general formula (1-1") is preferable from the viewpoint of allowing the organic EL device to exhibit a good driving voltage and a good external quantum efficiency and extend the lifetime. Also, as the compound represented by the general formula (1-2'), a compound represented by the following general formula (1-2") is preferable from the viewpoint of allowing the organic EL device to exhibit a good driving voltage and a good external quantum efficiency and extend the lifetime.

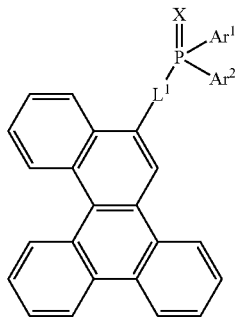

(1-1")

(1-2″)
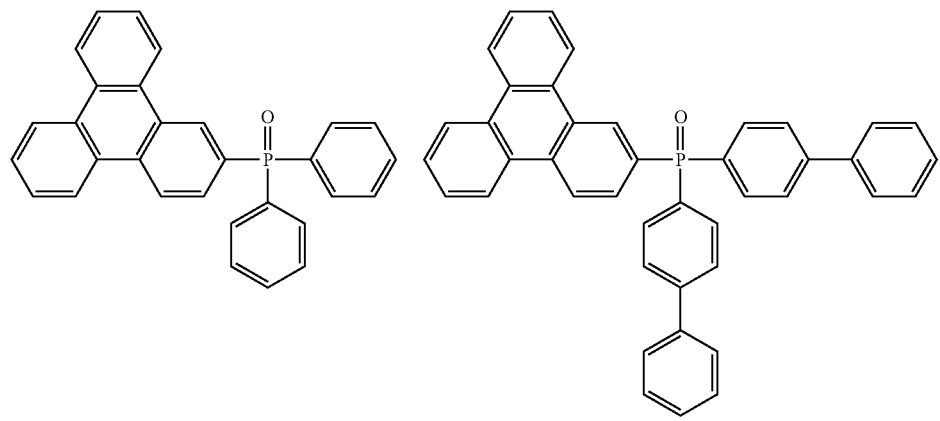
In the general formulae (1-1″) and (1-2″), X, $L^1$, $Ar^1$ and $Ar^2$ are as defined above, and the preferable options are also the same.
Specific examples of the compound which is an aspect of the present invention are the following compounds, although the compound is not particularly limited to the examples.
[Chem. 15]
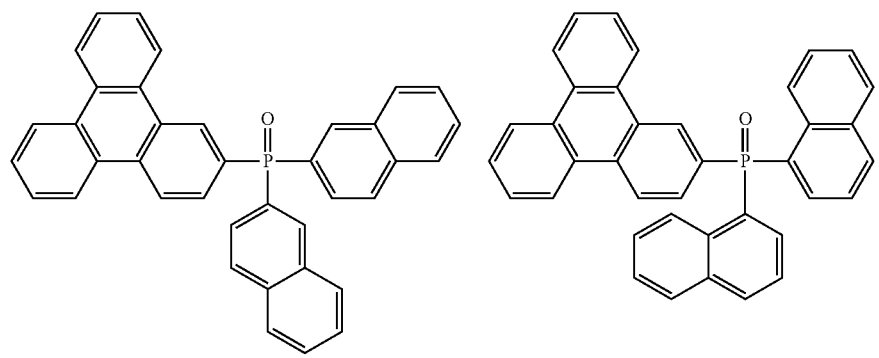
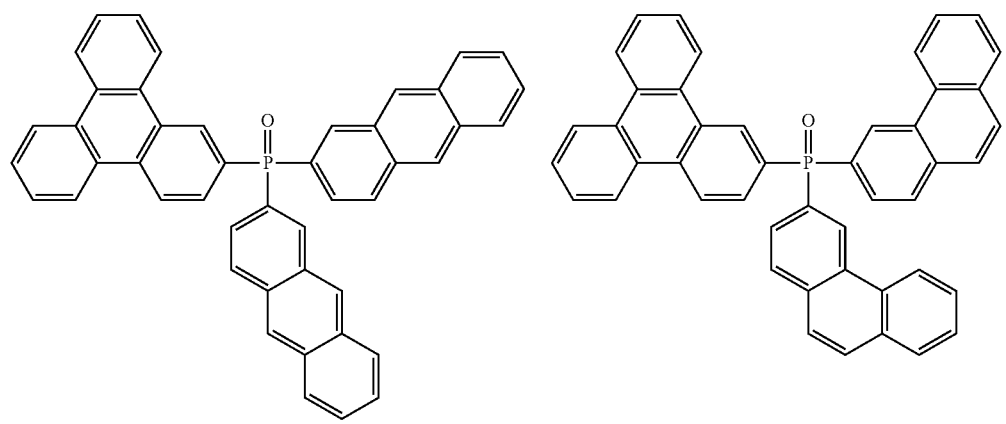

-continued
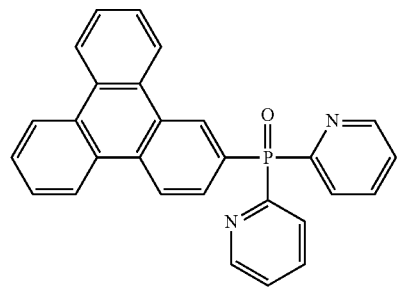
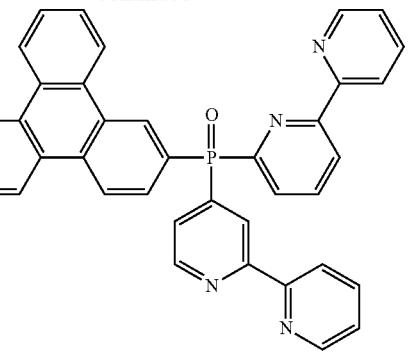
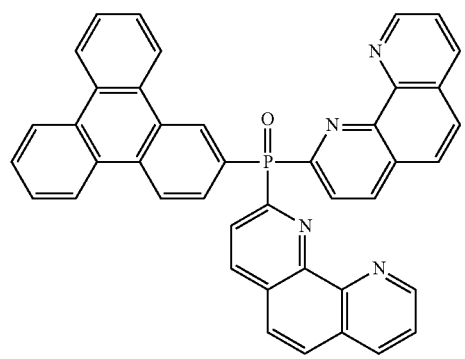
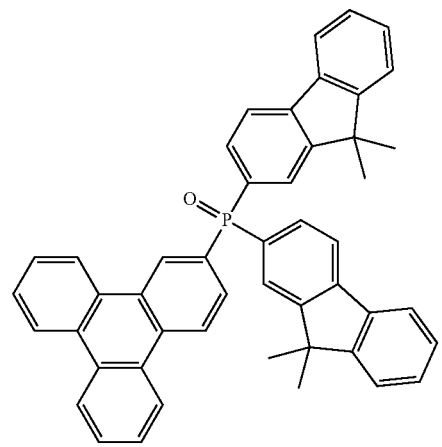
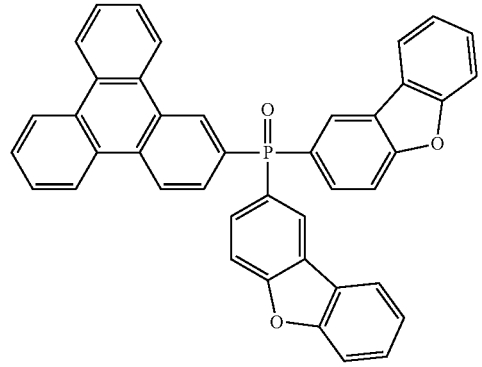
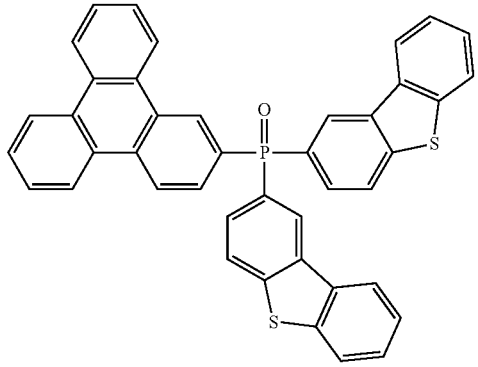
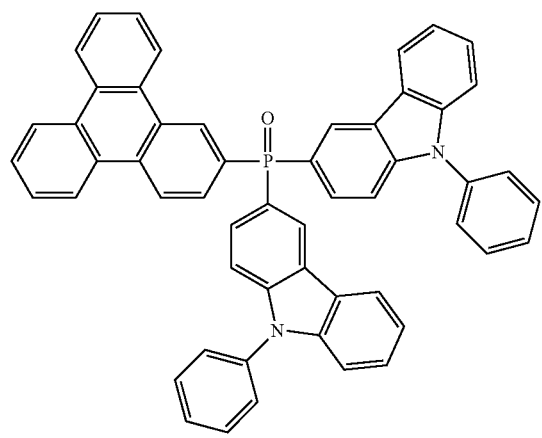
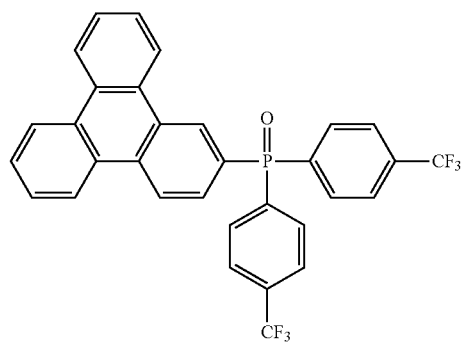

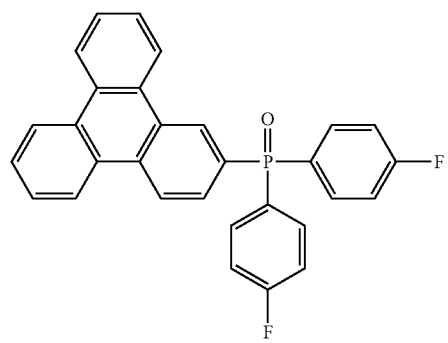
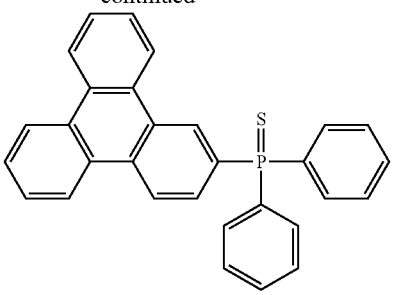
-continued
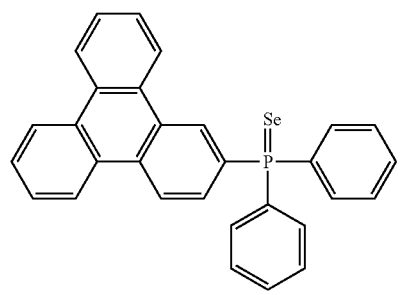
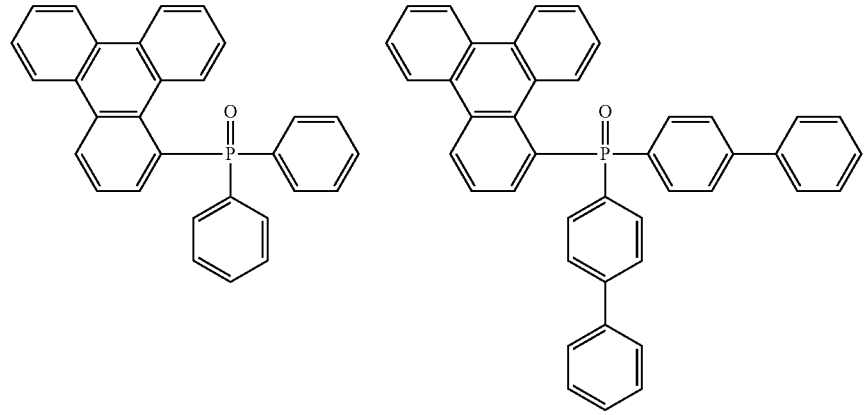
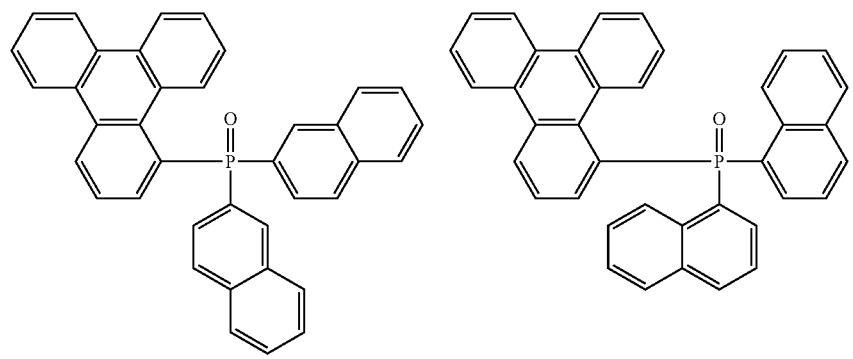
[Chem. 16]

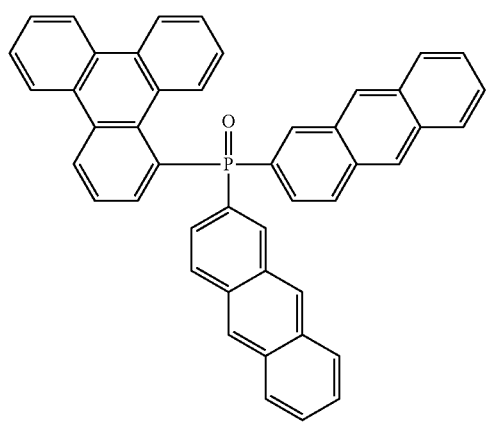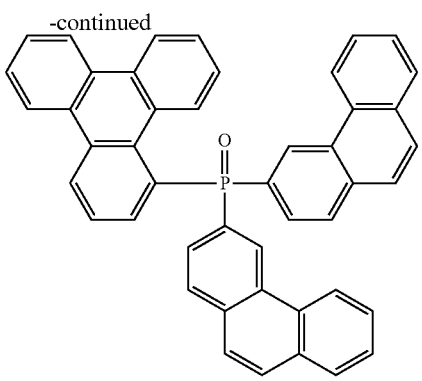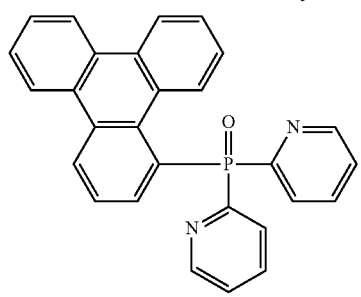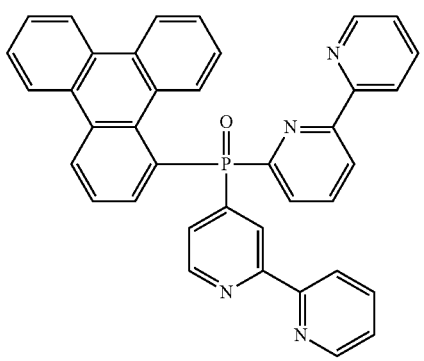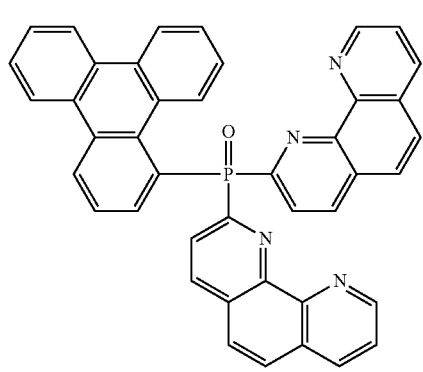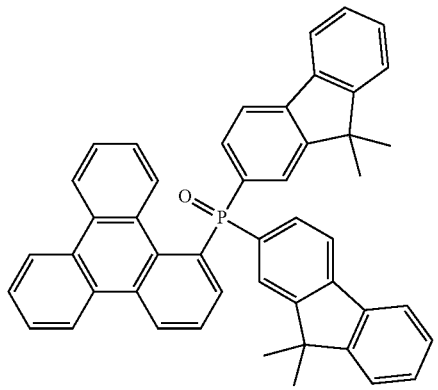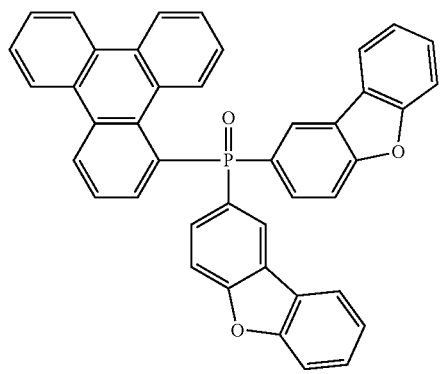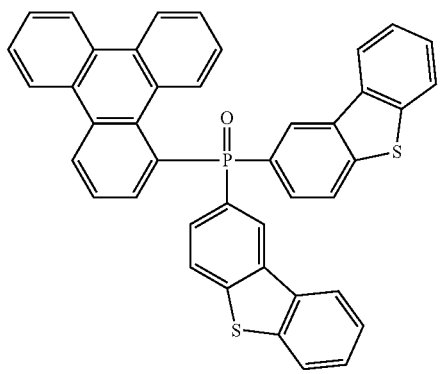

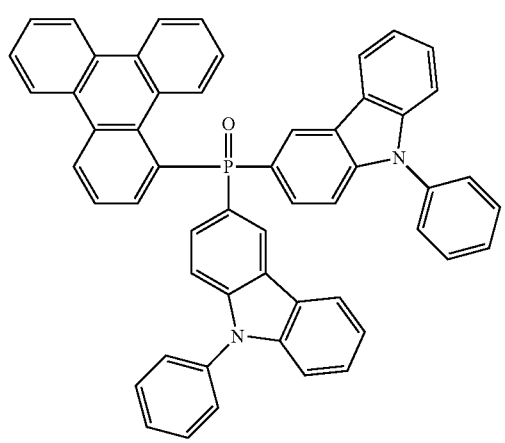
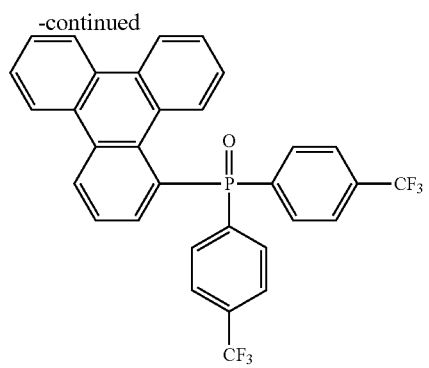
-continued
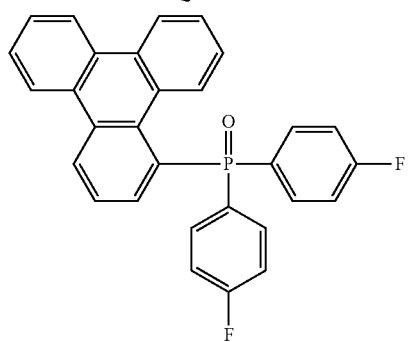
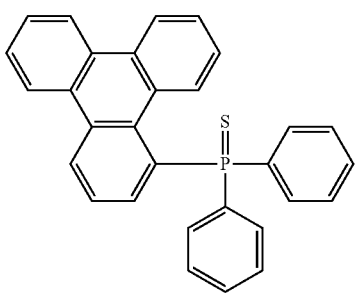
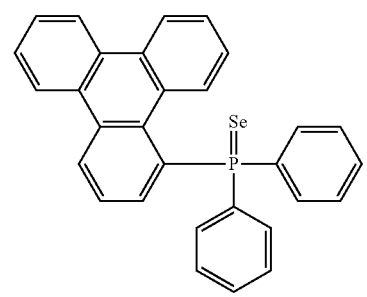
[Chem. 17]
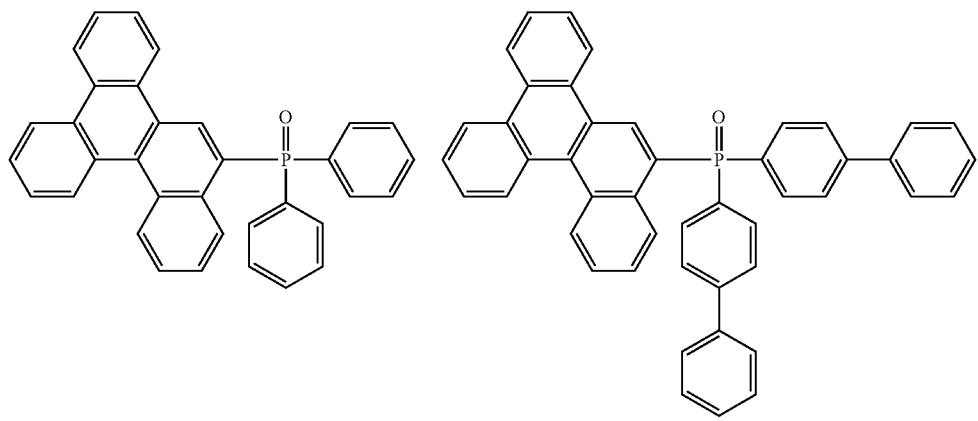
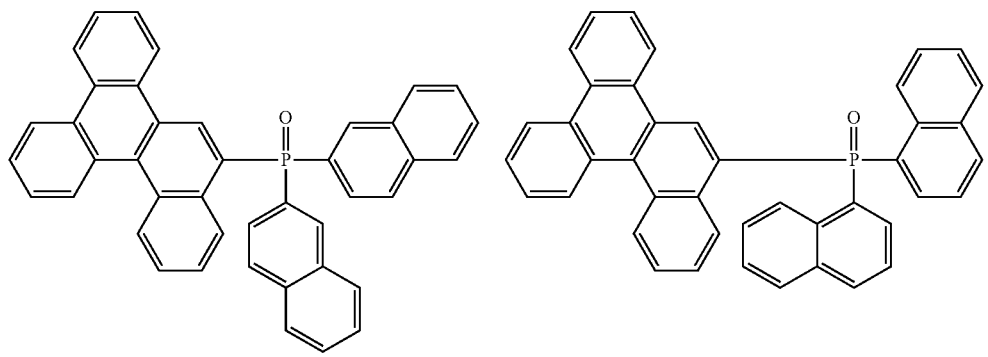

-continued
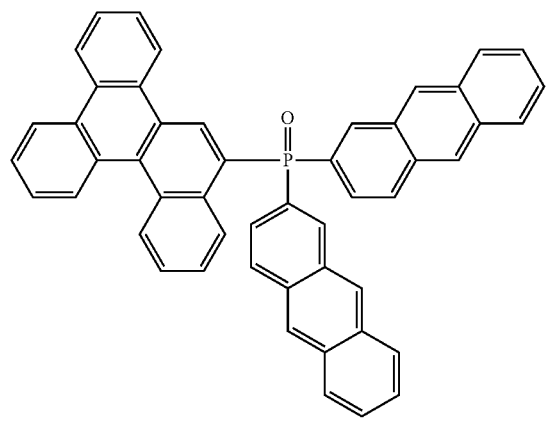
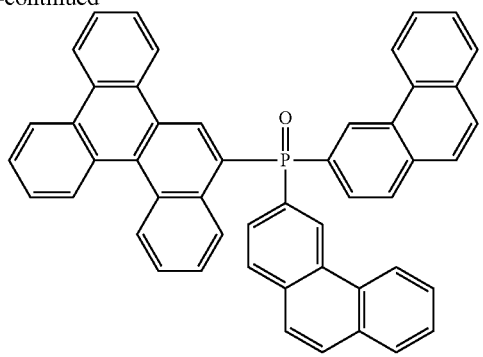
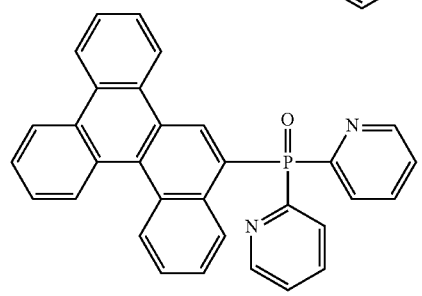
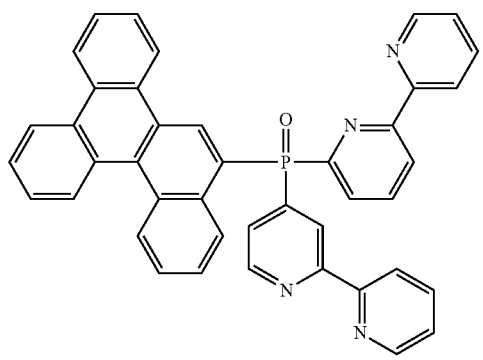
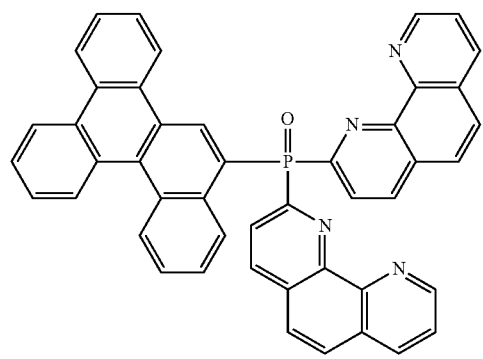
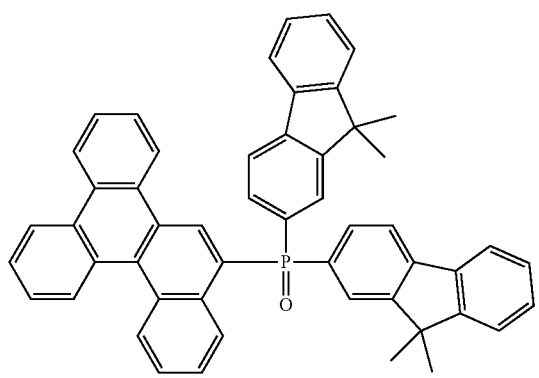
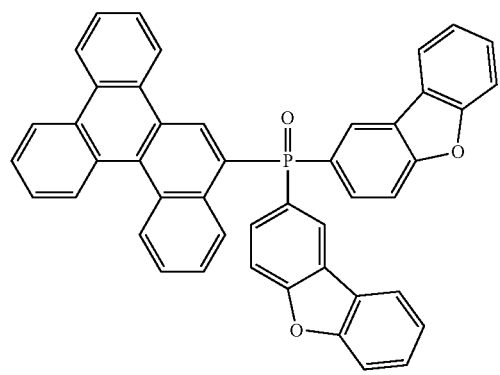
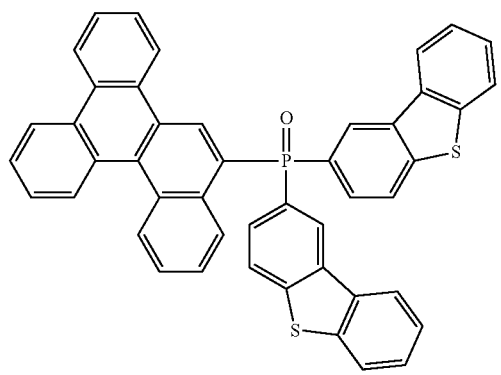

-continued
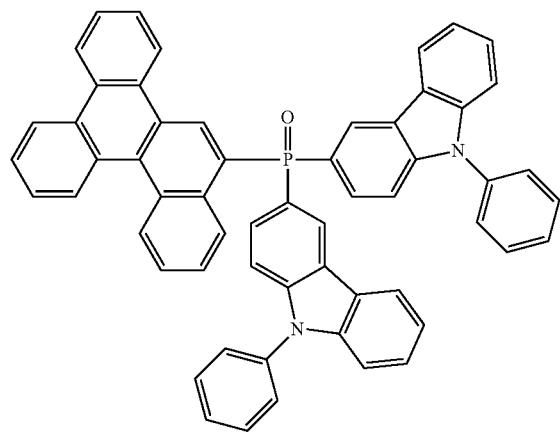
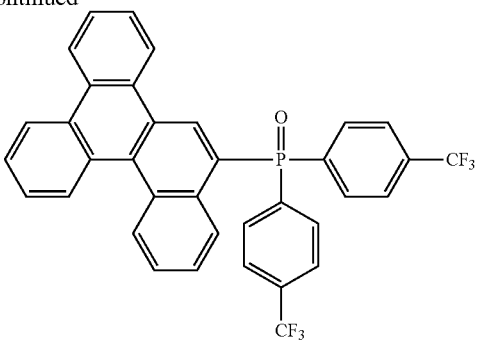
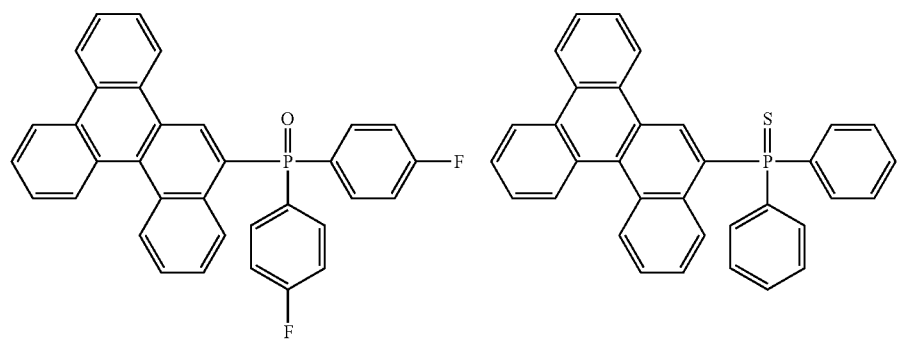
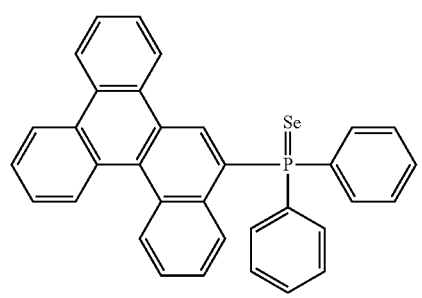
[Chem. 18]
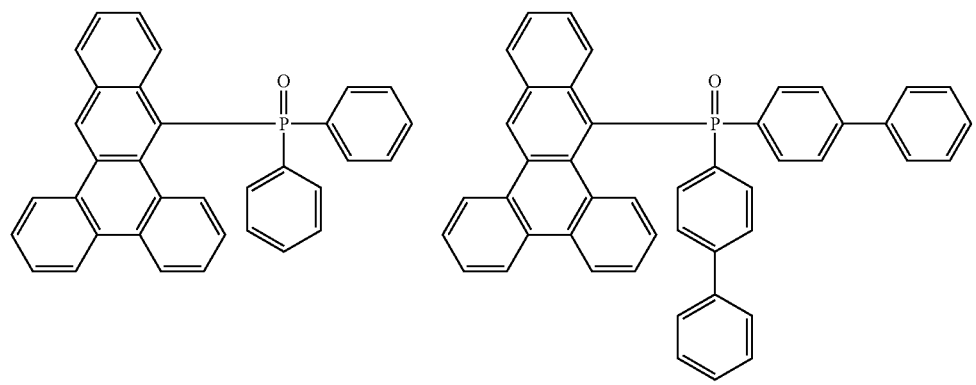

-continued
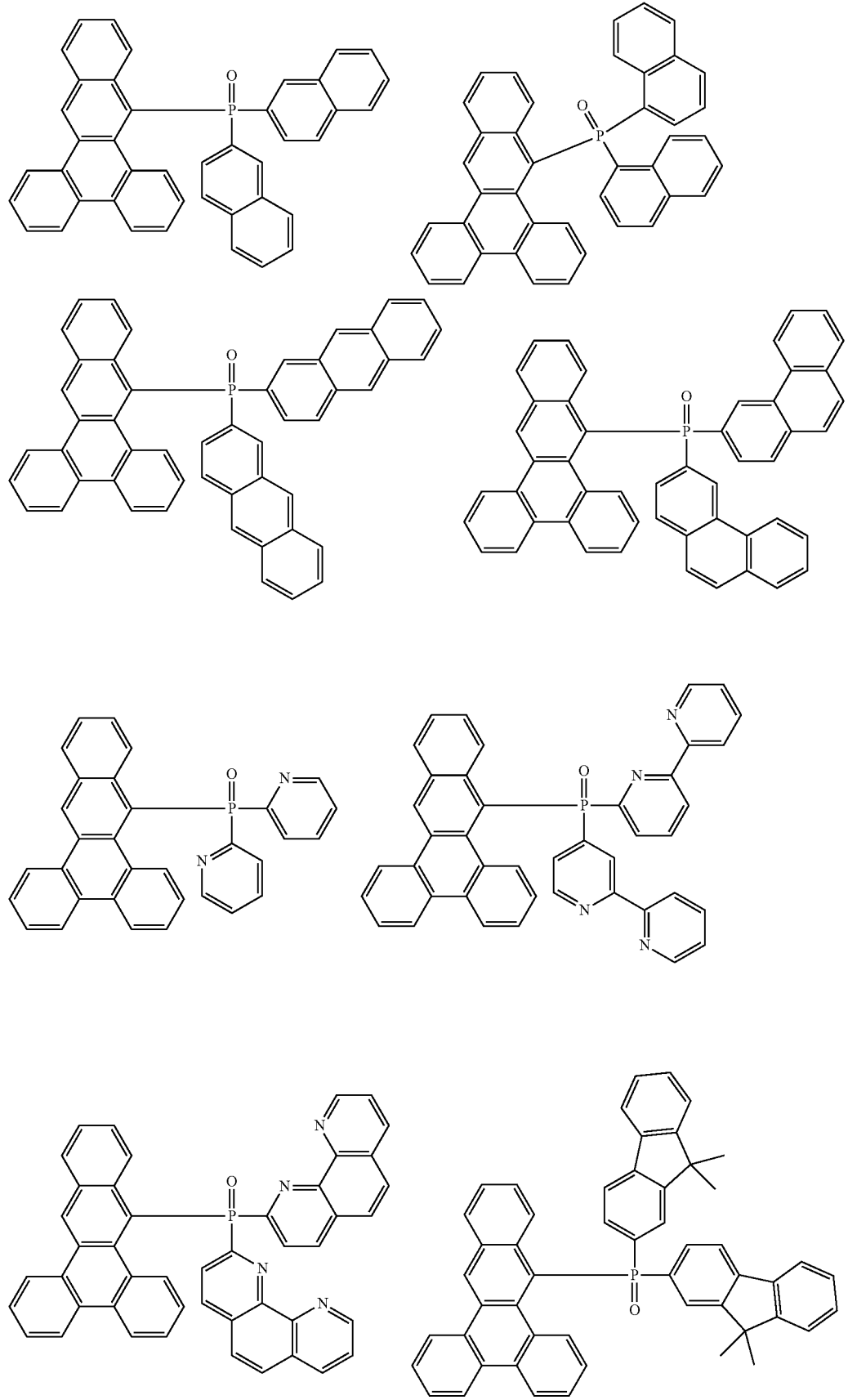

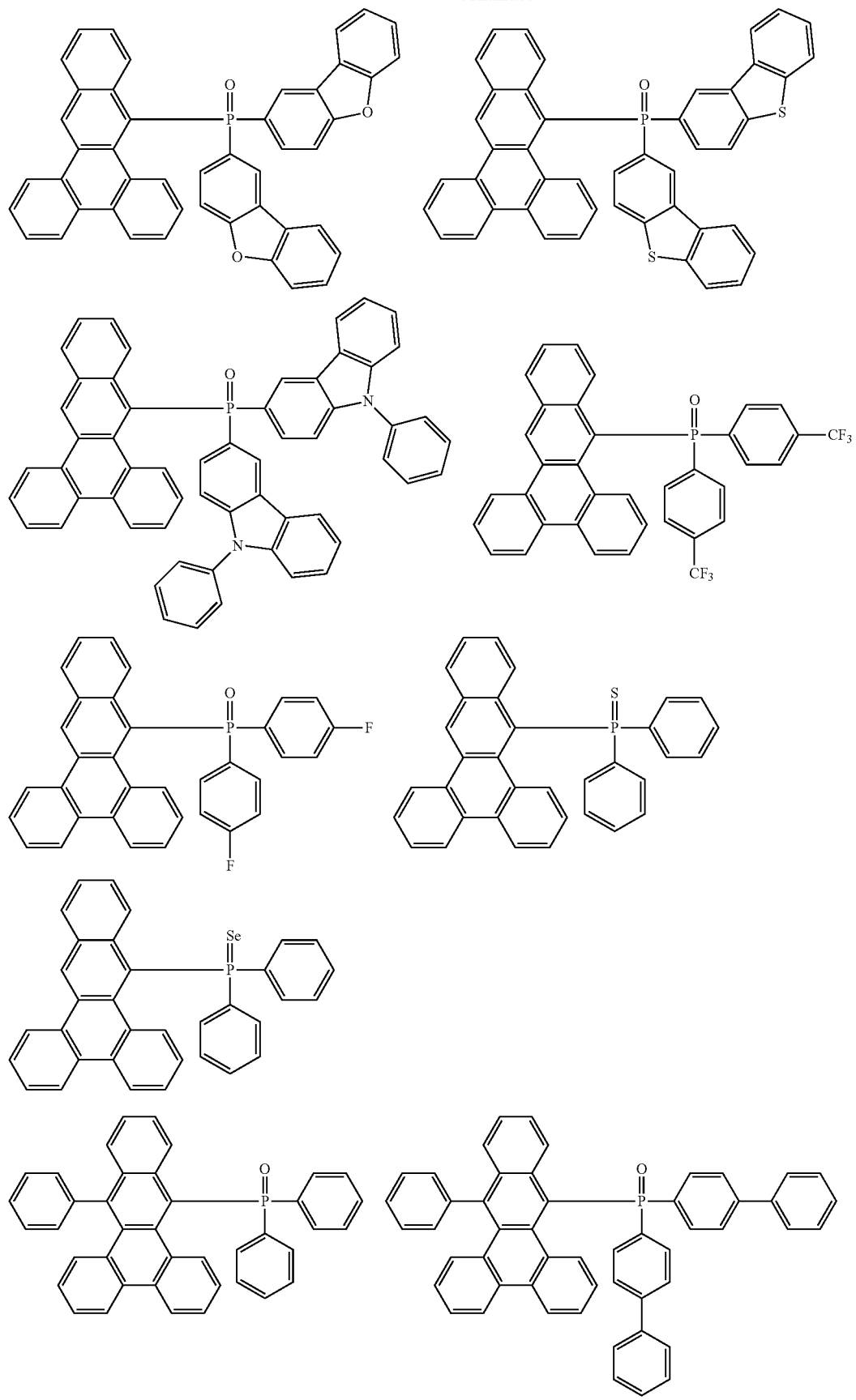
-continued
[Chem. 19]

33
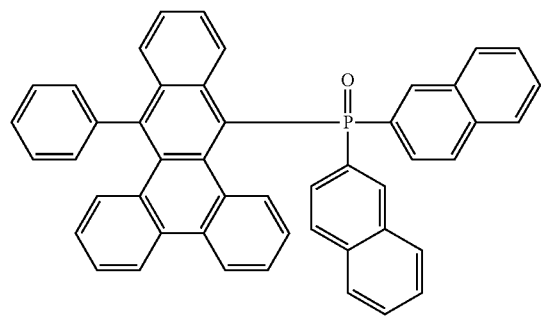
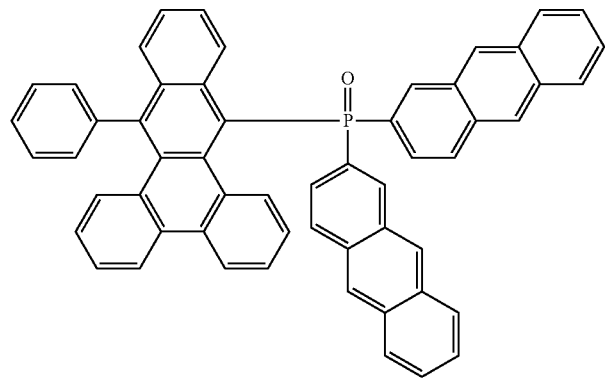
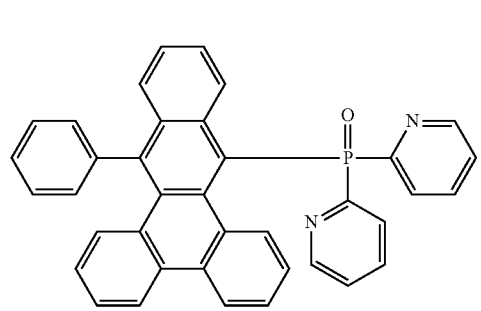
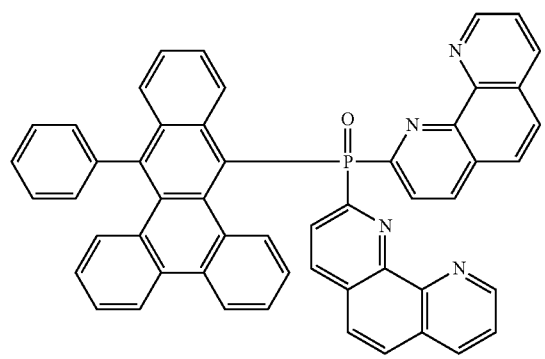
34
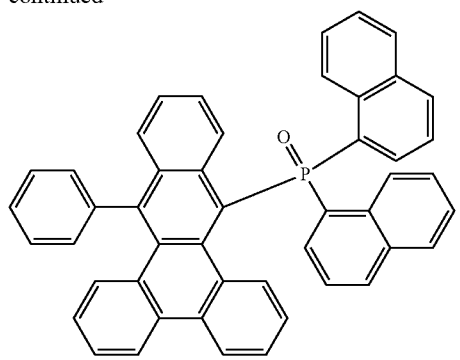
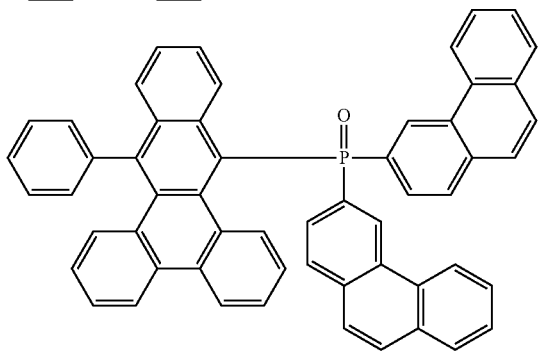
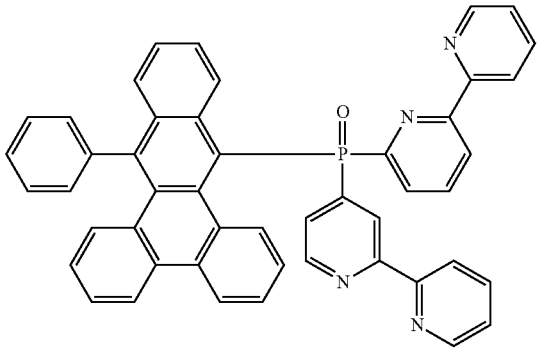
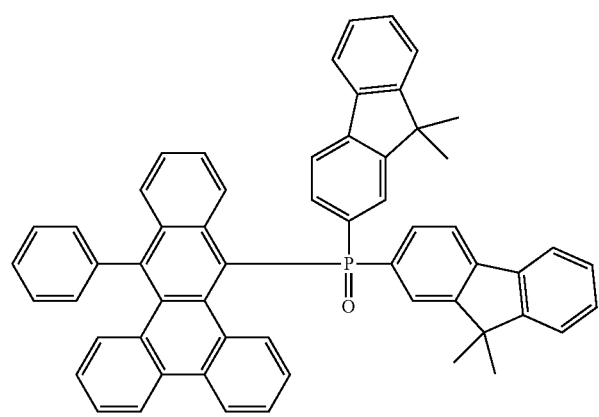

-continued
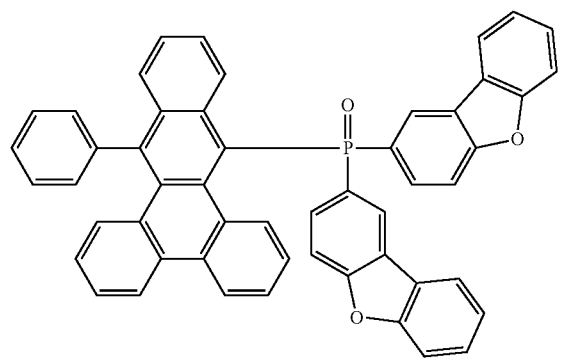
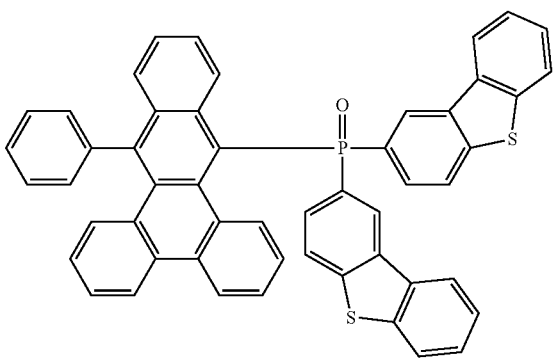
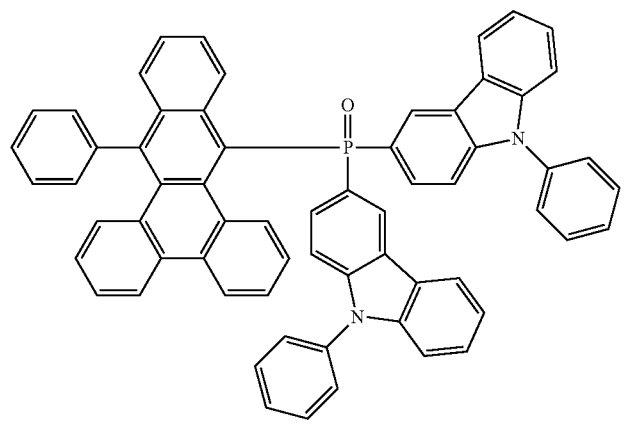
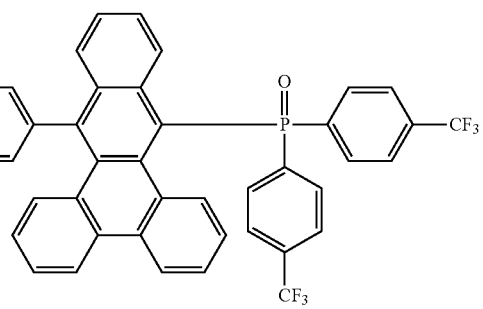
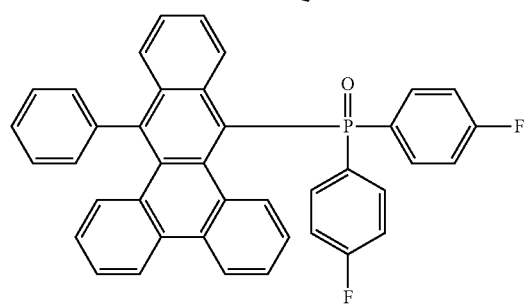
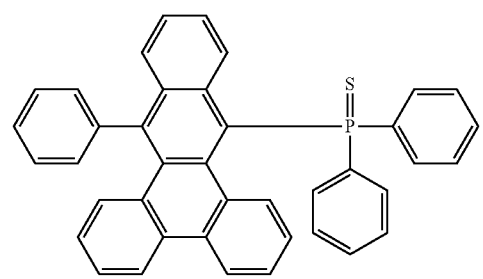
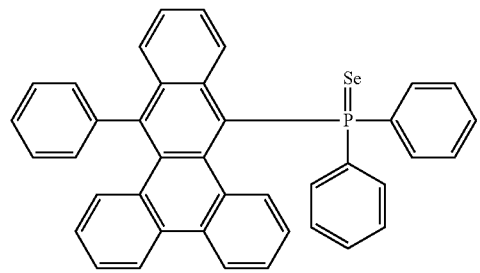
[Chem. 20]
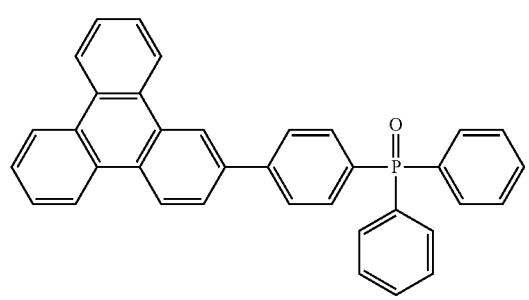
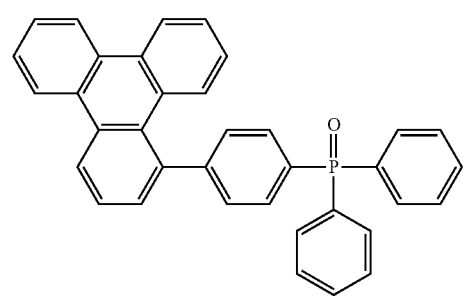

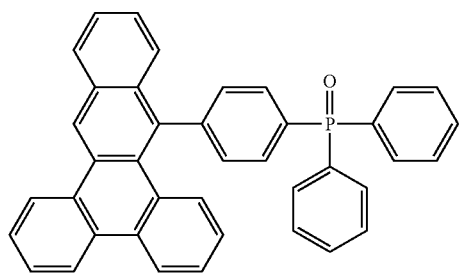
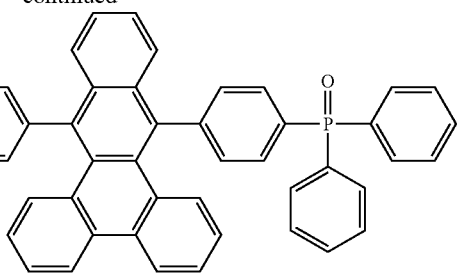
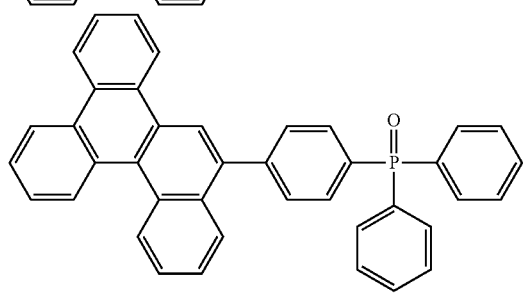
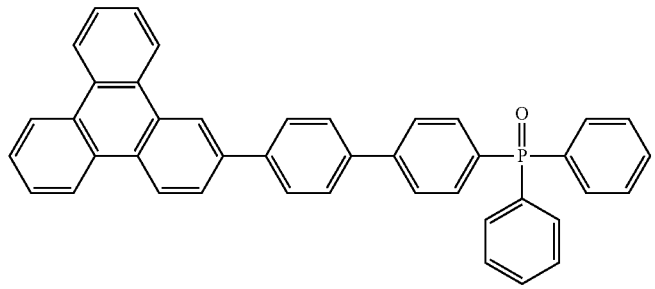
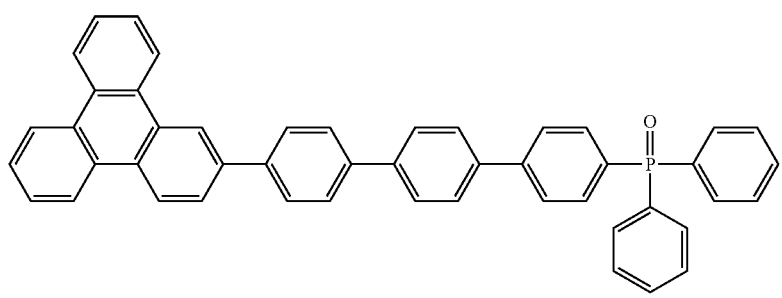
[Chem. 21]
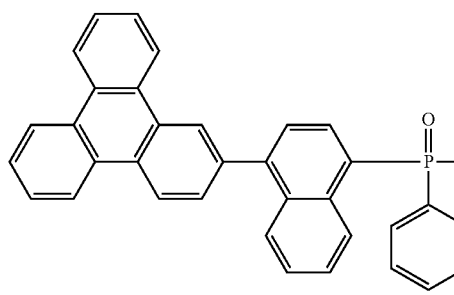
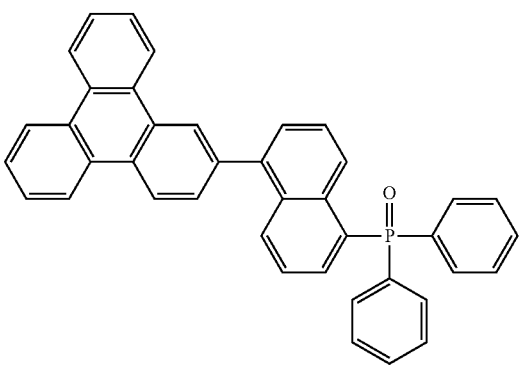

-continued
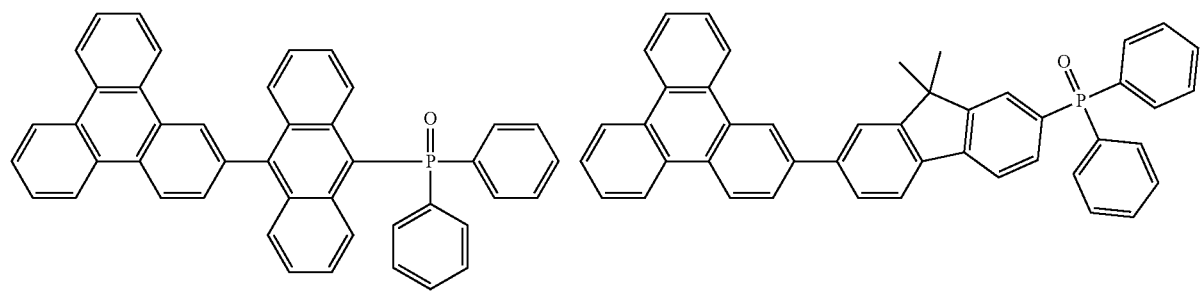
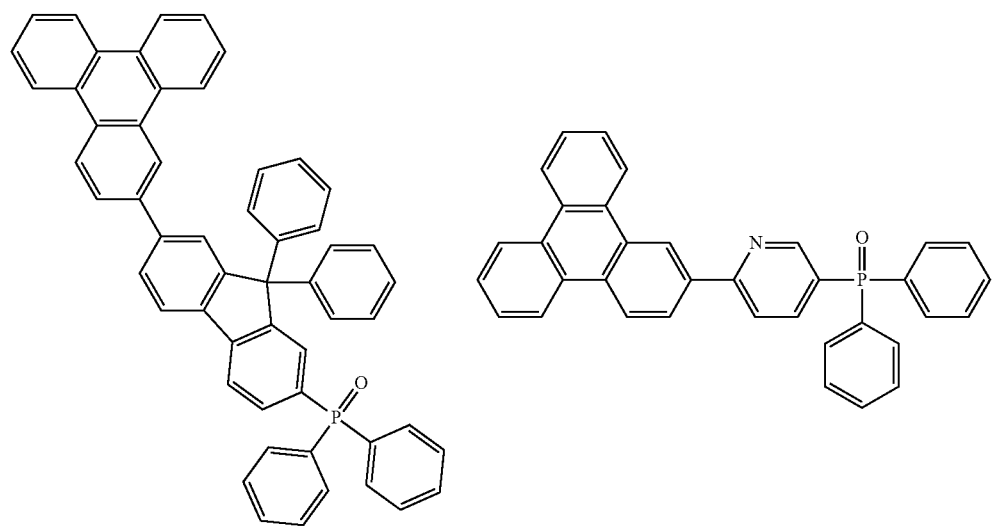
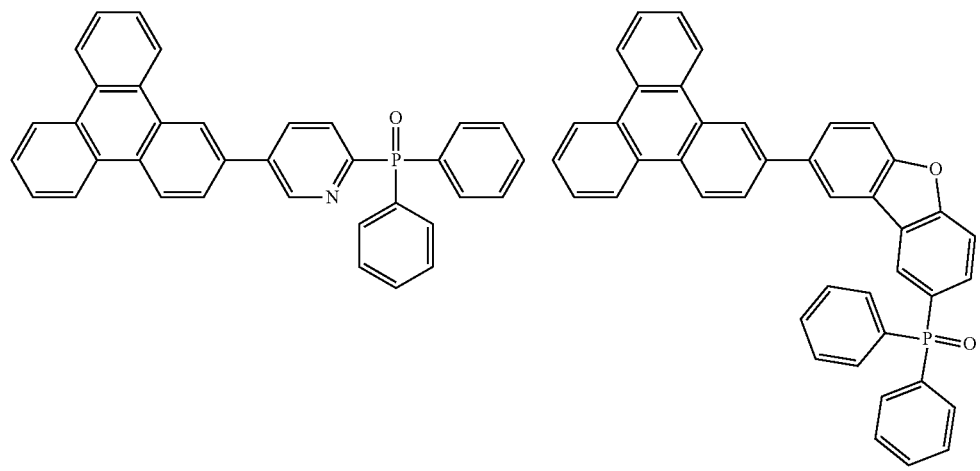

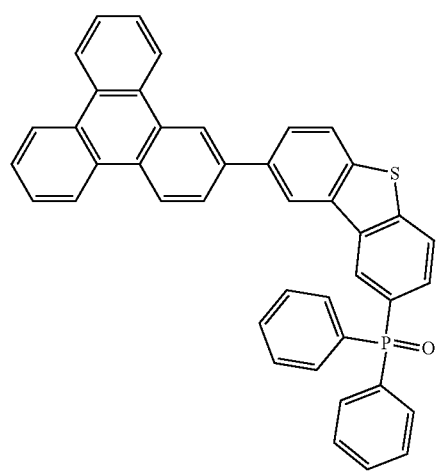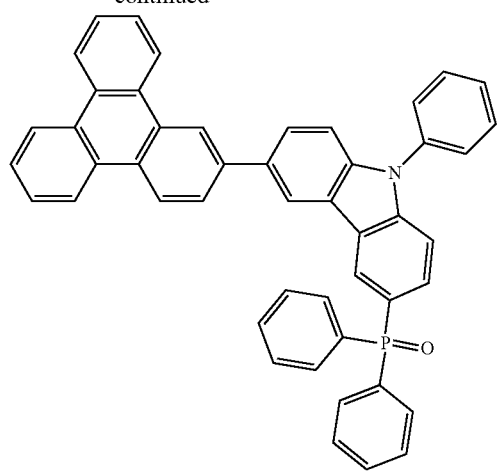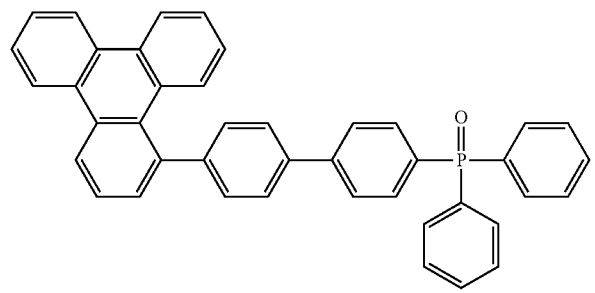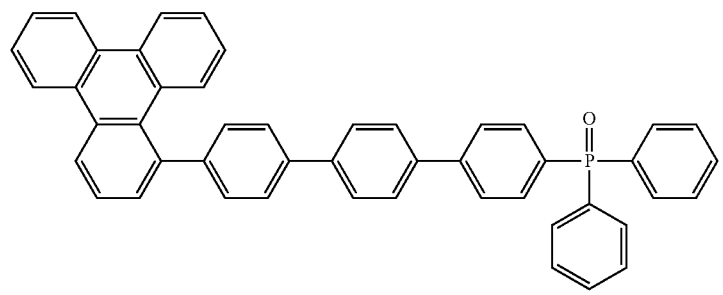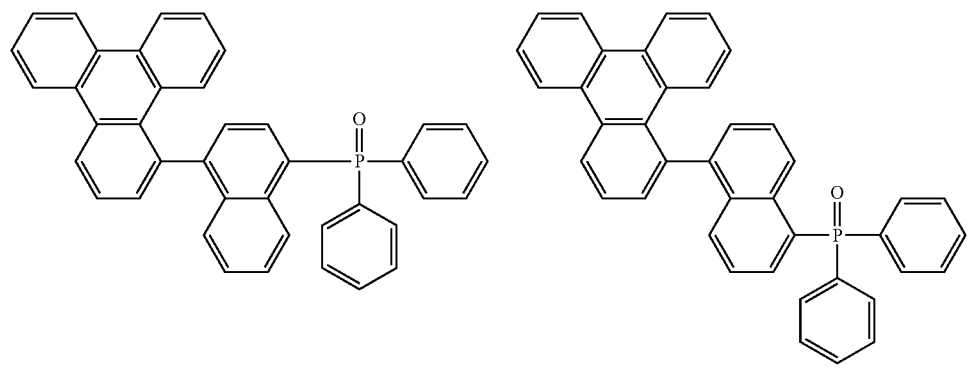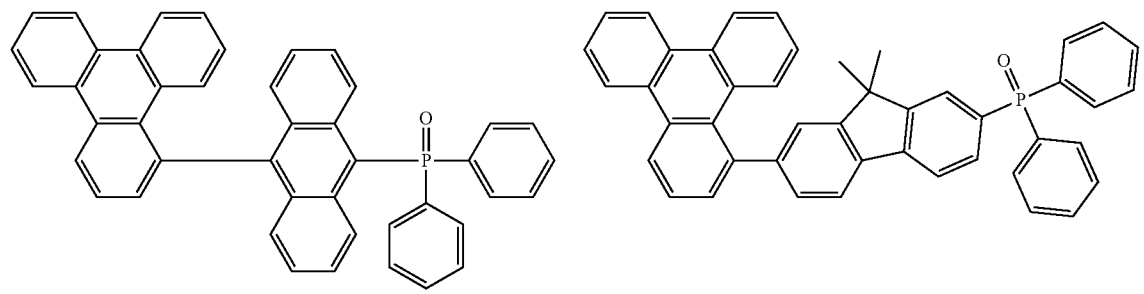

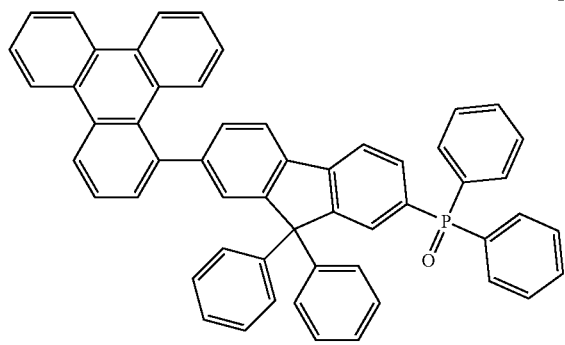
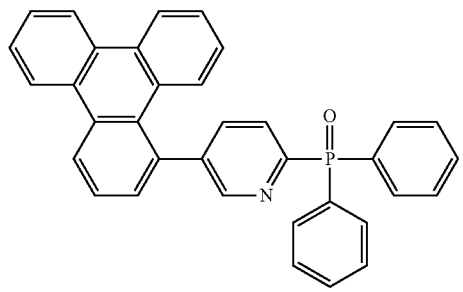
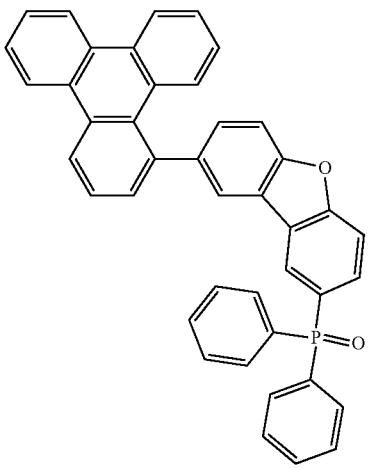
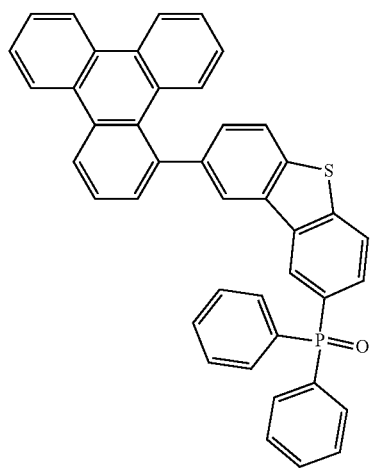
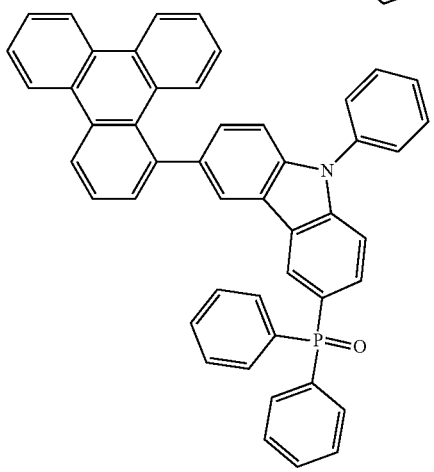
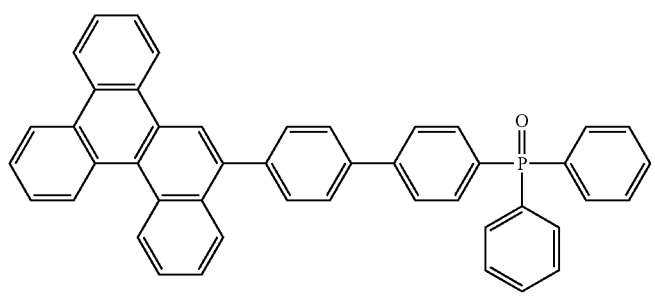
[Chem. 22]

-continued
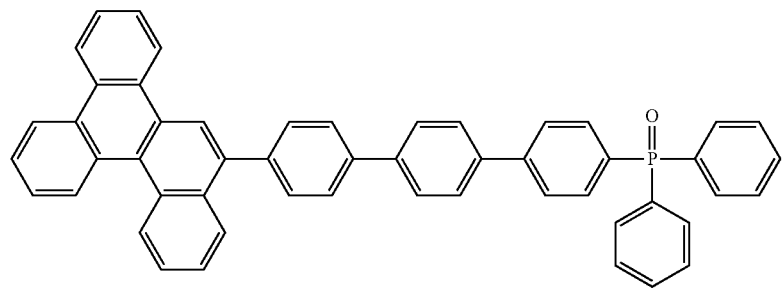
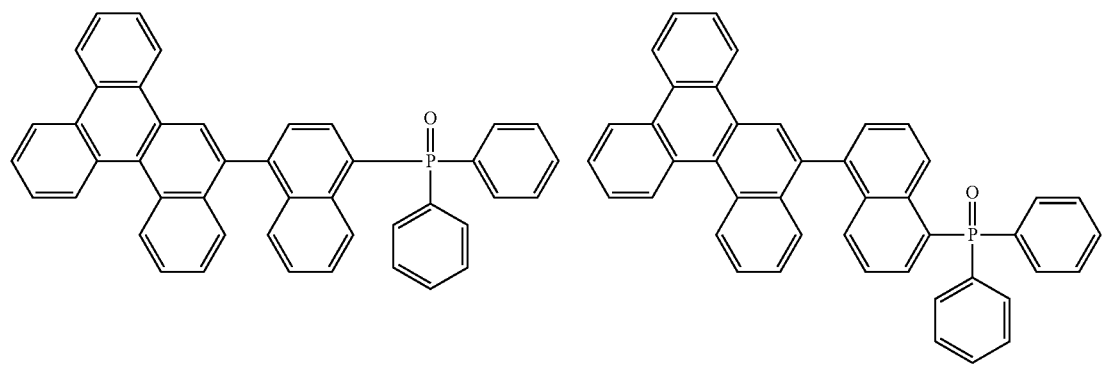
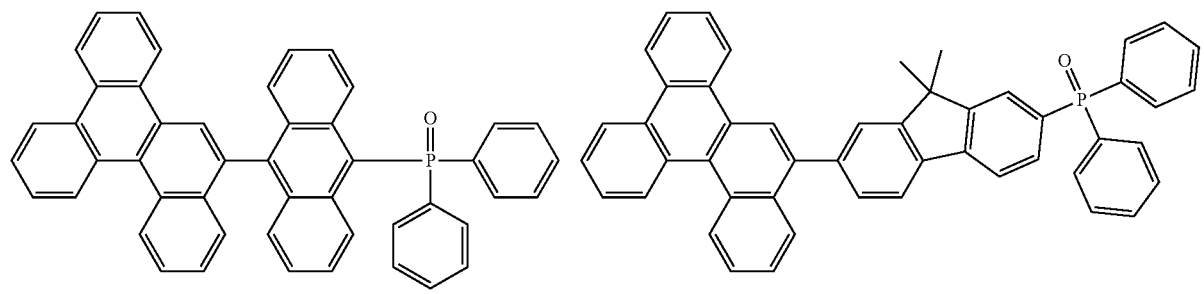
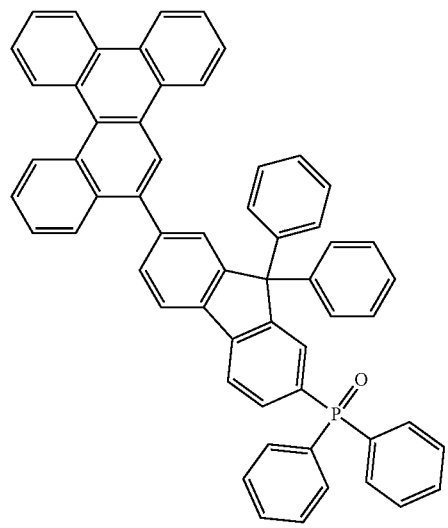
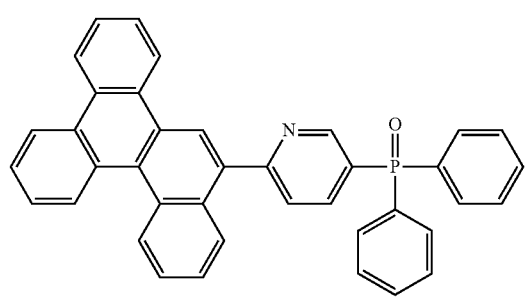

-continued
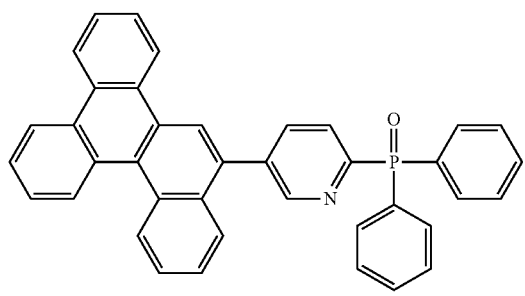
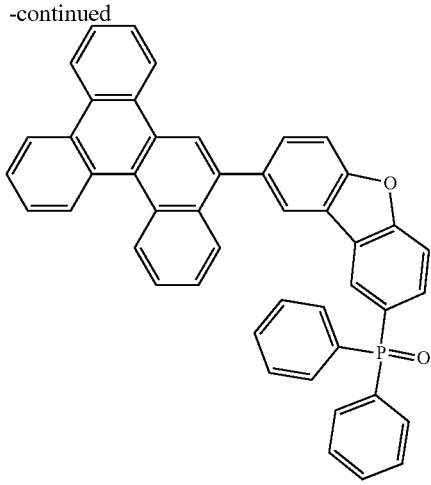
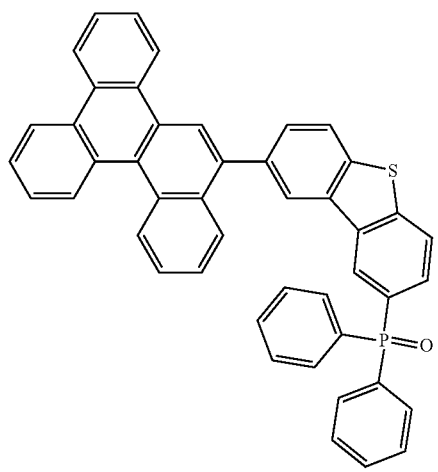
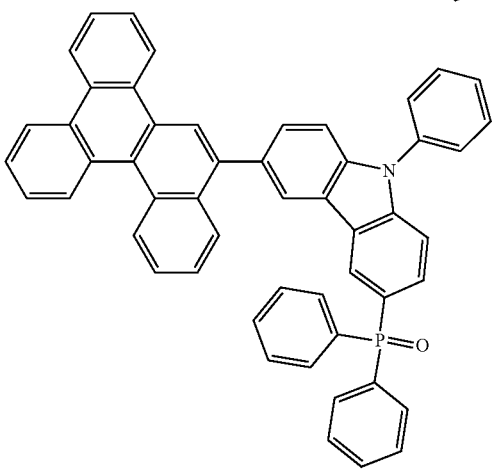
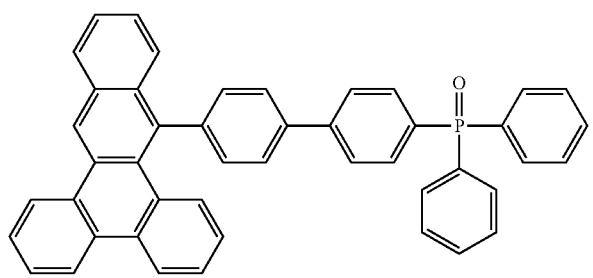
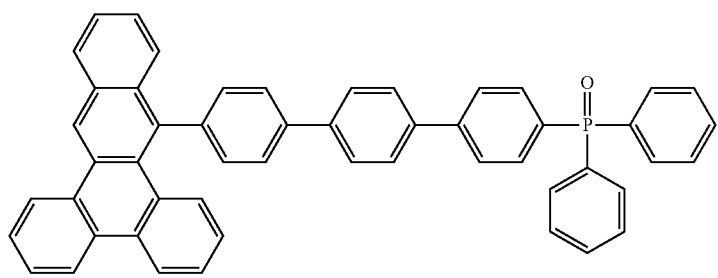

-continued
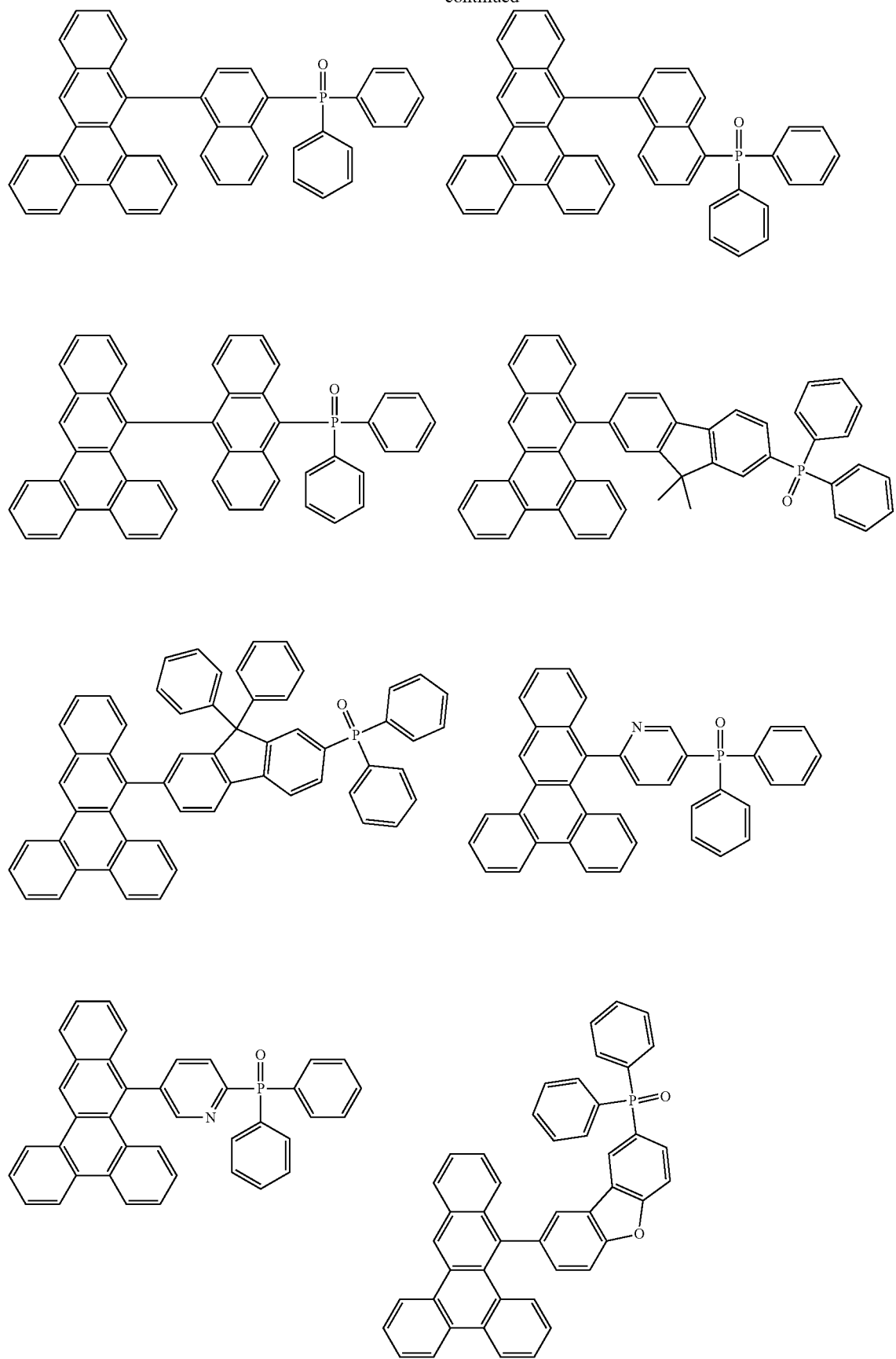

-continued
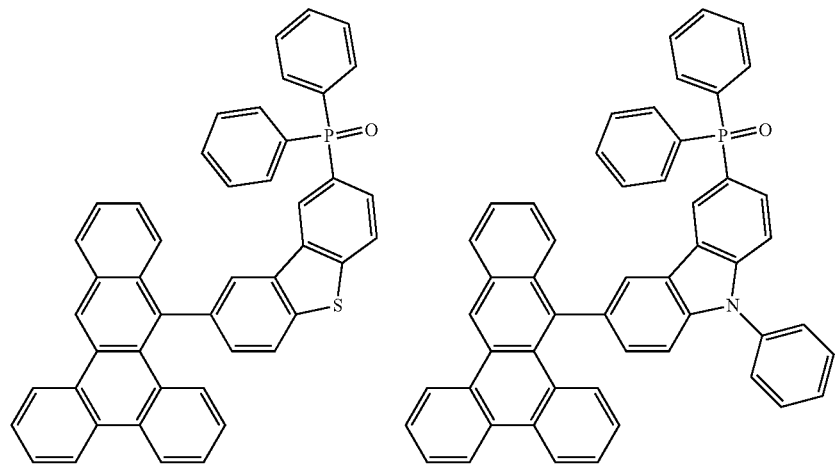
[Chem. 23]
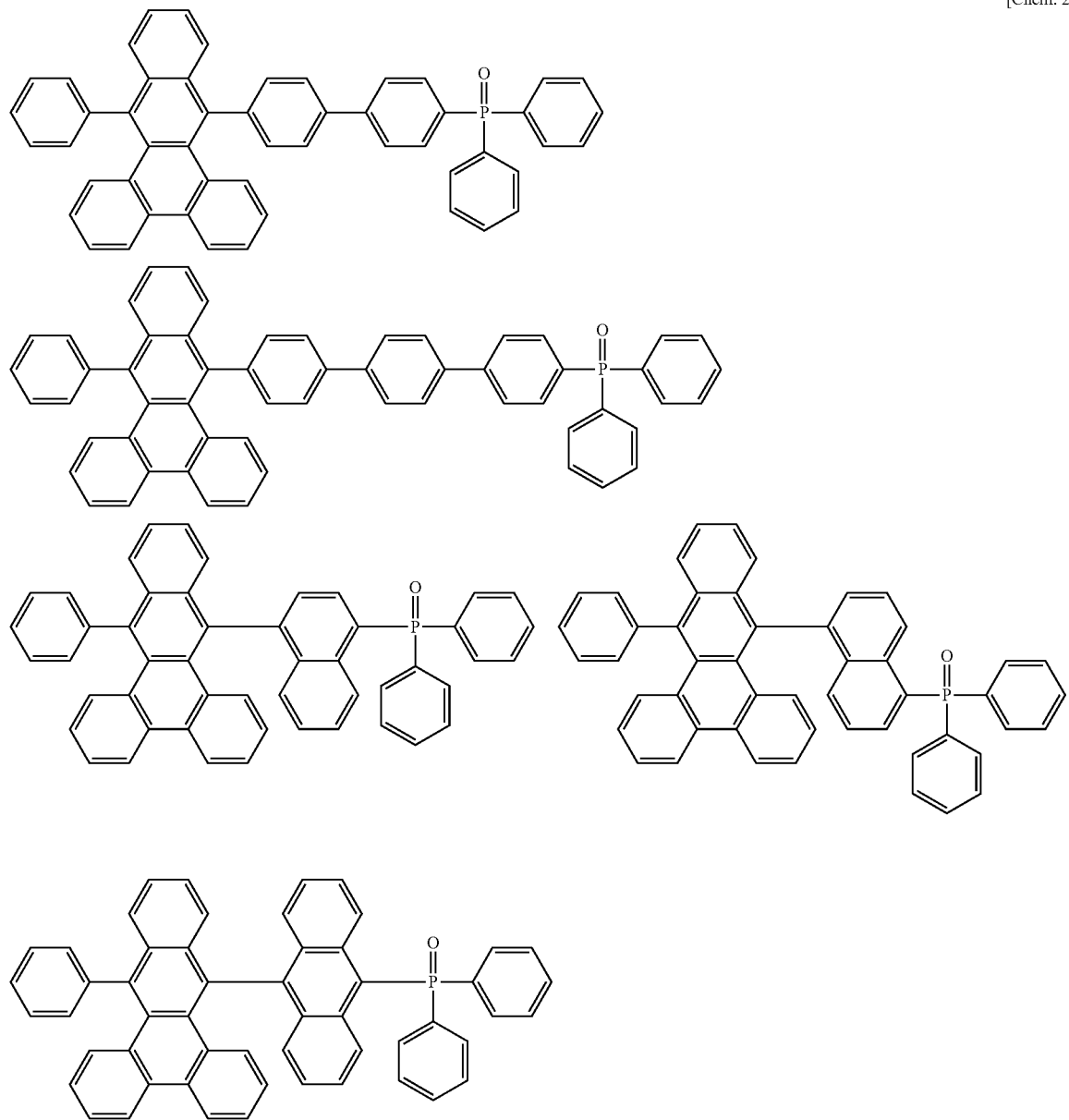

-continued
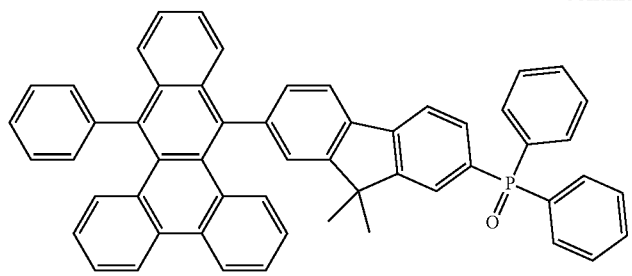
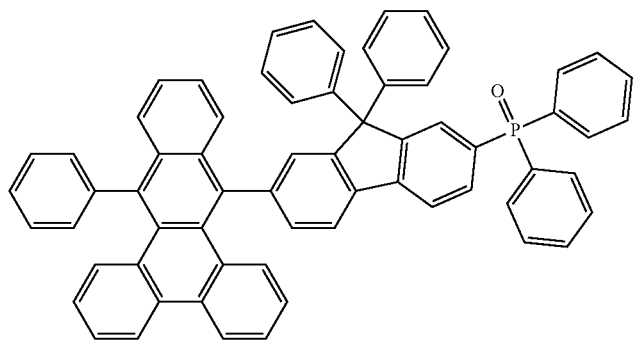
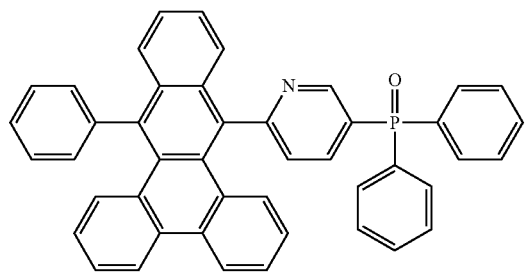
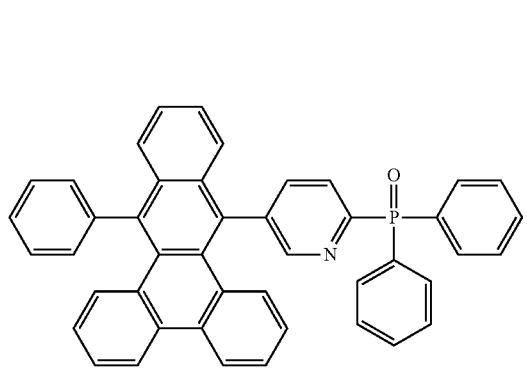
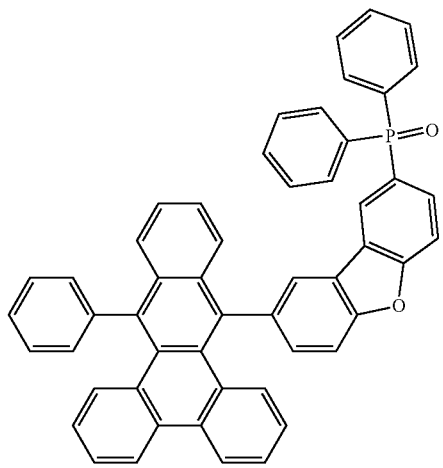
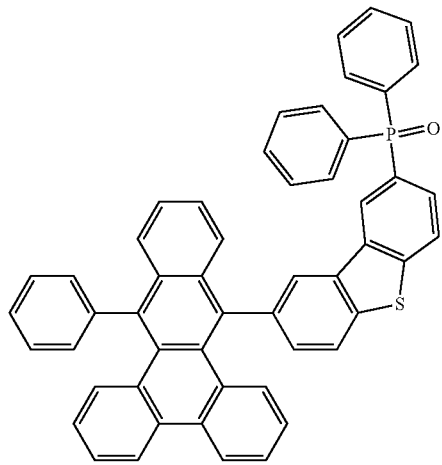
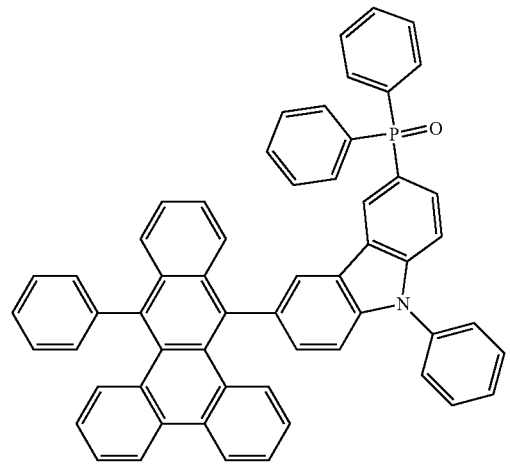

-continued
[Chem. 24]
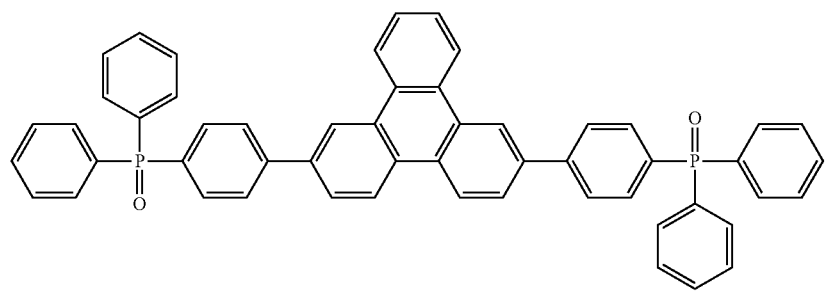
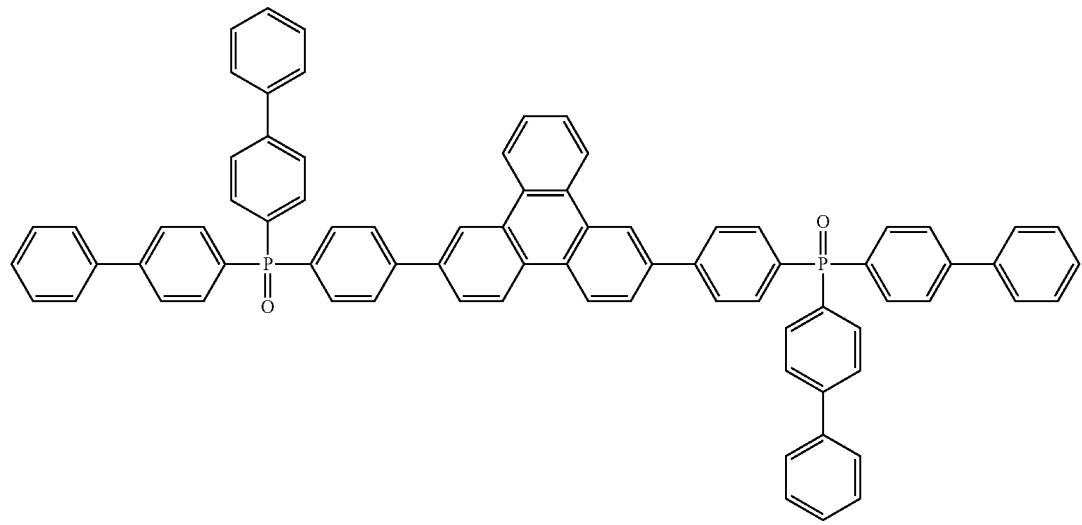
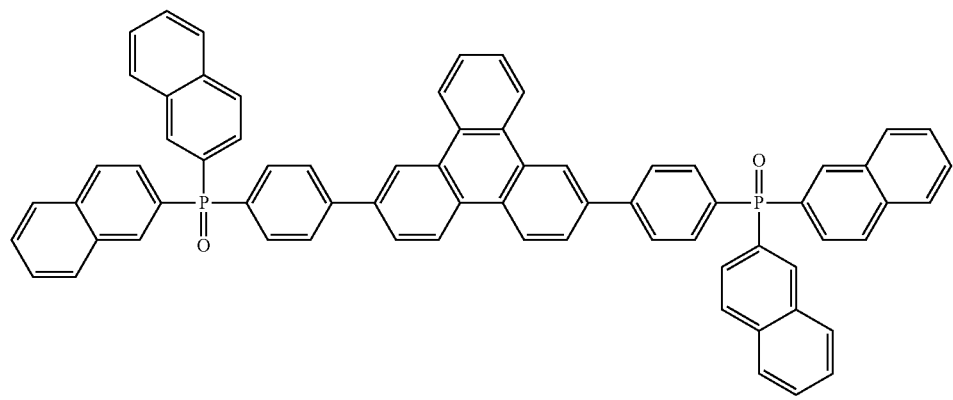
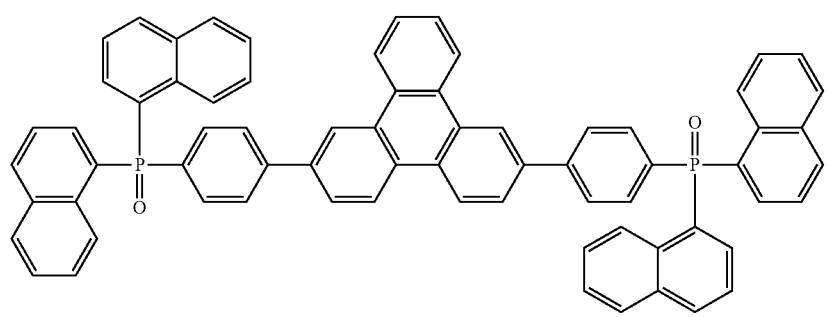

-continued
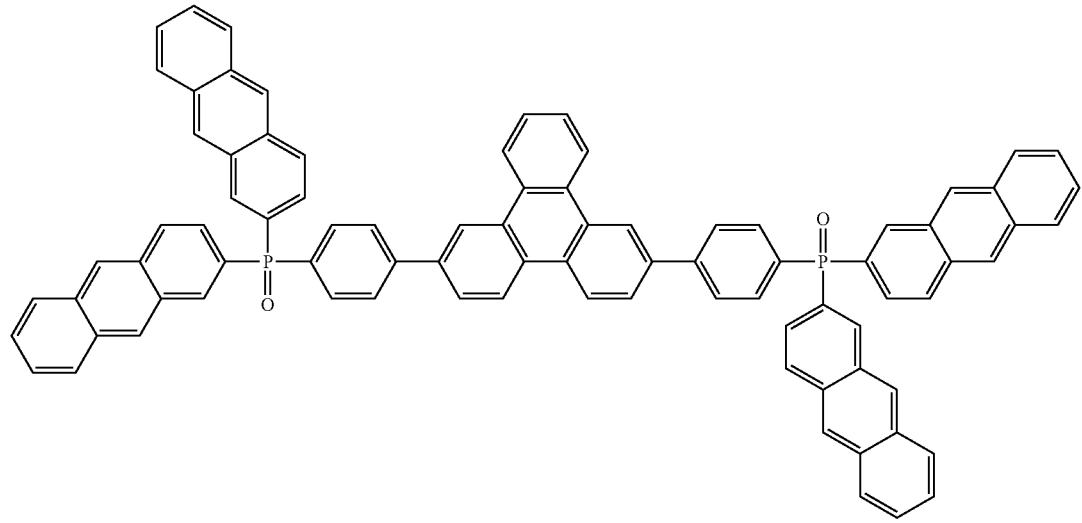
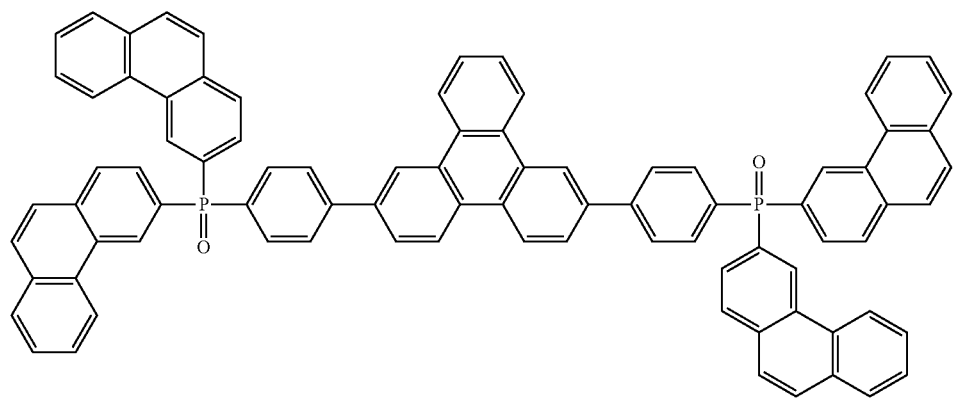
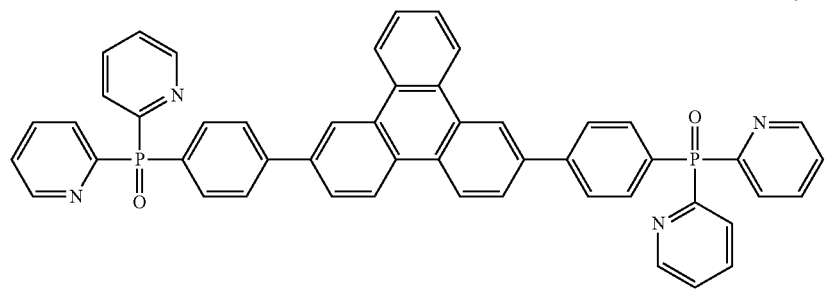
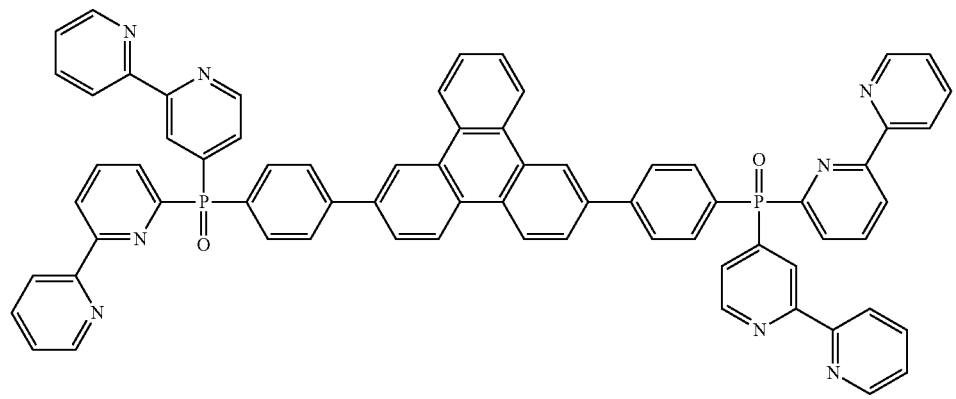

-continued
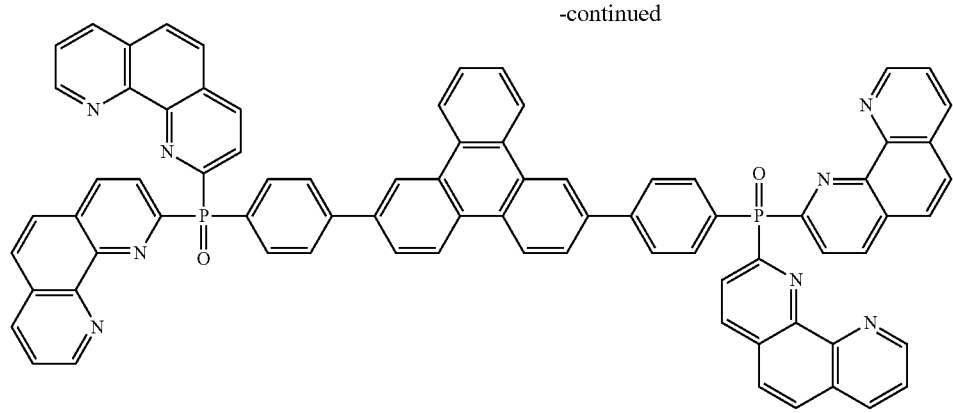
[Chem. 25]
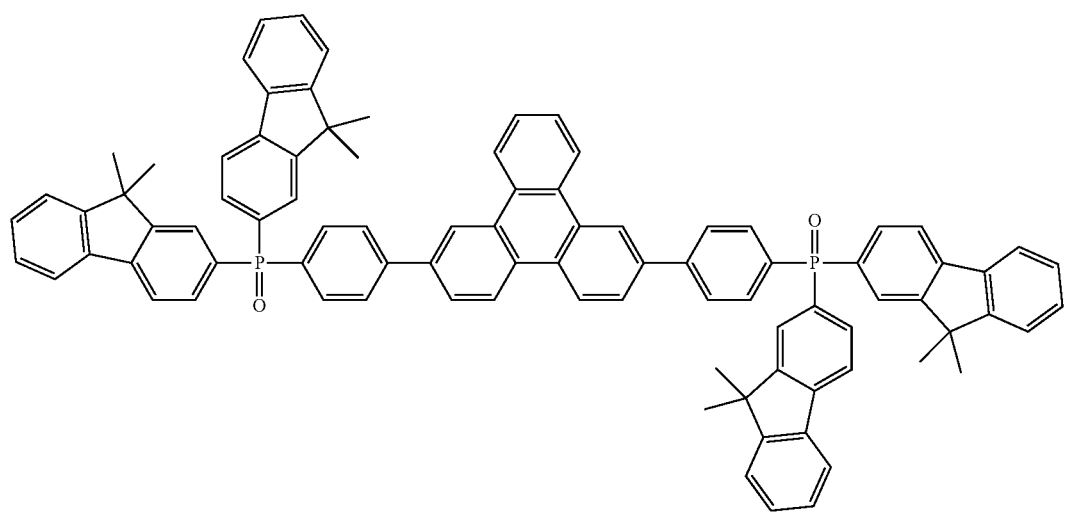
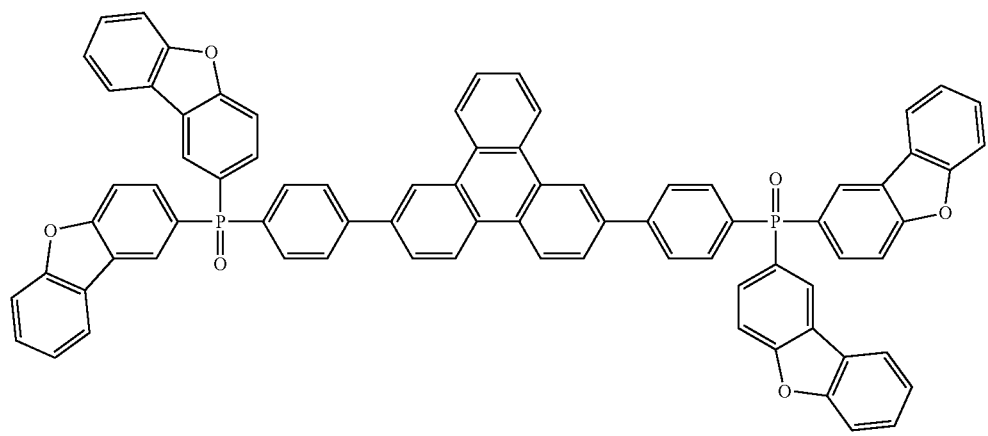

-continued
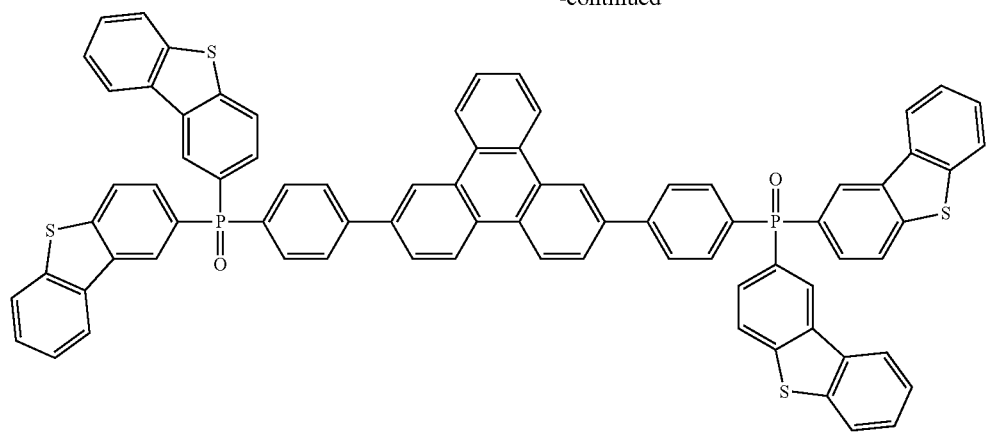
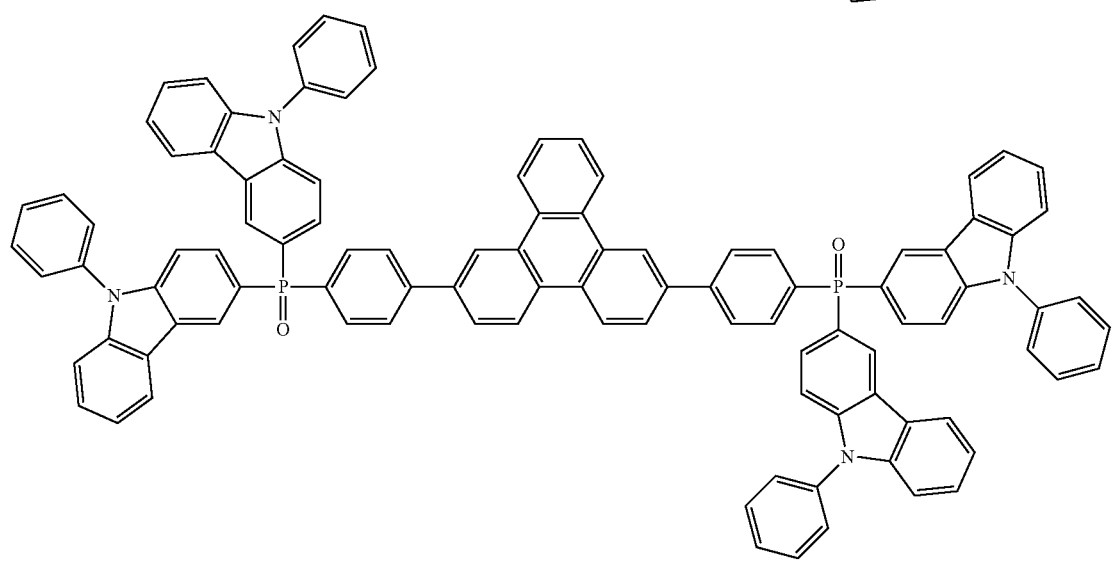
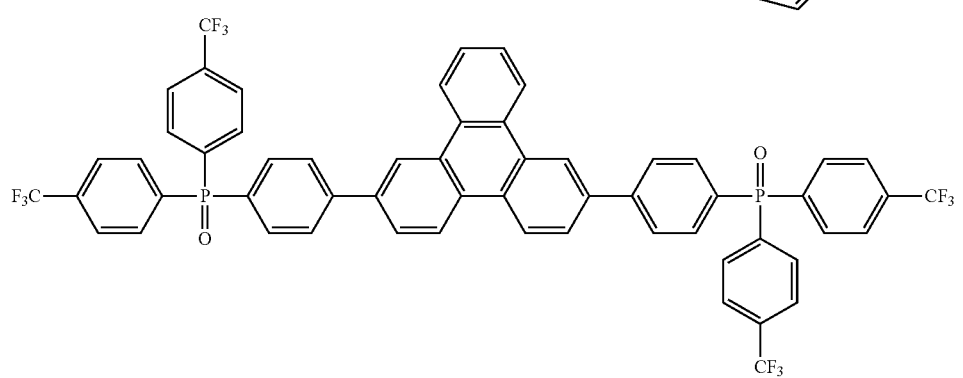
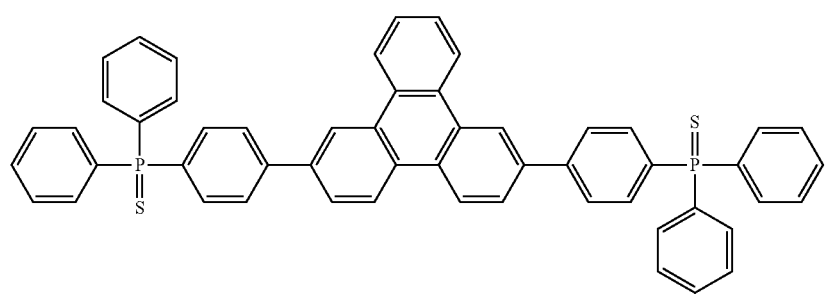

-continued

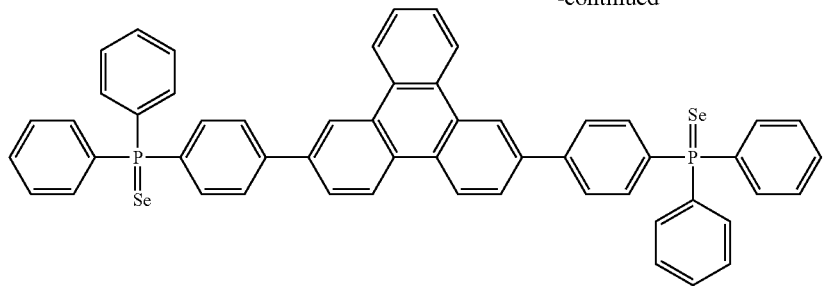

The compound which is an aspect of the present invention is useful as a material for an organic EL device. Also, a kind of the compound which is an aspect of the present invention may be used alone as a material for an organic EL device, and two or more kinds thereof may be combined. Furthermore, the compound which is an aspect of the present invention may be mixed with a known material for an organic EL device and used.

[Organic Electroluminescence Device]

Next, embodiments of the organic EL device which is another aspect of the present invention are explained.

The organic EL device which is an aspect of the present invention has organic thin film layers including a light emitting layer between a cathode and an anode. Because at least one of the organic thin film layers contains the compound which is another aspect of the present invention (sometimes referred to as the material for an organic EL device which is an aspect of the present invention below), driving of the organic EL device at a low voltage is possible, and it is possible to improve the luminous efficacy of the organic EL device and to extend the lifetime.

Examples of the organic thin film layer which contains the material for an organic EL device which is an aspect of the present invention include a hole transporting zone (also referred to as a hole transporting layer but generally referred to as a hole transporting zone so that the case where there is one hole transporting layer and the case where there are two or more hole transporting layers are both included) which is provided between the anode and the light emitting layer of the organic EL device, an electron transporting zone (also referred to as an electron transporting layer but generally referred to as an electron transporting zone so that the case where there is one electron transporting layer and the case where there are two or more electron transporting layers are both included) which is provided between the cathode and the light emitting layer of the organic EL device, a light emitting layer, a spacer layer, a blocking layer and the like.

The material for an organic EL device which is an aspect of the present invention is preferably contained in the electron transporting zone, although it is not particularly limited.

The organic EL device which is an aspect of the present invention may be a monochromatic light emitting device of a fluorescent or phosphorescent type, a white light emitting device of a fluorescent/phosphorescent hybrid type, a simple type having a single light emitting unit or a tandem type having two or more light emitting units. Of these types, a phosphorescent type is preferable. The "light emitting unit" here is the smallest unit which includes one or more organic layers, where one of the layers is a light emitting layer, and which can emit light through the recombination of the injected holes and electrons.

Thus, a representative device structure of the simple-type organic EL device is the following device structure.

(1) Anode/Light Emitting Unit/Cathode

The light emitting unit may be a laminate having phosphorescent light emitting layers and fluorescent light emitting layers, and in this case, the light emitting unit may have spacer layers between the light emitting layers to prevent excitons produced in the phosphorescent light emitting layers from diffusing in the fluorescent light emitting layers. Representative layer structures of the light emitting unit are shown below.

(a) Hole transporting layer/light emitting layer (/electron transporting layer)

(b) Hole transporting layer/first phosphorescent light emitting layer/second phosphorescent light emitting layer (/electron transporting layer)

(c) Hole transporting layer/phosphorescent light emitting layer/spacer layer/fluorescent light emitting layer (/electron transporting layer)

(d) Hole transporting layer/first phosphorescent light emitting layer/second phosphorescent light emitting layer/spacer layer/fluorescent light emitting layer (/electron transporting layer)

(e) Hole transporting layer/first phosphorescent light emitting layer/spacer layer/second phosphorescent light emitting layer/spacer layer/fluorescent light emitting layer (/electron transporting layer)

(f) Hole transporting layer/phosphorescent light emitting layer/spacer layer/first fluorescent light emitting layer/second fluorescent light emitting layer (/electron transporting layer)

(g) Hole transporting layer/electron blocking layer/light emitting layer (/electron transporting layer)

(h) Hole transporting layer/light emitting layer/hole blocking layer (/electron transporting layer)

(i) Hole transporting layer/fluorescent light emitting layer/triplet blocking layer (/electron transporting layer)

In all the layer structures, the acceptor layer described below may be provided between the hole transporting layer and the anode, and preferably, the acceptor layer is provided.

The phosphorescent or fluorescent light emitting layers may emit light of colors which are different from each other. A specific layer structure is, in the laminated light emitting layers (d), hole transporting layer/first phosphorescent light emitting layer (which emits red light)/second phosphorescent light emitting layer (which emits green light)/spacer layer/fluorescent light emitting layer (which emits blue light)/electron transporting layer or the like.

An electron blocking layer may be suitably provided between a light emitting layer and the hole transporting layer or the spacer layer. Also, a hole blocking layer may be suitably provided between a light emitting layer and the electron transporting layer. When an electron blocking layer or a hole blocking layer is provided, it is possible to trap electrons or holes in the light emitting layer, increase the probability of charge recombination in the light emitting layer and extend the lifetime.

A representative device structure of the tandem-type organic EL device is the following device structure.

(2) Anode/First Light Emitting Unit/Intermediate Layer/Second Light Emitting Unit/Cathode As the first light emitting unit and the second light emitting unit, for example, light emitting units which are similar to the light emitting unit described above can be each independently selected.

The intermediate layer is also generally called an intermediate electrode, an intermediate conductive layer, a charge generating layer, an electron withdrawing layer, a connection layer or an intermediate insulating layer, and a known material composition which supplies electrons to the first light emitting unit and holes to the second light emitting unit can be used.

The rough structure of an example of the organic EL device which is an aspect of the present invention is shown in FIG. 1. The organic EL device 1 has a substrate 2, an anode 3, a cathode 4 and organic thin film layers 10 provided between the anode 3 and the cathode 4. The organic thin film layers 10 include a light emitting layer 5 including at least one phosphorescent light emitting layer containing a phosphorescent host material and a phosphorescent dopant (phosphorescent materials). A hole transporting zone (hole transporting layer) 6 or the like may be formed between the light emitting layer 5 and the anode 3, and an electron transporting zone (electron transporting layer) 7 or the like may be formed between the light emitting layer 5 and the cathode 4. Also, an electron blocking layer may be provided on the anode 3 side of the light emitting layer 5, and a hole blocking layer may be provided on the cathode 4 side of the light emitting layer 5. The electron blocking layer and the hole blocking layer can trap electrons and holes in the light emitting layer 5 and increase the probability of the exciton generation in the light emitting layer 5.

In the present specification, a host combined with a fluorescent dopant is called a fluorescent host, and a host combined with a phosphorescent dopant is called a phosphorescent host. The fluorescent host and the phosphorescent host are not distinguished from each other only by the molecular structures. That is, the phosphorescent host means a material constituting a phosphorescent light emitting layer containing a phosphorescent dopant, but it is not meant that the phosphorescent host cannot be used as a material constituting a fluorescent light emitting layer. The same applies to the fluorescent host.

(Substrate)

The substrate is used as a support of the light emitting device. As the substrate, for example, glass, quartz, a plastic and the like can be used. Also, a flexible substrate may be used. A flexible substrate is a substrate which can be folded (flexible) and is for example a plastic substrate of polycarbonate, polyarylate, polyethersulfone, polypropylene, polyester, polyvinyl fluoride or polyvinyl chloride or the like. Moreover, an inorganic deposited film can also be used.

(Anode)

For the anode formed on the substrate, a metal, an alloy and an electroconductive compound which have high work functions (specifically, 4.0 eV or more) as well as a mixture thereof and the like are preferably used. Specific examples include indium tin oxide (ITO), indium tin oxide containing silicon or silicon oxide, indium zinc oxide, tungsten oxide, indium oxide containing zinc oxide, graphene and the like. Moreover, gold (Au), platinum (Pt), a nitride of a metal material (for example, titanium nitride) and the like are also included.

(Hole Transporting Zone)

The organic EL device of the present invention preferably has a hole transporting zone between the light emitting layer and the anode.

The hole transporting zone contains a substance having high hole injecting capability and/or high hole transporting capability.

As substances having high hole injecting capability, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide and the like can be used.

Aromatic amine compounds such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino) biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2) and 3-[N-(1-naphthyl)-N-(9-phenylcarbazol-3-yl)amino]-9-phenylcarbazole (abbreviation: PCzPCN1), which are low molecular organic compounds, and the like can also be used.

High molecular compounds (oligomers, dendrimers, polymers and the like) can also be used. Examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA) and poly[N,N'-bis(4-butylphenyl)-N,N'-bis(phenyl)benzidine] (abbreviation: Poly-TPD). Also, high molecular compounds to which an acid has been added such as poly(3,4-ethylenedioxythiophene)/poly(styrene sulfonic acid) (PEDOT/PSS) and polyaniline/poly(styrene sulfonic acid) (PAni/PSS) can also be used.

In addition, for the hole transporting zone, aromatic amine compounds, carbazole derivatives and anthracene derivatives which are substances having high hole transporting capability and the like can be used. Specifically, aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA) and 4,4'-bis[N-(spiro-9,9'-bifluoren-2-yl)-N-phenylamino]biphenyl (abbreviation: BSPB) and the like can be used. The substances mentioned here are substances mainly having hole mobility of 106 $cm^2$/Vs or more.

For the hole transporting layer, carbazole derivatives such as CBP, CzPA and PCzPA and anthracene derivatives such as t-BuDNA, DNA and DPAnth may also be used. High molecular compounds such as poly(N-vinylcarbazole) (abbreviation: PVK) and poly(4-vinyltriphenylamine) (abbreviation: PVTPA) can also be used.

However, substances other than these substances may also be used as long as the hole transporting capability is higher than the electron transporting capability.

The hole transporting layer of the organic EL device of an embodiment of the present invention may have a two-layer structure including a first hole transporting layer (anode side) and a second hole transporting layer (cathode side).

The thickness of the hole transporting layer is not particularly limited but is preferably 10 nm to 300 nm. When the hole transporting layer has the two-layer structure, the thickness of the first hole transporting layer is preferably 50 to 300 nm, more preferably 50 to 250 nm, still more preferably 50 to 150 nm, and particularly preferably 50 to 100 nm, and the thickness of the second hole transporting layer is preferably 5 to 100 nm, more preferably 5 to 50 nm, still more preferably 5 to 30 nm, and particularly preferably 5 to 20 nm, although the thicknesses are not particularly limited.

(Guest Material of Light Emitting Layer)

The light emitting layer is a layer containing a highly luminescent substance, and various materials can be used. For example, as highly luminescent substances, fluorescent compounds which emit fluorescent light and phosphorescent compounds which emit phosphorescent light can be used. A fluorescent compound is a compound which can emit light from the singlet excitation state, and a phosphorescent compound is a compound which can emit light from the triplet excitation state.

As blue fluorescent light emitting materials which can be used for the light emitting layer, pyrene derivatives, styrylamine derivatives, chrysene derivatives, fluoranthene derivatives, fluorene derivatives, diamine derivatives, triarylamine derivatives and the like can be used. Specifically, N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA) and the like are used.

As green fluorescent light emitting materials which can be used for the light emitting layer, aromatic amine derivatives and the like can be used. Specifically N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA) and the like are used.

As red fluorescent light emitting materials which can be used for the light emitting layer, tetracene derivatives, diamine derivatives and the like can be used. Specifically N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD) and the like are used.

As blue phosphorescent light emitting materials which can be used for the light emitting layer, metal complexes such as iridium complexes, osmium complexes and platinum complexes, preferably, ortho-metalated complexes of iridium, osmium or platinum metal are used. Specifically, bis[2-(4',6'-difluorophenyl)pyridinato-N,C2'] iridium(III) tetrakis(1-pyrazolyl)borate (abbreviation: FIr6), bis[2-(4',6'-difluorophenyl)pyridinato-N,C2'] iridium(III) picolinate (abbreviation: FIrpic), bis[2-(3',5'bistrifluoromethylphenyl) pyridinato-N,C2'] iridium(III) picolinate (abbreviation: Ir(CF3ppy)2(pic)), bis[2-(4',6'-difluorophenyl)pyridinato-N,C2'] iridium(III) acetylacetonate (abbreviation: FIracac) and the like are used.

As green phosphorescent light emitting materials which can be used for the light emitting layer, iridium complexes and the like are used. Tris(2-phenylpyridinato-N,C2') iridium(III) (abbreviation: Ir(ppy)3), bis(2-phenylpyridinato-N,2') iridium(III) acetylacetonate (abbreviation: Ir(ppy)2(acac)), bis(1,2-diphenyl-1H-benzimidazolato) iridium(III) acetylacetonate (abbreviation: Ir(pbi)2(acac)), bis(benzo[h]quinolinato) iridium(III) acetylacetonate (abbreviation: Ir(bzq)2(acac)) and the like are used.

As red phosphorescent light emitting materials which can be used for the light emitting layer, metal complexes such as iridium complexes, platinum complexes, terbium complexes and europium complexes are used. Specifically, organometallic complexes such as bis[2-(2'-benzo[4,5-a]thienyl)pyridinato-N,C3']iridium(III) acetylacetonate (abbreviation: Ir(btp)2(acac)), bis(1-phenylisoquinolinato-N,C2') iridium (III) acetylacetonate (abbreviation: Ir(piq)2(acac)), (acetylacetonato)bis[2,3-bis(4-fluorophenyl)quinoxalinato] iridium(III) (abbreviation: Ir(Fdpq)2(acac)) and 2,3,7,8,12, 13,17,18-octaethyl-21H,23H-porphyrin platinum(II) (abbreviation: PtOEP) are used.

Also, rare-earth metal complexes such as tris(acetylacetonato)(monophenanthroline) terbium(III) (abbreviation: Tb(acac)3(Phen)), tris(1,3-diphenyl-1,3-propanedionato) (monophenanthroline) europium(III) (abbreviation: Eu(DBM)3(Phen)) and tris[1-(2-thenoyl)-3,3,3-trifluoroacetonato](monophenanthroline) europium(III) (abbreviation: Eu(TTA)3(Phen)) can be used as phosphorescent compounds because light is emitted from rare-earth metal ions (electron transition between different multiplicities).

(Host Material of Light Emitting Layer)

The light emitting layer may have a composition in which any of the highly luminescent substances (guest materials) described above is dispersed in another substance (host material). Various substances can be used as the substance for dispersing a highly luminescent substance, and a substance which has a higher lowest unoccupied molecular orbital level (LUMO level) and a lower highest occupied molecular orbital level (HOMO level) than the highly luminescent substance is preferably used.

The substance for dispersing the highly luminescent substance (host material) is preferably the compound which is an aspect of the present invention. In addition to the compound which is an aspect of the present invention, for example, 1) metal complexes such as aluminum complexes, beryllium complexes or zinc complexes, 2) heterocyclic compounds such as oxadiazole derivatives, benzimidazole derivatives or phenanthroline derivatives, 3) condensed aromatic compounds such as carbazole derivatives, anthracene derivatives, phenanthrene derivatives, pyrene derivatives or chrysene derivatives and 3) aromatic amine compounds such as triarylamine derivatives or condensed polycyclic aromatic amine derivatives can be used. More specifically, metal complexes such as tris(8-quinolinolato) aluminum(III) (abbreviation: Alq), tris(4-methyl-8-quinolinolato) aluminum(III) (abbreviation: Almq3), bis(10-hydroxybenzo[h]quinolinato) beryllium(II) (abbreviation: BeBq2), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato] zinc(II) (abbreviation: ZnPBO) and bis[2-(2-benzothiazolyl)phenolato] zinc(II) (abbreviation: ZnBTZ), heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen) and bathocuproine (abbreviation: BCP), condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-nap hthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth) and 6,12-dimethoxy-5,11-diphenylchrysene, aromatic amine compounds such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA). NPB (or α-NPD), TPD, DFLDPBi and BSPB and the like can be used. Two or more kinds of the substance for dispersing the highly luminescent substance (guest material) (host material) can be used.

(Electron Transporting Zone)

The electron transporting zone contains a substance having high electron injecting capability and/or high electron transporting capability. As described above, the electron transporting zone preferably contains the compound which is an aspect of the present invention.

For the electron transporting zone, alkali metals, alkaline earth metals or compounds thereof such as lithium (Li), cesium (Cs), calcium (Ca), lithium fluoride (LiF), cesium fluoride (CsF), calcium fluoride (CaF$_2$) and lithium oxide (LiOx), which are substances having high electron injecting capability, can be used. In addition, a material obtained by adding an alkali metal, an alkaline earth metal or a compound thereof to a substance having electron transporting capability, specifically Alq containing magnesium (Mg), or the like may also be used. In this case, electrons can be injected more efficiently from the cathode.

Alternatively, a composite material obtained by mixing an organic compound and an electron-donating dopant may also be used for the electron transporting zone. Such a composite material has excellent electron injecting capability and excellent electron transporting capability, because electrons are generated in the organic compound due to the electron-donating dopant. In this case, the organic compound is preferably a material which is excellent in transporting the generated electrons, and specifically, the compound which is an aspect of the present invention and the substances constituting the electron transporting layer described above (the metal complexes, the heteroaromatic compounds and the like) can be used. The electron-donating dopant may be a substance which donates electrons to the organic compound. Specifically, alkali metals, alkali metal compounds, alkaline earth metals, alkaline earth metal compounds, rare-earth metals and rare-earth metal compounds are used, and at least one selected from these substances is preferable. The alkali metals, the alkaline earth metals and the rare-earth metals include lithium, cesium, magnesium, calcium, erbium, ytterbium and the like. Alkali metal oxides and alkaline earth metal oxides are also preferable, and for example, lithium oxide, calcium oxide, barium oxide and the like can be used. Also, Lewis bases such as magnesium oxide can be used. Moreover, organic compounds such as tetrathiafulvalene (abbreviation: TTF) can also be used.

In addition, for the electron transporting zone, 1) organometallic complexes such as aluminum complexes, beryllium complexes and zinc complexes, 2) heteroaromatic compounds such as imidazole derivatives, benzimidazole derivatives, azine derivatives, carbazole derivatives and phenanthroline derivatives and 3) high molecular compounds, which are substances having high electron transporting capability, can be used.

As the organometallic complexes, at least one selected from an organometallic complex containing an alkali metal, an organometallic complex containing an alkaline earth metal and an organometallic complex containing a rare-earth metal is preferably used.

With respect to specific examples of the organometallic complexes, 8-quinolinolatolithium (abbreviation: Liq), Alq, tris(4-methyl-8-quinolinolato) aluminum (abbreviation: Almq3), bis(10-hydroxybenzo[h]quinolinato) beryllium (abbreviation: BeBq2), BAlq, Znq, ZnPBO, ZnBTZ and the like can be used.

Specific examples of the heteroaromatic compounds include 2-(4-biphenylyl)-5-(4-tert-butylphenyl)-1,3,4-oxadiazole (abbreviation: PBD), 1,3-bis[5-(ptert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), 4,4'-bis(5-methylbenzoxazol-2-yl)stilbene (abbreviation: BzOs) and the like.

Specific examples of the high molecular compounds include poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like.

The substances mentioned here are substances mainly having electron mobility of 10-6 cm$^2$/Vs or more. Substances other than the above substances may also be used for the electron transporting layer as long as the electron transporting capability is higher than the hole transporting capability. Also, the electron transporting zone may be not only a single layer but also a laminate of two or more layers of the substances above.

In an aspect of the present invention, the electron transporting zone preferably contains at least one selected from the electron-donating dopants and the organometallic complexes in addition to the compound which is an aspect of the present invention.

(Cathode)

For the cathode, a metal, an alloy and an electroconductive compound which have low work functions (specifically, 3.8 eV or less) as well as a mixture thereof and the like are preferably used. Specific examples of such a cathode material include group 1 or group 2 elements of the periodic table of the elements, namely alkali metals such as lithium (Li) and cesium (Cs), alkaline earth metals such as magnesium (Mg), rare-earth metals such as alloys containing the metals (for example, MgAg and AlLi), alloys containing the metals and the like.

(Acceptor Layer)

The organic EL device which is an aspect of the present invention may have a layer containing an acceptor material, namely an acceptor layer, between the anode and the hole transporting zone, and the organic EL device preferably has an acceptor layer. It is expected that this decreases the driving voltage and decreases the production costs.

The acceptor material is preferably a compound represented by the following formula (K).

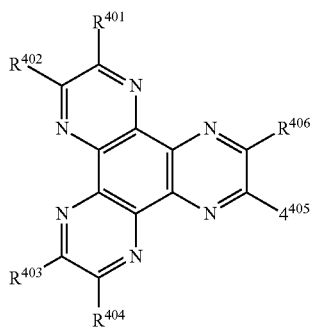

(K)

In the formula (K), $R^{401}$ to $R^{406}$ each independently represent a cyano group, —$CONH_2$, a carboxyl group or —$COOR^{407}$ ($R^{407}$ is an alkyl group having 1 to 20 carbon atoms), or $R^{401}$ and $R^{402}$, $R^{403}$ and $R^{404}$ or $R^{405}$ and $R^{406}$ combine and represent a group represented by —CO—O—CO—.

The alkyl group represented by $R^{407}$ is a methyl group, an ethyl group, an n-propyl group, an isopropyl group, an n-butyl group, an isobutyl group, a tert-butyl group, a cyclopentyl group, a cyclohexyl group or the like.

The thickness of the layer containing the acceptor material is not particularly limited but is preferably 5 to 20 nm.

(n/p Doping)

The carrier injecting capability of the hole transporting layer and the electron transporting layer can be adjusted by doping with a donor material (n) or doping with an acceptor material (p) as described in the specification of U.S. Pat. No. 3,695,714.

A representative example of n-doping is a method in which an electron transporting material is doped with a metal such as Li or Cs, and a representative example of p-doping is a method in which a hole transporting material is doped with an acceptor material such as 2,3,5,6-tetrafluoro-7,7,8,8-tetracyanoquinodimethane ($F_4TCNQ$).

(Spacer Layer)

The spacer layer is, for example when a fluorescent light emitting layer and a phosphorescent light emitting layer are laminated, a layer which is provided between the fluorescent light emitting layer and the phosphorescent light emitting layer for the purposes of preventing the excitons produced in the phosphorescent light emitting layer from diffusing in the fluorescent light emitting layer or of adjusting the carrier balance. Also, the spacer layer can be provided between phosphorescent light emitting layers.

Because the spacer layer is provided between light emitting layers, a material having both electron transporting capability and hole transporting capability is preferable. Also, to prevent the diffusion of the triplet energy in a neighboring phosphorescent light emitting layer, the triplet energy is preferably 2.6 eV or more. The materials used for the spacer layer are materials similar to those used for the hole transporting layer.

(Blocking Layer)

The organic EL device which is an aspect of the present invention can also have a blocking layer such as an electron blocking layer, a hole blocking layer or a triplet blocking layer, at a part neighboring a light emitting layer. Here, the electron blocking layer is a layer which prevents the leakage of electrons from the light emitting layer to the hole transporting layer, and the hole blocking layer is a layer which prevents the leakage of holes from the light emitting layer to the electron transporting layer.

The triplet blocking layer has a function of inhibiting the energy deactivation of a triplet exciton on a molecule of the electron transporting layer other than the light emitting dopant by preventing the triplet exciton produced in the light emitting layer from diffusing in the surrounding layers and by trapping the triplet exciton in the light emitting layer.

In a case of providing the triplet blocking layer in a phosphorescent device, it is speculated that the triplet excitons of the phosphorescent light emitting dopant can be trapped (cannot move to another molecule) due to the energy relation, that the energy deactivation pathways other than the emission of light on the dopant are blocked and that the light can be emitted highly efficiently, when the energy relation $E^T_d < E^T_{TB}$ is satisfied, where $E^T_d$ is the triplet energy of the phosphorescent light emitting dopant in the light emitting layer, and $E^T_{TB}$ is the triplet energy of the compound used for the triplet blocking layer. However, it is thought that even when the relation $E^T_d < E^T_{TB}$ is satisfied, when the energy difference $\Delta E^T = E^T_{TB} - E^T_d$ is small, the triplet excitons can get over the energy difference $\Delta E^T$ endothermically due to the thermal energy of the surroundings and move to another molecule, in an environment at around room temperature, which is an actual environment where the device is driven. In particular, because the exciton lifetime is longer in phosphorescence than in fluorescence, the influence of the endothermic exciton transfer process is exerted relatively easily. The energy difference $\Delta E^T$ is preferably as large as possible relative to the thermal energy of room temperature and is still more preferably 0.1 eV or more, and particularly preferably 0.2 eV or more.

Also, the electron mobility of the material constituting the triplet blocking layer is desirably 10-6 $cm^2/Vs$ or more in the electric field intensity range of 0.04 to 0.5 MV/cm. Some methods such as the Time of Flight method are known as the methods for measuring the electron mobility of an organic material, but the electron mobility here is the value determined by impedance spectrometry.

The electron mobility of the material constituting the electron injecting layer is desirably 10-6 $cm^2/Vs$ or more in the electric field intensity range of 0.04 to 0.5 MV/cm. This is to promote the electron injection from the cathode to the electron transporting layer, promote the electron injection also to the neighboring blocking layer and light emitting layer and enable driving at a lower voltage.

The organic EL device obtained using the compound which is an aspect of the present invention can be driven at a low voltage and has high luminous efficacy and a long lifetime. Thus, the organic EL device can be used for electronic equipments such as display parts including an organic EL panel module and the like; display devices of a television, a mobile phone, a personal computer and the like; and light emitting devices including a light, a vehicle light and the like.

EXAMPLES

Next, the present invention is explained in further detail by Examples and Comparative Examples, but the present invention is not limited at all by the contents described in the Examples.

Example 1

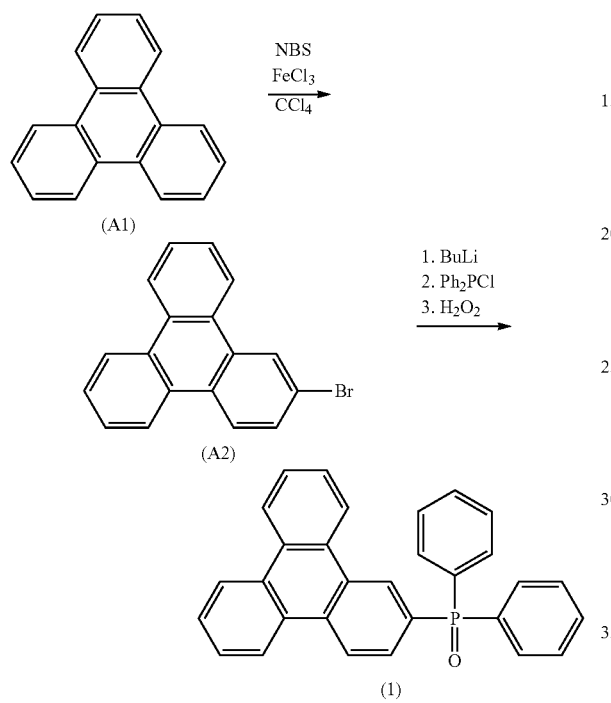

(1-1) Synthesis of Intermediate (A2)

Carbon tetrachloride (1,500 mL) was added to the intermediate (A1) (5.14 g, 22.5 mmol), N-bromosuccinimide (4.00 g, 22.5 mmol) and iron(III) chloride hexahydrate (182 mg, 0.675 mmol), and the mixture was stirred while heating under reflux for seven hours.

After the completion of the reaction, the solvent was distilled off at reduced pressure. The mixture was purified by silica gel column chromatography, and the intermediate (A2) (3.75 g, 12.2 mmol, yield 54%) was thus obtained.

(1-2) Synthesis of Compound (1)

In an argon atmosphere, the intermediate (A2) (3.10 g, 10.1 mmol) was dissolved in tetrahydrofuran (50 mL), and after cooling the solution to −78° C., n-butyllithium (2.50M hexane solution, 6.87 mL, 17.2 mmol) was dropped over 30 minutes. After stirring at −78° C. for an hour, the temperature was raised to −50° C., and diphenylphosphine chloride (2.23 g, 10.1 mmol) was added. The temperature was raised to room temperature, and the mixture was stirred for seven hours. Then, the reaction was stopped by adding methanol (50 mL) to the mixture, and then the solvent was distilled off at reduced pressure.

The residue was dissolved in dichloromethane (100 mL), and hydrogen peroxide solution (15 mL) was added. The mixture was stirred again for seven hours. Subsequently, the mixture was washed with a salt solution, dried over magnesium sulfate and then concentrated. Then, the mixture was purified by silica gel column chromatography, and a compound (1.47 g, 3.43 mmol, yield 34%) was thus obtained. As a result of mass spectrometry, the m/e value of the compound was 428, and the compound was identified as the compound (1) (Exact mass: 428.13).

Example 2

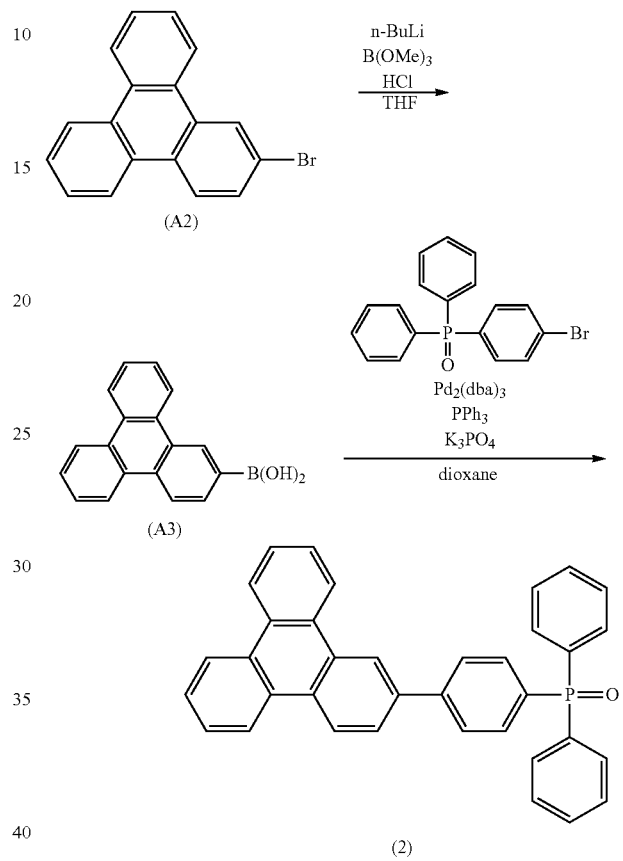

(2-1) Synthesis of Intermediate (A3)

In an argon atmosphere, the intermediate (A2) (2.90 g, 9.44 mmol) and tetrahydrofuran (80 mL) were mixed and cooled to −78° C. Then, n-butyllithium (1.60M hexane solution, 6.20 mL, 9.91 mmol) was added, and the temperature was raised to 0° C. over two hours. Next, the mixture was cooled to −78° C. again, and after adding trimethoxyborane (2.58 g, 24.8 mmol) and stirring at −78° C. for 20 minutes, the temperature was raised to room temperature over eight hours.

After the completion of the reaction, an aqueous hydrochloric acid solution (1M, 20 mL) was added, and the mixture was stirred at room temperature for an hour, followed by extraction using ethyl acetate. The solution was dried over magnesium sulfate, then concentrated and suspended in and washed with hexane, and the intermediate (A3) (1.46 g, 5.38 mmol, yield 57%) was obtained by recovery through filtration.

(2-2) Synthesis of Compound (2)

In an argon atmosphere, 1,4-dioxane (50 mL) was added to the intermediate (A3) (1.40 g, 5.14 mmol), (4-bromophenyl)phosphine oxide (1.84 g, 5.14 mmol), tris(dibenzylideneacetone)dipalladium(0) (71 mg, 0.0771 mmol), triphenylphosphine (147 mg, 0.561 mmol) and tripotassium phosphate (6.53 g, 30.8 mmol), and the mixture was stirred at 100° C. for seven hours.

After the completion of the reaction, the mixture was diluted with water, followed by extraction using chloroform. Subsequently, the mixture was washed with a saturated salt solution, dried over magnesium sulfate and then concentrated. Then, the mixture was purified by silica gel column chromatography, and then a compound (1.24 g, 2.47 mmol, yield 48%) was obtained by recrystallization from ethyl acetate. As a result of mass spectrometry, the m/e value of the compound was 504, and the compound was identified as the compound (2) (Exact mass: 504.16).

Example 3

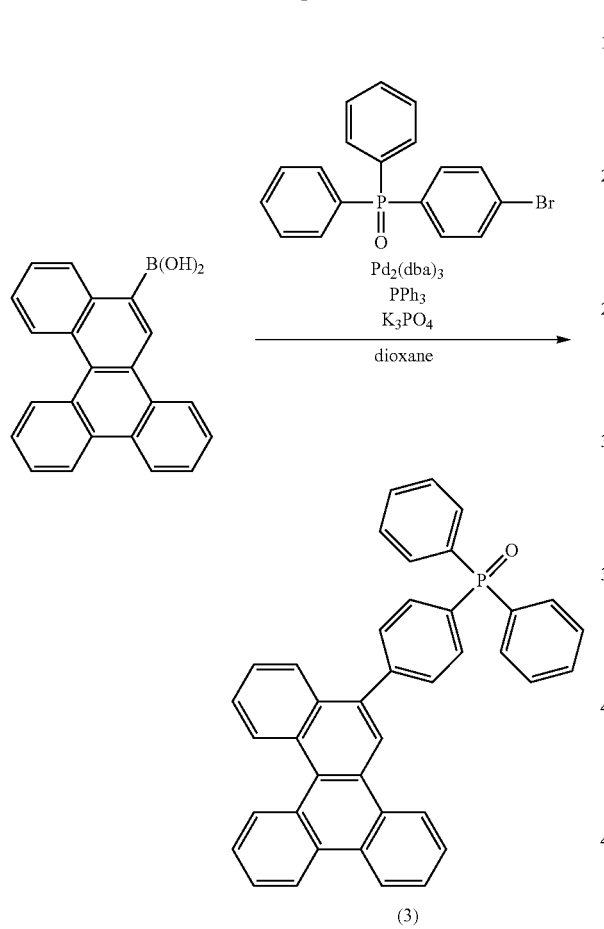

(3)

In an argon atmosphere, 1,4-dioxane (100 mL) was added to benzo[g]chrysene-10-boronic acid (2.90 g, 9.00 mmol), (4-bromophenyl)phosphine oxide (3.21 g, 9.00 mmol), tris(dibenzylideneacetone)dipalladium(0) (124 mg, 0.135 mmol), triphenylphosphine (283 mg, 1.08 mmol) and tripotassium phosphate (11.5 g, 54.0 mmol), and the mixture was stirred at 100° C. for eight hours.

After the completion of the reaction, the mixture was diluted with water, followed by extraction using chloroform. Subsequently, the mixture was washed with a saturated salt solution, dried over magnesium sulfate and then concentrated. Then, the mixture was purified by silica gel column chromatography, and then a compound (3.24 g, 6.85 mmol, yield 65%) was obtained by recrystallization from ethyl acetate. As a result of mass spectrometry, the m/e value of the compound was 554, and the compound was identified as the compound (3) (Exact mass: 554.63).

Example 4

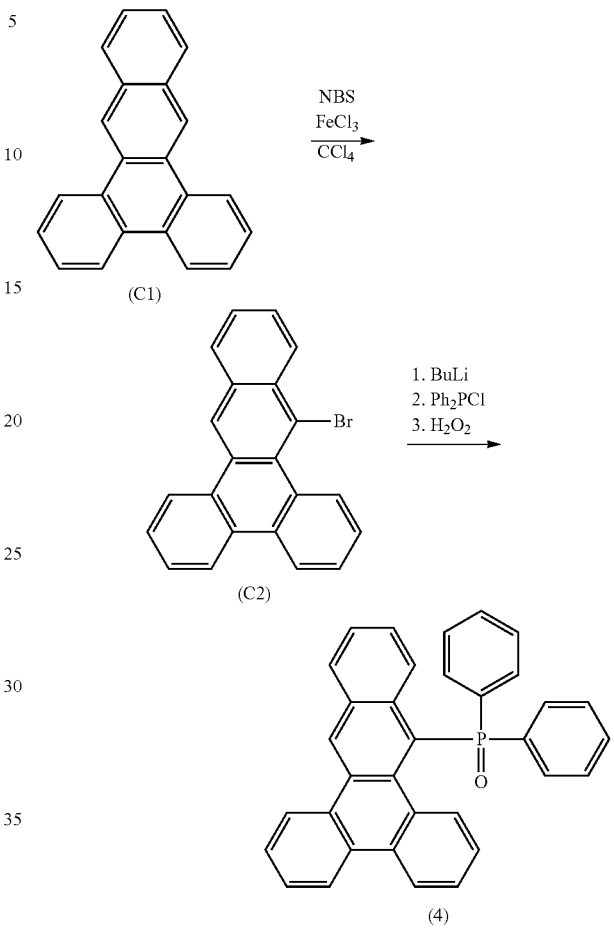

(4)

(4-1) Synthesis of Intermediate (C1)

Referring to the synthesis examples described in "J. Org. Chem., 2004, 69, p.8445-8450", the intermediate (C1) was synthesized.

(4-2) Synthesis of Intermediate (C2)

Carbon tetrachloride (1,500 mL) was added to the intermediate (C1) (6.25 g, 22.5 mmol), N-bromosuccinimide (4.00 g, 22.5 mmol) and iron(III) chloride hexahydrate (182 mg, 0.675 mmol), and the mixture was stirred while heating under reflux for six hours.

After the completion of the reaction, the solvent was distilled off at reduced pressure. The mixture was purified by silica gel column chromatography, and the intermediate (C2) (5.55 g, 15.5 mmol, yield 69%) was thus obtained.

(4-3) Synthesis of Compound (4)

In an argon atmosphere, the intermediate (C2) (3.00 g, 8.40 mmol) was dissolved in tetrahydrofuran (60 mL), and after cooling the solution to −78° C., n-butyllithium (2.50M hexane solution, 5.71 mL, 14.3 mmol) was dropped over 30 minutes. After stirring at −78° C. for an hour, the temperature was raised to −50° C., and diphenylphosphine chloride (1.85 g, 8.40 mmol) was added. The temperature was raised to room temperature, and the mixture was stirred for six hours. Then, the reaction was stopped by adding methanol (50 mL) to the mixture, and then the solvent was distilled off at reduced pressure.

The residue was dissolved in dichloromethane (80 mL), and hydrogen peroxide solution (12 mL) was added. The mixture was stirred again for seven hours. Subsequently, the mixture was washed with a salt solution, dried over magnesium sulfate and then concentrated. Then, the mixture was purified by silica gel column chromatography, and a compound (1.17 g, 2.44 mmol, yield 29%) was thus obtained. As a result of mass spectrometry, the m/e value of the compound was 478, and the compound was identified as the compound (4) (Exact mass: 478.15).

Example 5

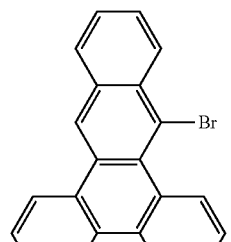

(C2)

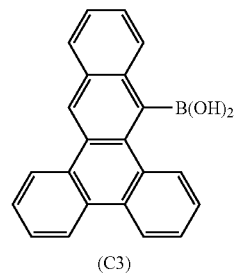

(C3)

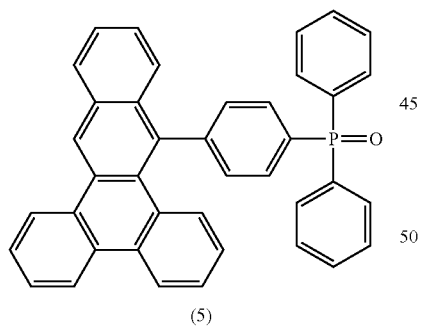

(5)

(5-1) Synthesis of Intermediate (C3)

In an argon atmosphere, the intermediate (C2) (3.00 g, 8.40 mmol) and tetrahydrofuran (80 mL) were mixed and cooled to −78° C. Then, n-butyllithium (1.60M hexane solution, 5.51 mL, 8.82 mmol) was added, and the temperature was raised to 0° C. over two hours. Next, the mixture was cooled to −78° C. again, and after adding trimethoxyborane (2.30 g, 22.1 mmol) and stirring at −78° C. for 20 minutes, the temperature was raised to room temperature over eight hours.

After the completion of the reaction, an aqueous hydrochloric acid solution (1M, 20 mL) was added, and the mixture was stirred at room temperature for an hour, followed by extraction using ethyl acetate. The solution was dried over magnesium sulfate, then concentrated and suspended in and washed with hexane, and the intermediate (C3) (1.76 g, 5.46 mmol, yield 65%) was obtained by recovery through filtration.

(5-2) Synthesis of Compound (5)

In an argon atmosphere, 1,4-dioxane (50 mL) was added to the intermediate (C3) (1.65 g, 5.12 mmol), (4-bromophenyl)phosphine oxide (1.83 g, 5.12 mmol), tris(dibenzylideneacetone)dipalladium(0) (70 mg, 0.0768 mmol), triphenylphosphine (147 mg, 0.559 mmol) and tripotassium phosphate (6.53 g, 30.8 mmol), and the mixture was stirred at 100° C. for eight hours.

After the completion of the reaction, the mixture was diluted with water, followed by extraction using chloroform. Subsequently, the mixture was washed with a saturated salt solution, dried over magnesium sulfate and then concentrated. Then, the mixture was purified by silica gel column chromatography, and then a compound (1.68 g, 3.02 mmol, yield 59%) was obtained by recrystallization from ethyl acetate. As a result of mass spectrometry, the m/e value of the compound was 554, and the compound was identified as the compound (5) (Exact mass: 554.63).

Example 6

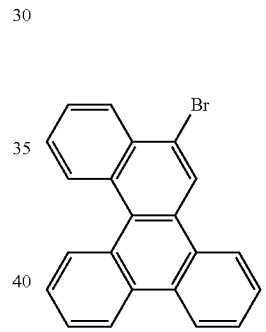

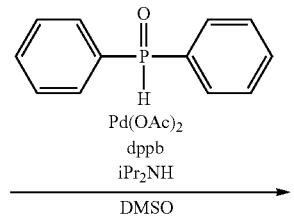

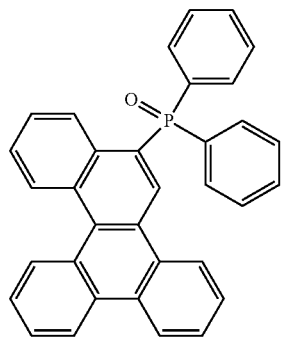

(6)

In an argon atmosphere, dimethyl sulfoxide (30 mL) was added to 10-bromobenzo[g]chrysene (3.57 g, 10.0 mmol), palladium(II) acetate (2.25 g, 1.00 mmol), 1,4-bis(diphenylphosphino)butane (4.26 g, 1.00 mmol) and diisopropylamine (4.05 g, 40.0 mmol), and the mixture was stirred at 100° C. for six hours.

After cooling to room temperature, water and toluene were added. The organic layer was separated, washed with a saturated salt solution and then dried over magnesium sulfate, and the solvent was distilled off at reduced pressure.

The residue obtained was purified by silica gel column chromatography, and then a compound (4.20 g, 8.78 mmol, yield 88%) was obtained by recrystallization from toluene. As a result of mass spectrometry, the m/e value of the compound was 478, and the compound was identified as the compound (6) (Exact mass: 478.53).

All compounds included in the scope of the claims can be synthesized referring to the synthetic reactions above using known reactions and known raw materials according to need.

[Production of Organic Electroluminescence Device]

Next, a specific method for producing an organic EL device is shown. The driving voltage, the external quantum efficiency and the lifetime of the organic EL device obtained in each example were measured in accordance with the following methods.

(Methods for Measuring Capability of Organic EL Device)

(1) Driving Voltage

A current was applied between an anode (an ITO transparent electrode) and a metal cathode (metal Al) in such a manner that the current density became 10 mA/cm$^2$, and the voltage (unit: V) was measured.

(2) External Quantum Efficiency

A voltage was applied to an organic EL device in such a manner that the current density became 10 mA/cm$^2$, and the spectral radiance spectrum was measured using a spectroradiometer "CS-1000" (manufactured by Konica Minolta, Inc.). From the spectral radiance spectrum obtained, the external quantum efficiency (at 10 mA/cm$^2$, unit: %) was calculated assuming that Lambertian radiation occurred.

Using the maximum radiance efficiency and the radiance efficiency ratio at 10 mA/cm$^2$, the maximum external quantum efficiency (EQE max.) was calculated from the external quantum efficiency (at 10 mA/cm$^2$).

(3) Lifetime

A continuous direct-current test was conducted with an initial current density set at 50 mA/cm$^2$, and the time which was required until the brightness decreased to 90% of the brightness at the start of the test (LT90) was measured.

Example 7 [Production of Organic EL Device]

A glass substrate with an ITO transparent electrode (anode) of 25 mm×75 mm×1.1 mm (thickness) (manufactured by GEOMATEC Co., Ltd.) was subjected to ultrasonic cleaning in isopropyl alcohol for five minutes and then to UV ozone cleaning for 30 minutes. The glass substrate with the transparent electrode line after cleaning was attached to a substrate holder of a vacuum evaporator, and the compound K-1 below was first deposited on the surface with the transparent electrode line to cover the transparent electrode, and a K-1 film having a thickness of 5 nm was thus formed. An acceptor layer was formed in this manner.

Next, the compound HT-1 below as a first hole transporting material was deposited on the acceptor layer to form an HT-1 film having a thickness of 80 nm, and a first hole transporting layer was thus formed.

Next, the compound HT-2 below was deposited on the first hole transporting layer to form an HT-2 film having a thickness of 10 nm, and a second hole transporting layer was thus formed.

Furthermore, a film of the compound BH-1 below and the compound BD-1 below at a mass ratio of 24:1 was formed on the HT-2 film by co-deposition, and a light emitting layer having a thickness of 25 nm was thus formed.

Subsequently to the formation of the light emitting layer, a film of the compound (3) below and 8-quinolinolato-lithium (Liq) at a mass ratio of 50:50 was formed by co-deposition, and an electron transporting layer having a thickness of 25 nm was thus formed.

Liq was deposited on the electron transporting layer, and an electron injecting layer having a thickness of 1 nm was thus formed. Furthermore, metal Al was deposited on the electron injecting layer, and a metal cathode having a thickness of 80 nm was thus formed. An organic EL device was produced in this manner.

The rough structure of the organic EL device obtained was as shown below. In this regard, the values in the brackets indicate the thicknesses (unit: nm), and the values with % in the brackets indicate the mass concentration of BD-1 in the light emitting layer and the mass concentration of Liq in the electron transporting layer.

"ITO (130)/K-1 (5)/HT-1 (80)/HT-2 (10)/BH-1:BD-1 (25, 4%)/compound (3): Liq (25, 50%)/Liq (1)/Al (80)"

Also, the properties of the organic EL device obtained were measured in accordance with the above methods. The results are shown in Table 1.

(Compounds Used in Example 7)

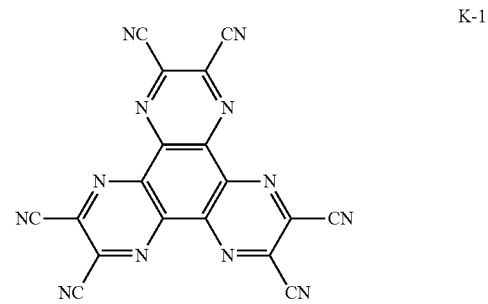

K-1

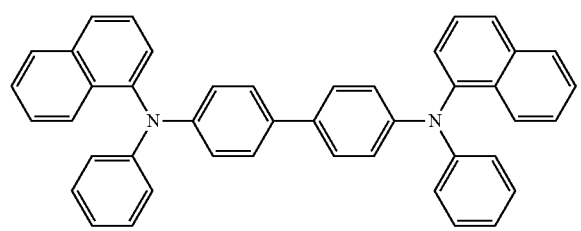

HT-1

-continued

HT-2

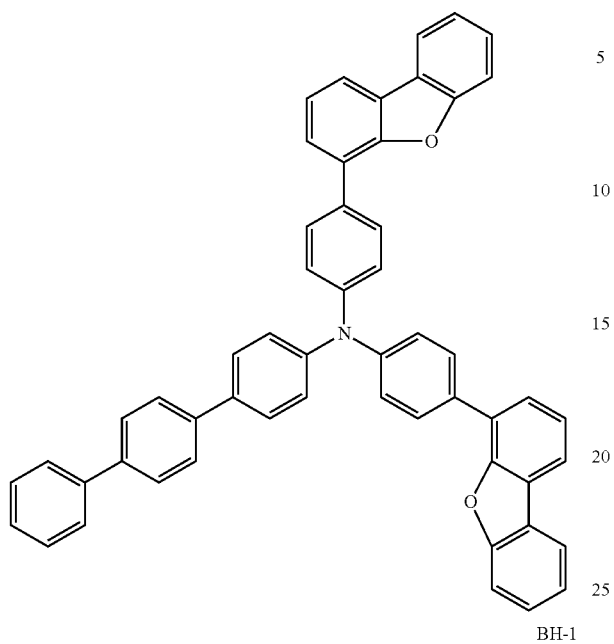

BH-1

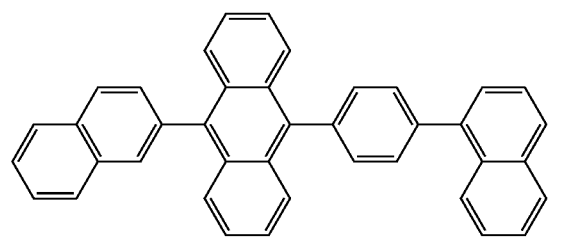

BD-1

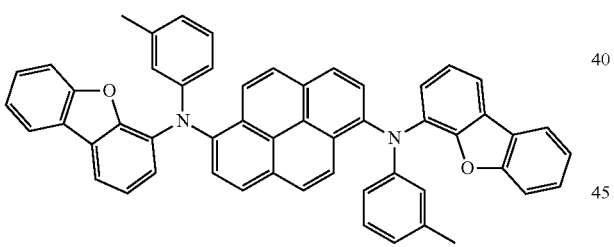

(3)

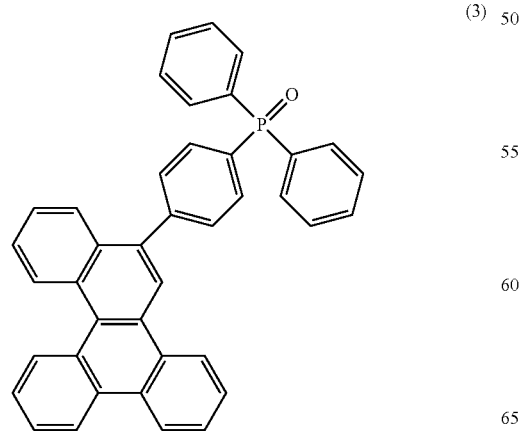

Example 8

An organic EL device was produced in a similar manner as in Example 7 except that the compound (6) below was used instead of the compound (3). The properties of the organic EL device obtained were measured in accordance with the above methods. The results are shown in Table 1.

(6)

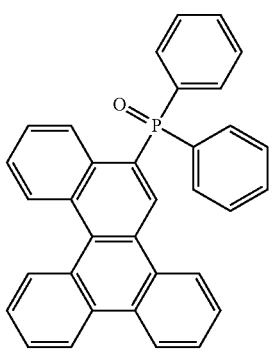

Comparative Examples 1 and 2

Organic EL devices were produced in a similar manner as in Example 7 except that the comparative compound 1 or 2 below was used instead of the compound (3). The properties of the organic EL devices obtained were measured in accordance with the above methods. The results are shown in Table 1.

Comparative Compound 1

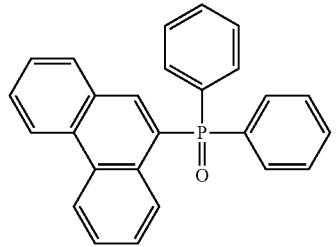

Comparative Compound 2

TABLE 1

| | Electron transporting layer | Results of measurement | | |
|---|---|---|---|---|
| | Electron transporting material | Driving voltage (V) (at 10 mA/cm$^2$) | EQE max (%) | Lifetime (hour) [LT90] |
| Example 7 | Compound (3) | 5.7 | 7.4 | 650 |
| Example 8 | Compound (6) | 5.3 | 8.5 | 360 |
| Comparative Example 1 | Comparative compound 1 | 6.4 | 7.3 | 80 |
| Comparative Example 2 | Comparative compound 2 | 5.6 | 7.0 | 250 |

As shown in Table 1, it is seen that the organic EL devices of Example 7 using the compound (3) of the present invention and Example 8 using the compound (6) could have extended lifetimes while the driving voltages and the external quantum efficiency values were maintained at suitable levels, as compared with the organic EL devices of Comparative Examples 1 and 2.

REFERENCE SIGNS LIST

1: Organic electroluminescence device
3: Anode
4: Cathode
5: Light emitting layer
6: Hole transporting zone (hole transporting layer)
7: Electron transporting zone (electron transporting layer)
10: Organic thin film layers

The invention claimed is:
1. A compound represented by the following general formula

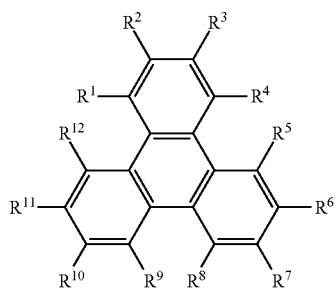

(1)

wherein in the general formula (1), $R^1$ to $R^{12}$ are each independently a hydrogen atom or a substituent selected from the group consisting of a cycloalkyl group having 3 to 50 ring carbon atoms, an aryl group having 6 to 50 ring carbon atoms, an aralkyl group having 7 to 51 carbon atoms which has an aryl group having 6 to 50 ring carbon atoms, an amino group, a mono-substituted or di-substituted amino group which has a substituent selected from an alkyl group having 1 to 50 carbon atoms and an aryl group having 6 to 50 ring carbon atoms, an alkoxy group which has an alkyl group having 1 to 50 carbon atoms, an aryloxy group which has an aryl group having 6 to 50 ring carbon atoms, a mono-substituted, di-substituted or tri-substituted silyl group which has a substituent selected from an alkyl group having 1 to 50 carbon atoms and an aryl group having 6 to 50 ring carbon atoms, a haloalkyl group having 1 to 50 carbon atoms, a halogen atom, a cyano group, a nitro group, a sulfonyl group which has a substituent selected from an alkyl group having 1 to 50 carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxy group, an alkyl-substituted or aryl-substituted carbonyl group, a carboxyl group, a vinyl group, a (meth)acryloyl group, an epoxy group and an oxetanyl group, and at least a pair selected from $R^1$ and $R^2$, $R^2$ and $R^3$, $R^3$ and $R^4$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ may combine to form a ring, provided that one of $R^3$ or $R^4$ is a group represented by the following general formula (2);

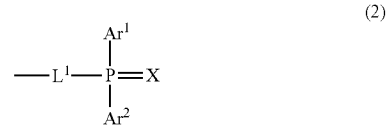

(2)

wherein in the general formula (2),
X represents an oxygen atom, a sulfur atom or a selenium atom,
$L^1$ is a direct bond, a substituted or unsubstituted arylene group having 6 to 60 ring carbon atoms or a substituted or unsubstituted heteroarylene group having 5 to 60 ring atoms,
$Ar^1$ and $Ar^2$ are each independently a substituted or unsubstituted aryl group having 6 to 60 ring carbon atoms or a heteroaryl group having 5 to 60 ring atoms, and $Ar^1$ and $Ar^2$ may combine to form a ring.

2. The compound according to claim 1, which is represented by the following general formula (1-i) or (1-ii):

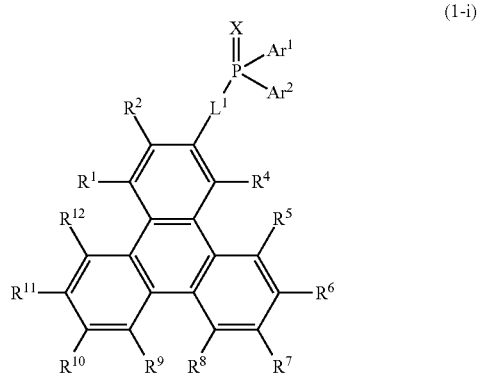

(1-i)

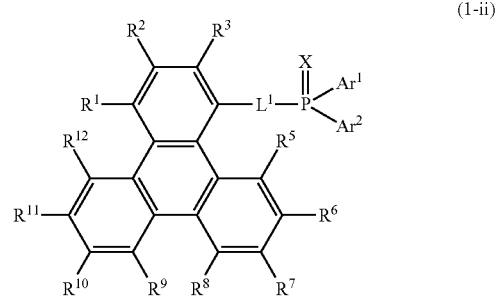

(1-ii)

wherein in the general formulae (1-i) and (1-ii), at least a pair selected from $R^1$ and $R^2$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ in the general formula (1-i) combine to form a ring, at least a pair selected from $R^1$ and $R^2$, $R^2$ and $R^3$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ in the general formula (1-ii) combine to form a ring, and the remaining of $R^1$ to $R^{12}$, and X, $L^1$, $Ar^1$ and $Ar^2$ are as defined in claim 1.

3. The compound according to claim 1, wherein the pair in $R^1$ to $R^{12}$ combine to form a ring, and the ring is a substituted or unsubstituted aromatic ring or a substituted or unsubstituted heteroaromatic ring.

4. The compound according to claim 1, wherein the pair in $R^1$ to $R^{12}$ combine to form a ring, and the ring is formed by the following partial structure:

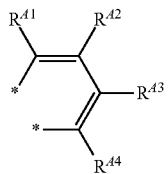

wherein $R^{A1}$ to $R^{A4}$ are each independently a hydrogen atom or a substituent, and * represents a binding site to a carbon atom.

5. The compound according to claim 1, which is represented by the following general formula (1-1) or (1-2):

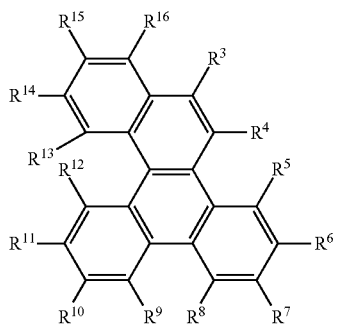

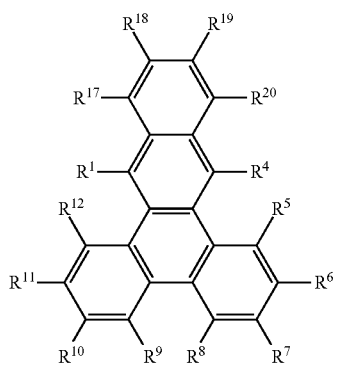

wherein in the general formula (1-1), one of $R^3$ or $R^4$ is a group represented by the general formula (2), and $R^{13}$ to $R^{16}$ are each independently a hydrogen atom or a substituent the same as $R^1$ to $R^{12}$ that are not represented by the general formula (2), and at least a pair selected from $R^5$ and $R^6$, $R^6$ and $R^7$, $R^7$ and $R^8$, $R^9$ and $R^{10}$, $R^{10}$ and $R^{11}$, $R^{11}$ and $R^{12}$, $R^{13}$ and $R^{14}$, $R^{14}$ and $R^{15}$ and $R^{15}$ and $R^{16}$ in the general formula (1-1') may combine to form a ring, and in the general formula (1-2), is a group represented by the general formula (2), and $R^{17}$ to $R^{20}$ are each independently a hydrogen atom or a substituent the same as $R^1$ to $R^{12}$ that are not represented by the general formula (2), and at least a pair selected from $R^1$ and $R^{17}$, $R^{17}$ and $R^{18}$, $R^{18}$ and $R^{19}$, $R^{19}$ and $R^{20}$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ in the general formula (1-2') may combine to form a ring.

6. The compound according to claim 5, which is represented by the following general formula (1-1') or (1-2'):

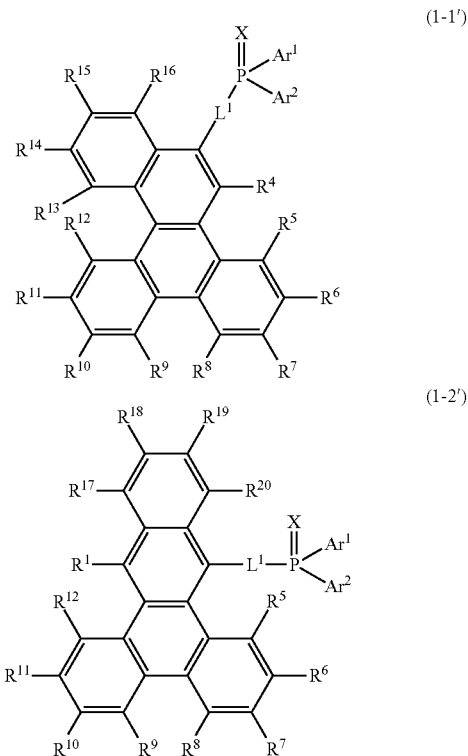

wherein in the general formulae (1-1') and (1-2'), X represents an oxygen atom, a sulfur atom or a selenium atom, $L^1$ is a direct bond, a substituted or unsubstituted arylene group having 6 to 60 ring carbon atoms or a substituted or unsubstituted heteroarylene group having 5 to 60 ring atoms, $Ar^1$ and $Ar^2$ are each independently a substituted or unsubstituted aryl group having 6 to 60 ring carbon atoms or a heteroaryl group having 5 to 60 ring atoms, and $Ar^1$ and $Ar^2$ may combine to form a ring, provided that at least a pair selected from $R^5$ and $R^6$, $R^6$ and $R^7$, $R^7$ and $R^8$, $R^9$ and $R^{10}$, $R^{10}$ and $R^{11}$, $R^{11}$ and $R^{12}$, $R^{13}$ and $R^{14}$, $R^{14}$ and $R^{15}$ and $R^{15}$ and $R^{16}$ in the general formula (1-1') may combine to form a ring and that at least a pair selected from $R^1$ and $R^{17}$, $R^{17}$ and $R^{18}$, $R^{18}$ and $R^{19}$, $R^{19}$ and $R^{20}$, $R^5$ and $R^6$, $R^6$ and $R^7$, $R^7$ and $R^8$, $R^9$ and $R^{10}$, $R^{10}$ and $R^{11}$ and $R^{11}$ and $R^{12}$ in the general formula (1-2') may combine to form a ring.

7. The compound according to claim 6, wherein $R^1$ and $R^4$ to $R^{20}$ in the general formulae (1-1') and (1-2') are all independent from each other and do not combine to form a ring.

8. The compound according to claim 6, which is represented by the following general formula (1-1″) or (1-2″):

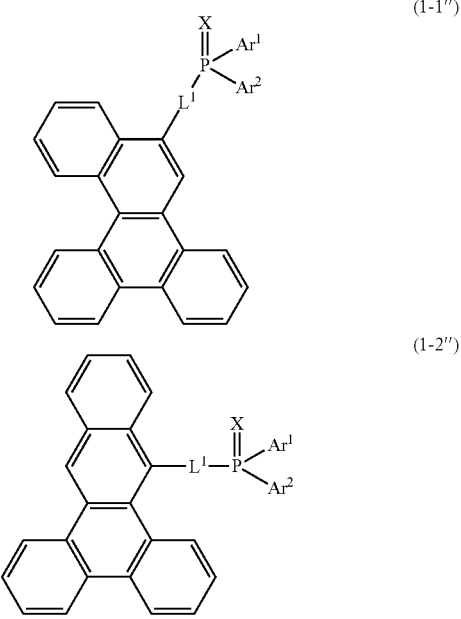

wherein in the general formulae (1-1″) and (1-2″), X represents an oxygen atom, a sulfur atom or a selenium atom, L¹ is a direct bond, a substituted or unsubstituted arylene group having 6 to 60 ring carbon atoms or a substituted or unsubstituted heteroarylene group having 5 to 60 ring atoms, and Ar¹ and Ar² are each independently a substituted or unsubstituted aryl group having 6 to 60 ring carbon atoms or a heteroaryl group having 5 to 60 ring atoms, and Ar¹ and Ar² may combine to form a ring.

9. The compound according to claim 1, wherein at least one of Ar¹ and Ar² is a substituted or unsubstituted aryl group having 6 to 60 ring carbon atoms.

10. The compound according to claim 9, wherein Ar¹ and Ar² are both a substituted or unsubstituted aryl group having 6 to 60 ring carbon atoms.

11. The compound according to claim 10, wherein Ar¹ and Ar² are both a substituted or unsubstituted aryl group having 6 to 13 ring carbon atoms.

12. The compound according to claim 10, wherein Ar¹ and Ar² are each independently a substituted or unsubstituted phenyl group, a substituted or unsubstituted naphthyl group, a substituted or unsubstituted biphenylyl group or a substituted or unsubstituted fluorenyl group.

13. The compound according to claim 1, wherein X is an oxygen atom or a sulfur atom.

14. The compound according to claim 1, wherein L¹ is a direct bond.

15. The compound according to claim 1, wherein L¹ is a phenylene group, a naphthylene group, an anthrylene group, a biphenylylene group, a terphenylylene group, a benzanthrylene group, a phenanthrylene group, a benzophenanthrylene group, a fluorenylene group, a 9,9-di-substituted fluorenylene group, a benzofluorenylene group, a dibenzofluorenylene group, a picenylene group, a tetracenylene group, a pentacenylene group, a pyrenylene group, a chrysenylene group, a benzochrysenylene group, an s-indacenylene group, an as-indacenylene group, a fluoranthenylene group, a benzofluoranthenylene group, a perylenylene group, a coronenylene group or a dibenzanthracenylene group.

16. A material for an organic electroluminescence device comprising the compound according to claim 1.

17. An organic electroluminescence device comprising one or more organic thin film layers which includes at least a light emitting layer between an anode and a cathode which face each other, wherein at least one of the organic thin film layers comprises the compound according to claim 1.

18. The organic electroluminescence device according to claim 17, which comprises an electron transporting zone between the light emitting layer and the cathode, wherein the electron transporting zone comprises the compound represented by the following general formula (1):

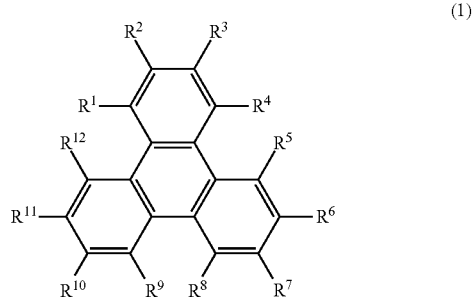

wherein in the general formula (1), R¹ to R¹² are each independently a hydrogen atom or a substituent selected from the group consisting of a cycloalkyl group having 3 to 50 ring carbon atoms, an aryl group having 6 to 50 ring carbon atoms, an aralkyl group having 7 to 51 carbon atoms which has an aryl group having 6 to 50 ring carbon atoms, an amino group, a mono-substituted or di-substituted amino group which has a substituent selected from an alkyl group having 1 to 50 carbon atoms and an aryl group having 6 to 50 ring carbon atoms, an alkoxy group which has an alkyl group having 1 to 50 carbon atoms, an aryloxy group which has an aryl group having 6 to 50 ring carbon atoms, a mono-substituted, di-substituted or tri-substituted silyl group which has a substituent selected from an alkyl group having 1 to 50 carbon atoms and an aryl group having 6 to 50 ring carbon atoms, a haloalkyl group having 1 to 50 carbon atoms, a halogen atom, a cyano group, a nitro group, a sulfonyl group which has a substituent selected from an alkyl group having 1 to 50 carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxy group, an alkyl-substituted or aryl-substituted carbonyl group, a carboxyl group, a vinyl group, a (meth)acryloyl group, an epoxy group and an oxetanyl group, and at least a pair selected from R¹ and R², R² and R³, R³ and R⁴, R⁵ and R⁶, R⁶ and R⁷, R⁷ and R⁸, R⁹ and R¹⁰, R¹⁰ and R¹¹ and R¹¹ and R¹² may combine to form a ring, provided that one of R³ or R⁴ is a group represented by the following general formula (2):

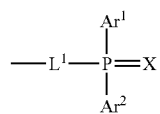
(2)

wherein in the general formula (2), X represents an oxygen atom, a sulfur atom or a selenium atom, $L^1$ is a direct bond, a substituted or unsubstituted arylene group having 6 to 60 ring carbon atoms or a substituted or unsubstituted heteroarylene group having 5 to 60 ring atoms, $Ar^1$ and $Ar^2$ are each independently a substituted or unsubstituted aryl group having 6 to 60 ring carbon atoms or a heteroaryl group having 5 to 60 ring atoms, and $Ar^1$ and $Ar^2$ may combine to form a ring.

19. The organic electroluminescence device according to claim 18, wherein the electron transporting zone further comprises at least one selected from an electron-donating dopant and an organometallic complex.

20. The organic electroluminescence device according to claim 19, wherein the electron-donating dopant is at least one selected from an alkali metal, an alkali metal compound, an alkaline earth metal, an alkaline earth metal compound, a rare-earth metal and a rare-earth metal compound.

21. The organic electroluminescence device according to claim 19, wherein the organometallic complex is at least one selected from an organometallic complex containing an alkali metal, an organometallic complex containing an alkaline earth metal and an organometallic complex containing a rare-earth metal.

22. An electronic equipment provided with the organic electroluminescence device according to claim 17.

23. The compound according to claim 8, wherein $L^1$ is a direct bond or a phenylene group.

24. The compound according to claim 23, wherein X represents an oxygen atom.

25. The compound according to claim 6, wherein the compound is represented by formula (1-1').

26. The compound according to claim 8, wherein the compound is represented by formula (1-1").

27. The organic electroluminescence device according to claim 18, wherein the electron transporting zone comprises the compound represented by the following general formula (1-1"):

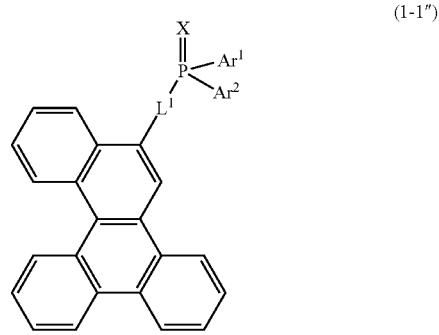
(1-1")

wherein in the general formula (1-1"), X represents an oxygen atom, a sulfur atom or a selenium atom, $L^1$ is a direct bond, a substituted or unsubstituted arylene group having 6 to 60 ring carbon atoms or a substituted or unsubstituted heteroarylene group having 5 to 60 ring atoms, and $Ar^1$ and $Ar^2$ are each independently a substituted or unsubstituted aryl group having 6 to 60 ring carbon atoms or a heteroaryl group having 5 to 60 ring atoms, and $Ar^1$ and $Ar^2$ may combine to form a ring.

* * * * *